United States Patent
Gilmer et al.

(10) Patent No.: US 9,566,342 B2
(45) Date of Patent: Feb. 14, 2017

(54) COMPOUNDS FOR TREATMENT OF HEART FAILURE

(75) Inventors: John Gilmer, Dublin (IE); Mark Ledwidge, Cork (IE); Ken McDonald, Dublin (IE); Pat O'Flynn, Cork (IE)

(73) Assignee: SOLVOTRIN INNOVATIONS LIMITED, Cork (IE)

( * ) Notice: Subject to any disclaimer, the term of this patent is extended or adjusted under 35 U.S.C. 154(b) by 484 days.

(21) Appl. No.: 13/992,663

(22) PCT Filed: Dec. 8, 2011

(86) PCT No.: PCT/EP2011/072243
§ 371 (c)(1),
(2), (4) Date: Aug. 23, 2013

(87) PCT Pub. No.: WO2012/076667
PCT Pub. Date: Jun. 14, 2012

(65) Prior Publication Data
US 2013/0338118 A1   Dec. 19, 2013

(30) Foreign Application Priority Data
Dec. 8, 2010   (GB) .................................. 1020811.4

(51) Int. Cl.
| | |
|---|---|
| *A61K 45/06* | (2006.01) |
| *A61K 47/48* | (2006.01) |
| *A61K 31/00* | (2006.01) |
| *A61K 31/21* | (2006.01) |
| *A61K 31/4458* | (2006.01) |
| *A61K 31/4462* | (2006.01) |
| *A61K 31/4465* | (2006.01) |
| *A61K 31/65* | (2006.01) |
| *C07C 237/26* | (2006.01) |

(52) U.S. Cl.
CPC ............. *A61K 47/481* (2013.01); *A61K 31/00* (2013.01); *A61K 31/21* (2013.01); *A61K 31/4458* (2013.01); *A61K 31/4462* (2013.01); *A61K 31/4465* (2013.01); *A61K 31/65* (2013.01); *A61K 45/06* (2013.01); *C07C 237/26* (2013.01)

(58) Field of Classification Search
CPC ............................ A61K 45/06; A61K 487/481
See application file for complete search history.

(56) References Cited

U.S. PATENT DOCUMENTS 5,030,641 A * 7/1991 Simon ................... C07D 207/16
514/345

FOREIGN PATENT DOCUMENTS

| EP | 1336602 A1 | 8/2003 | | |
|---|---|---|---|---|
| IT | EP 1336602 A1 * | 8/2003 | ........... | C07C 291/02 |
| WO | WO-00/61537 | 10/2000 | | |
| WO | WO-2006/102071 | 9/2006 | | |

OTHER PUBLICATIONS

Tang et al. J. of Cerebral Blood Flow and Metabolism, vol. 30, published online Sep. 2009, pp. 119-129.*
Brown et al. Arterioscler. Thromb. Vasc. Biol., 2004, Issue 24, No. 4, pp. 733-738.*
Bernardelli, Cesare et al., "Über die Einhorn-Reaktion mit Aminosäuren, III*", Liebigs Ann. Chem. 706, 243-249 (1967).
Brown, David L., et al., "Clinical and Biochemical Results of the Metalloproteinase Inhibition with Subantimicrobial Doses of Doxycycline to Prevent Acute Coronary Syndromes (MIDAS) Pilot Trial", Arterioscler Thromb Vasc Biol. Apr. 2004, 8 pages.
Chung, Ada W.Y., et al., "Matrix metalloproteinase-2 and -9 exacerbate arterial stiffening and angiogenesis in diabetes and chronic kidney disease", Cardiovascular Research (2009) 84, 494-504.
Hori, Yasutomo et al., "Doxycycline Attenuates Isoproterenol-Induced Myocardial Fibrosis and Matrix Metalloproteinase Activity in Rats", Biol. Pharm. Bull. vol. 32, No. 10, 2009, 1678-1682.
Ishibashi, Toshiyuki et al., "Advanced Glycation End Product-Mediated Matrix Metallo-proteinase-9 and Apoptosis via Renin-Angiotensin System in Type 2 Diabetes", Journal of Atherosclerosis and Thrombosis, 2010, vol. 17, No. 6, pp. 578-589.
Li, Xun et al., "Recent Developments in Patent Anti-Cancer Agents Targeting the Matrix Metalloproteinases (MMPS)", Recent Patents on Anti-Cancer Drug Discovery, 2010, 5, 109-141.
Liu Hongzhi et al: "Doxycycline, a Nonspecific Matrix Metalloproteinase Inhibitor, Attenuates Left Ventricular Remodelling and Failure in a Rat Model of Adriamycin-Induced Dilated Cardiomyopathy", Database accession No. PREV201100011574; & CIRCULTION, vol. 122, No. 2, Jul. 2010, pp. E133-E134.
Roy, Roopali et al., "Matrix Metalloproteinases As Novel Biomarkers and Potential Therapeutic Targets in Human Cancer", Journal of Clinical Oncology, vol. 27, No. 31, Nov. 2009, 5287-5297.
Tang, Minke et al., "Minocycline reduces neuronal death and attenuates microglial response after pediatric asphyxia cardiac arrest", Journal of Cerebral Blood Flow & Metabolism (2010) 30, 119-129.

(Continued)

*Primary Examiner* — Samira Jean-Louis
(74) *Attorney, Agent, or Firm* — Foley & Lardner LLP; Antoinette F. Konski

(57) ABSTRACT

A combination of: a first tetracycline (TC) component; and a second component capable of releasing nitric oxide (NO) or a nitrate capable of mimicking NO effects in vivo (NO mimetic). The combinations of the invention advantageously act as more effective MMP modulators with selective reductions in circulating MMP-9 levels in-vivo and inhibitory effects on MMP-2 and MMP-9 levels in-vitro. The combinations of the invention also advantageously act as modulators of inflammation mediators. The co-existence of abnormalities of MMP enzymes and inflammation in many diseases make these characteristics advantageous. Therefore, the various combinations of the invention find utility in medical applications where MMPs and/or inflammation is implicated.

4 Claims, 9 Drawing Sheets

(56) References Cited

OTHER PUBLICATIONS

Thrailkill, Kathryn M. et al., "Disease and gender-specific dysregulation of NGAL and MMP-9 in type 1 diabetes mellitus", Endocrine, Apr. 2010; 37(2); 336-343.

Wang, Peng George et al., "Nitric Oxide Donors: Chemical Activities and Biological Applications", Chem. Rev. 202, 102, 1091-1134.

Wang, Ying et al., "Genetic polymorphism c.1562C>T of the MMP-9 is associated with macroangiopathy in type 2 diabetes mellitus", Biochemical and Biophysical Research Communications 391 (2010), 113-117.

Zhou, S. et al., "Matrix metalloproteinase-9 polymorphism contributes to blood pressure and arterial stiffness in essential hypertension", Journal of Human Hypertension (2007) 21, 861-867.

* cited by examiner

A doxycycline hyclate (striped bars) and SI1004 (solid bars)

B doxycycline hyclate (striped bars) and SI1004 (solid bars)

COMPOUNDS FOR TREATMENT OF HEART FAILURE

CROSS-REFERENCE TO RELATED APPLICATIONS

The present application is a national stage application under 35 U.S.C. §371 of International Application No. PCT/EP2011/072243, filed Dec. 8, 2011, which in turn claims priority to United Kingdom Patent Application No. 1020811.4, filed Dec. 8, 2010, the contents of each of which are incorporated herein by reference in their entireties.

FIELD OF THE INVENTION

The present invention relates to a compound comprising a tetracycline, and an associated molecule that is capable of releasing nitric oxide (NO). Also disclosed are methods for the preparation of such compounds, and their use in treating or preventing heart failure, optionally heart failure caused by or associated with diastolic dysfunction.

BACKGROUND TO THE INVENTION

The prevalence of heart failure (HF) is increasing in the developed world and the cost of providing medical care for an expanding HF population imposes an increasingly heavy burden on healthcare systems throughout the world. Most commonly, HF is associated with impaired left ventricular (LV) systolic function. However, at least half of all patients with typical symptoms of congestive HF have a normal or slightly reduced left ventricular ejection fraction (LVEF) (>50%). The predominant cause of heart failure with preserved ejection fraction (HFpEF) is diastolic heart failure (DHF). Heart failure (HF) with preserved ejection fraction (HFpEF) is predominantly caused by hypertension, is often preceded by asymptomatic left ventricular diastolic dysfunction (ALVDD) and has few defined therapies. The predominant aetiological cause of DHF is myocardial fibrosis as a result of long standing hypertension and metabolic abnormalities associated with diabetes and obesity. The rising prevalence of metabolic disease due to the obesity and diabetic epidemics means that DHF is a major public health problem. DHF, similar to systolic HF has a five-year mortality rate of 65%. In many of these patients, diastolic dysfunction caused by hypertensive heart disease (HHD) is implicated as a major contributor, if not a primary cause. Furthermore, the prevalence of asymptomatic diastolic dysfunction in the community is significant with approximately 25-30% of individuals >45 years of age being affected. There are no proven, life-saving therapies for treating DHF. Many of the well-established drug therapies for systolic heart failure have been directed at DHF without success. The diagnosis of DHF can present a challenge in routine clinical practice. The major limitation in the diagnosis of DHF is the identification of diastolic dysfunction (DD), which at present is predominantly reliant on Doppler echocardiographic studies. Echocardiography has been used for many years to provide structural correlates to the clinical picture of HF. It can also measure multiple clinically important parameters of cardiac function, including hemodynamic status and LVEF, volumes and mass. The pathophysiology of DHF includes delayed relaxation, impaired LV filling and/or increased stiffness. These conditions result in an upward displacement of the diastolic pressure-volume relationship with increased end-diastolic, left atrial and pulmo-capillary wedge pressure leading to symptoms of pulmonary congestion. Diagnosis of DHF requires three conditions; (1) presence of signs or symptoms of HF; (2) presence of normal or slightly reduced LVEF (>50%) and (3) presence of increased diastolic filling pressure. Data indicate that the underlying pathophysiology in diastolic dysfunction and DHF is related to myocardial interstitial disease. Collagen is a stable protein and its balanced turnover is estimated to be 80-120 days. Alteration of collagen turnover by various mechanisms can lead to adverse accumulation of collagen in the myocardial interstitium leading to fibrosis, increased tissue stiffness, reduced myocardial compliance and impaired diastolic function. The successful neurohumoral-based approach to pharmacotherapy in HF with systolic dysfunction has not resulted in similarly impressive results in HFpEF, implicating additional pathophysiological signals. Changes in the extracellular matrix (ECM), known as myocardial remodeling, are central abnormalities in many patients with HFpEF and are characterized by inflammation, increased ECM turnover and myocardial fibrosis. Key mediators of inflammation are pro-inflammatory cytokines including interleukins (IL) (IL-1β, IL-6, IL-8) and tumor necrosis factor (TNF)α. Key regulators of the turnover of collagen and extracellular matrix (ECM) in the myocardium are the matrix metalloproteinases (MMPs) and their tissue inhibitors (TIMPs). MMPs in particular have been found to play an important role in both inflammation and fibrosis. MMPs also contribute to collagen degradation and remodeling of the ECM after myocardial infarction. ECM turnover is regulated by matrix metalloproteinases (MMPs), especially the "gelatinases", MMP-2 and MMP-9, and their tissue inhibitors (TIMPs). MMP-2 and MMP-9 knockout models are associated with reduced aortic elastin degradation and protection from pressure overload hypertrophy, fibrosis and dysfunction. In the clinic, independent associations between ALVDD and HFpEF have been identified with markers of inflammation, fibrosis and MMP-9. During ischemic cardiomyopathy, neutrophil proteinase activates latent myocardial MMP, which can degrade the ECM. If unchecked by TIMPs, the ECM continuously degrades, leading to ventricular dilatation and diastolic dysfunction. Despite the emerging awareness of the potential role of collagen metabolism in the pathogenesis of diastolic HF there are as yet no effective therapies for this form of HF. Pharmacological modulation of MMPs may present an opportunity. However, all MMP synthetic inhibitors developed to date have either been ineffective or demonstrated dose- and duration-dependent drug-related side-effects, most which were musculoskeletal-related. Despite some promising animal studies of MMP inhibitors showing attenuation of cardiovascular remodeling in chronic pressure-overload models, the approach of direct inhibition of MMP enzymes has proven too toxic or ineffective in the clinic. An alternative approach in cardiovascular disease would inhibit production and/or secretion of inducible myocardial MMP-9. As well as classic inflammatory diseases such as rheumatoid arthritis, hay fever, periodontitis, inflammation plays an important role in the development and progression of diabetes and a variety of cardiovascular conditions, most notably coronary atherosclerosis and congestive heart failure. The term "Diabetic cardiomyopathy" was coined 4 decades ago and describes a "silent, stiffening" of the heart tissue which can lead to heart failure. There are no symptoms until heart failure occurs. It is present in half of people with diabetes and is more prevalent than well-recognised "silent pumping problem" which has good treatment available. This silent stiffening of the heart is linked to overweight, diabetes, high blood pressure and there are no specific therapies. Over the past 20 years, basic and human research has shown that enzymes in the heart called matrix metallproteinases or MMPs are involved in the stiffening process. They also affect large and small blood vessels and cause eye and kidney damage in diabetes. For example, in patients with diabetic retinopathy, increased MMP-9 activity was observed in retinal microvessels and MMP-9 knockout was protective (Kowluru et al, Abrogation of MMP-9 Gene Protects Against the Development of Retinopathy in Diabetic Mice by Preventing Mitochondrial Damage. Diabetes. 2011 Sep. 20 [Epub ahead of print]). Increased urinary excretion of MMP-9 in patients supports a role for MMP-9 dysregulation in diabetic renal dysfunction (Thrailkill et al., Endocrine. 2010 April; 37(2):336-43). Aortic and coronary arteries of diabetic patients taken at autopsy had higher expression of MMP-9 compared to non-diabetics and were correlated with HbA1c as well as apoptosis (Ishibashi et al., J Atheroscler Thromb. 2010 Jun. 30; 17(6):578-89). Elevated MMP-9 has also been associated with arterial stiffness in patients with diabetes (Chung et al., Cardiovasc Res. 2009 Dec. 1; 84(3):494-504). Furthermore, human genetic polymorphisms associated with MMP-9 elevation support a role for this enzyme in the pathophysiology of vascular disease. The 1562C>T single nucleotide polymorphism (SNP), which affects the promoter region of MMP-9 gene and increases circulating levels of MMP-9, is significantly associated with vascular disease in type 2 diabetes mellitus (Wang et al., Biochem Biophys Res Commun. 2010 Jan. 1; 391(1):113-7). In age and sex matched controls, patients with type 2 diabetes without and with microangiopathy, T allele frequencies were 11.9%, 13.1% and 24.4% respectively (p<0.05). Similarly, in a cohort of asymptomatic hypertensive patients, the 1562C>1 polymorphism is associated with increased T allele frequency, higher plasma MMP-9 and evidence of increased hypertension and vascular stiffness, measured by pulse wave velocity (Zhou et al. J Hum Hypertens. 2007 November; 21(11):861-7). Inflammation is also involved in the development and progression of some cancers (e.g., gallbladder carcinoma). Inflammation is mediated by a complex interplay of mediators such as IL-1 beta, IL-4 and IL-8. IL-1 beta induces COX-2, which causes brain levels of prostaglandin (PG)E2 to rise, thus activating the thermoregulatory center for fever production. In the periphery, IL-1 beta activates IL-1 receptors on the endothelium, resulting in expression of adhesion molecules and chemokines, which facilitate the emigration of neutrophils into the tissue spaces. IL-1 is pro-inflammatory and has been implicated in various pro-inflammatory diseases such as coronary atherosclerosis and congestive heart failure as well as diabetes where recent studies from animals, in-vitro cultures and clinical trials provide evidence that support a causative role for IL-1$\beta$ as the primary agonist in the loss of beta-cell mass in type 2 diabetes. IL-4 is a TH2 type anti-inflammatory and profibrosis cytokine that stimulates and amplifies the inflammatory response by activation of the synthesis of types I and II collagen by fibroblasts and the promotion of the progression of fibrosis. IL-4 also inhibits the proinflammatory response of TNF-$\alpha$, IL-1 and IL-6. IL-4 stimulates inflammatory responses, activates collagen synthesis, promotes fibrosis progression, and inhibits the production of inflammatory cytokines. The patients with CHF had higher IL-4 and PIIINP values than the controls. Comparison of the IL-4 values between the patients and controls showed a significantly greater difference in the CHF patients (12 [12] vs 4 [3] pg/mL; P<0.0001). Recent studies have shown that pro-inflammatory cytokines play a significant contributory role in the pathogenesis of acute heart failure. The purpose of this study was to determine whether the serum IL-8 concentration in patients with acute myocardial infarction (AMI), who were undergoing percutaneous coronary intervention (PCI) was related to the subsequent presence or absence of heart failure. A study by Dominguez-Rodriguez 2006, included 50 patients who underwent successful PCI. During their subsequent stay in the coronary care unit, their maximum degree of heart failure was recorded. Serum levels of IL-8 in patients more severe symptoms (Killip class >I) were significantly higher than those of with less severe symptoms (Killip class I) (P<0.001). By multivariante analysis a higher level of IL-8 was a significant predictor of heart failure after PCI. Similarly in HF, the presence of the metabolic syndrome which puts patients at higher risk, plasma levels of IL-8 (p<0.05) were significantly higher in HF patients with MetS than those without MetS.

Tetracyclines, commonly known for their broad-spectrum antimicrobial properties, have been characterized as pleiotropic immunomodulatory agents. In human studies, sub-antimicrobial doses of the tetracycline, doxycycline, have exerted potentially beneficial effects on inflammation that could promote plaque stability in an effort to prevent acute coronary syndrome, as doxycycline therapy has been shown to lead to a powerful reduction of aneurysmal wall neutrophil and cytotoxic T-cell count; two cell types considered crucial for the process of aneurysm formation. Attempts have been made to attenuate MMP expression to inhibit aortic abdominal aneurysm formation using doxycycline, thereby reducing the need for surgery. Doxycycline has been shown to inhibit secretion of MMP-2 and MMP-9 and is the only drug currently licensed for human use that relies on MMP inhibition. It is currently under evaluation in ALVDD and HF patients in our group for its effects on inflammation, MMPs, myocardial structure and function using cardiac MRI [EudraCT number: 2010-021664-16]. However, in several animal and human studies, the efficacy of MMP inhibition with doxycycline has been questioned. This may reflect non-specific inhibition of the wider MMP family with high doses and/or chronic therapy, involving inhibition of both constitutive and inducible enzymes. It prompted our group to create analogues of doxycycline that target overexpression of inducible MMP-9 rather than direct enzyme inhibition as a more effective and safer approach. Evidence is emerging that members of the MMP and/or A disintegrin and metalloproteinase (ADAM) family can serve not only as potential markers for diagnosis and prognosis, early detection, and risk assessment, but also as indicators of tumor recurrence, metastatic spread, and response to primary and adjuvant therapy for breast cancer. MMP-9 levels in tumor tissue as well as serum, plasma, and urine are significantly elevated in patients with breast cancer. Recently, efforts have focused on the use of MMPs and ADAMs as potential biomarkers of early breast cancer. Studies indicate that urinary MMP-9 and ADAM12, in addition to being predictive markers for breast cancer, may also prove useful as noninvasive breast cancer risk assessment tools. Several independent studies have used circulating MMP-9 activity to predict metastatic spread of disease as well as to monitor patient response to primary and adjuvant therapy and to evaluate outcome. High levels of serum MMP-9 and TIMP-1 are associated with increased incidence of lymph node metastasis and decreased relapse-free and overall survival rates. MMPs may also be useful in predicting therapeutic efficacy. Plasma MMP-9 levels decrease after the surgical removal of primary breast tumors and a progressive decrease in plasma MMP-9 was observed in patients who responded well to adjuvant therapy. Importantly, in all patients who suffered a relapse of disease there was a gradual increase of plasma MMP-9 activity 1 to 8 months before the clinical diagnosis of recurrence. Serum and tissue levels of MMP-9 are significantly higher in patients with pancreatic ductal adenocarcinoma than in patients with chronic pancreatitis and healthy controls. Active MMP-2 levels are upregulated in the pancreatic juice of patients with cancer (100%) as compared with patients with chronic pancreatitis (2%) or normal controls (0%). Several studies have reported that plasma and/or serum levels of MMP-9 and TIMP-1 are elevated in patients with stage III or IV lung cancer when compared with those in patients with nonmalignant lung diseases. Urinary MMP-2 and MMP-9 levels correlate with presence of bladder cancer as well as stage and grade of disease. Several MMP species have been reported in urine from patients with primary tumors in the bladder and prostate including MMP-2, MMP-9, MMP-9/neutrophil gelatinase-associated lipocalin complex and MMP-9 dimer. Each urinary MMP species was detected at significantly higher rates in urine from patients with cancer as compared with controls. The difference in detection of MMP species in the urine of the two types of cancers studied may serve as a tumor-specific fingerprint that can indicate both the presence of a tumor as well as its location. Increased levels of MMP-9 and MMP-2 in urine correlate with increased expression of these proteases in bladder tumor tissue as well. Urinary MMP-9 levels when combined with telomerase analysis of exfoliated cells from voided urine could also increase the sensitivity of cytology, a commonly used method for bladder cancer detection and monitoring. MMP-2 and MMP-9 have been studied as potential prognostic biomarkers of colorectal cancer. Enhanced MMP-9 staining in primary tumors was found to be an independent marker of poor prognosis in a study with T3-T4 node-negative patients. Plasma MMP-2 and MMP-9 levels were significantly elevated in patients with colorectal cancer and those with adenomatous polyps, and significant reduction in both were observed after tumor resections, suggesting their potential as markers for therapeutic efficacy. These MMPs may not be prognostic markers for tumor recurrence, however, since plasma proMMP-2 and -9 activities did not correlate with disease relapse after surgery. Tutton and colleagues investigated whether plasma MMP-2 and MMP-9 levels could be used as a surrogate for tumour expression in colorectal cancer patients and they found significant correlations between plasma levels and tumor pre- and post-op. MMP-2, -9, and -14 are among the most studied MMPs as biomarkers for ovarian cancer. MMP-9 activity in tissue extracts was significantly increased in advanced ovarian cancers (International Federation of Gynecology and Obstetrics stage III) compared with benign tumors and was found to be an independent prognosticator of poor survival. In another study of invasive epithelial ovarian cancer, high stromal expressions of MMP-9 and -14 were significantly correlated with cancer progression and were independent prognostic markers. Tissue MMPs have also been shown to distinguish different histotypes of ovarian cancer, which is a significant finding given that different histotypes have different prognoses. A recent study showed that more than 90% of clear-cell carcinomas expressed moderate to high levels of MMP-2 or MMP-14, compared with 30% to 55% of the other ovarian cancer histotypes (serous, endometroid, and mucinous), whereas MMP-9 was expressed more widely in other histotypes. Importantly, the cellular source of MMPs must be considered when evaluating MMPs as ovarian cancer biomarkers. For example, strong MMP-9 levels in cancer cells were associated with longer survival whereas strong stromal MMP-9 was associated with shorter survival, suggesting a dual role for MMP-9 during ovarian cancer progression. MMP-2, -9, -15, and -26 expression in tissue or serum have been positively correlated with Gleason score in prostate cancer. Among these MMPs, the activities of plasma MMP-2 and -9 increased significantly in metastatic prostate cancer. Analysis of MMP-2 and -9 levels in radical prostatectomy specimens revealed these two as significant predictors of cancer recurrence. These two enzymes may also be markers of therapeutic efficacy, since both the levels and activities of plasma MMP-2 and -9 decreased significantly in metastatic patients after therapy. In addition, increased urinary MMP-9 activity has been shown to distinguish between prostate and other types of cancer (e.g. bladder cancer). MMPs can also be combined with other markers to increase their predictive capability. For example, the mRNA ratio of gelatinases to E-cadherin in biopsy samples independently predicted prostate cancer stage. Elevated tissue levels of MMP-2 and MMP-9 have been reported in aggressive brain tumors. Both latent and activated forms of MMP-2 and MMP-9 have been detected in the cerebrospinal fluid of patients with brain tumors. In studies of primary glial tumors and other central nervous system tumors, we have recently shown that detection of MMP-2, MMP-9, MMP-9/neutrophil gelatinase-associated lipocalin complex, and/or vascular endothelial growth factor in the urine predicted disease status and therapeutic efficiency of patients with brain cancer. Importantly, these studies showed that the upregulation of MMP-2 and -9 in the source tumor tissue was also reflected in CSF as well as in urine of these patients. Tumor cells overexpress proteases and/or induce expression of these enzymes in neighboring stromal cells in order to degrade the basement membrane and invade the surrounding tissue. Several MMPs have been implicated in the ECM degradation associated with tumor growth and angiogenesis. This proteolytic activity is also required for a cancer cell to invade a nearby blood vessel (intravasation) and then extravasate at a distant location and invade the distant tissue in order to seed a new metastatic site. MMPs have been shown to promote angiogenesis through their release of angiogenic factors stored in the ECM such as vascular endothelial growth factor (VEGF) and basic fibroblast growth factor (bFGF; 3). Stroma-derived MMP-9 can facilitate the liberation of ECM-sequestered VEGF during tumor angiogenesis. MMPs play complex and sometimes conflicting roles in regulating angiogenesis. Remodeling of the ECM during angiogenesis is accomplished largely through the activity of MMPs. Angiogenic mitogens, such as bFGF and VEGF, can stimulate the production of MMPs by capillary endothelial cells. Studies have also demonstrated that MMPs are involved in the angiogenic switch, one of the earliest stages of tumor growth and progression. It has been shown that MMP-9 can be a regulator of the angiogenic switch in a pancreatic tumor model, further confirming the pro-angiogenic role of MMPs. These findings strongly suggest that MMP activity is critical, not only to the initiation of angiogenesis, but to the maintenance of the growing vascular bed, which in turn supports tumor growth and metastasis. MMP activity can, however, result in the production of negative regulators of angiogenesis as well. ECM degradation products display unique biologic properties that can trigger a variety of cellular signals. MMPs have also been implicated in the epithelial to mesenchymal transition (EMT), a hallmark of cancer progression to metastasis. Activation of growth factors and cleavage of adhesion molecules are some of the proposed mechanisms underlying MMP-induced EMT. Recent studies point to an emerging role for MMPs in modulating aspects of immunity and inflammation during tumorigenesis. A variety of cytokines, cytokine receptors, and chemokines have been found to undergo MMP-mediated cleavage. In breast cancer, MMP-9 expression is upregulated in tumor-associated stromal cells including neutrophils, macrophages, and lymphocytes and may play a role in tumor-associated inflammation. Several members of the MMP and ADAM family can regulate cellular proliferation by modulating the bioavailability of growth factors or cell-surface receptors. Ligands for several growth factor receptors are processed by MMP/ADAM family members as well. There are known clinical benefits of MMP inhibition in cancer management (for example Neovastat (AstraZeneca) is currently under evaluation in phase II renal cell carcinoma). However, most MMP inhibitors are too toxic for use in the clinic and adverse effects of MMP inhibitors (e.g. musculoskeletal adverse effects) limit their use. Furthermore, there may be problems with potent, broad spectrum, MMP inhibition. For example, there are some data suggesting that tumour progression is inversely proportional to MMP-3. Accordingly, it is not known if MMP-3 sparing or MMP-3 inhibiting effects are preferable. Recent developments in anti-cancer agents targeting the matrix metalloproteinases have been reviewed (Li, et al., *Recent Patents on Anti-Cancer Drug Discovery* 2010, 5: 109-141) and show that MMP inhibitors are classified into three main pharmacologic categories: Collagen peptidomimetics, non-peptidomimetics and tetracycline derivatives. Collagen peptidomimetics can be further subdivided into hydroxamates, carboxylates, aminocarboxylates, sulfhydryls, phosphoric acid derivatives. Most MMP inhibitors in clinical development are hydroxamate derivatives, e.g. batimastat and marimastat, illomastat. The lead compounds have been largely unsuccessful because of toxicity and or lack of efficacy. For example, Batimastat can only be administered intraperitoneally and intrapleurally and further development has been suspended. In the case of Marimastat, no benefit over placebo was seen in patients with breast and lung cancer. Severe musculoskeletal pain occurred in 18% of patients and quality of life worsened with marimastat therapy. Development of this drug has also been discontinued. Several members of the non-peptidomimetics class of compounds are undergoing evaluation in Phase III studies in cancer patients. However, the majority are no longer in development because of an adverse efficacy/toxicity profile (including AG3340/Prinomastat (Agouron), BMS-275291 (Bristol-Myers-Squibb), CGS27023A/MMI270 (Novartis), Bay12-9566/Tanomastat (Bayer Inc). Neovastat/AE-941 (Aetherna Zentaris) has MMP-2, MMP-9 and VEGF inhibitory properties and is being evaluated as a potential treatment of renal carcinoma and Phase II clinical trials are underway. Some tetracycline derivatives, such as doxycycline and COL-3 have been evaluated in preclinical cancer models and G31 have entered early clinical trials in patients. Doxycycline has been shown to substantially reduce the tumor burden from breast cancer metastasis in nude mice. It exerts diverse inhibitor effects on MMP production and activity, inhibits tumor cell proliferation. However, it accumulates at high concentrations in bone, and can therefore be used for the treatment of bone metastasis. Inhibition of mitochondrial protein synthesis by doxycycline has significant anti-tumor effects in several tumor systems. Continuous doxycycline treatment combined with intermittent administration of adriamycin or 1-beta-D-arabinofuranosyl cytosine on the growth of rat leukemia resulted in the delay of tumor relapse. Treatment with zoledronic acid in combination with doxycycline may be very beneficial for breast cancer patients at risk for osteolytic bone metastasis, according to the fact that administration of a combination of zoledronic acid and doxycycline resulted in a 74% decrease in total tumor burden compared to untreated mice. In addition, doxycycline significantly enhances the tumor regression activity of cyclophosphamide, a widely used chemotherapeutic drug in neoplasias, on xenograft mice model bearing MCF-7 cells, suggesting that such combination chemotherapeutic regimen may lead to additional improvements in treatment of breast cancer. In vivo, the inhibitory effects of doxycycline on breast cancer tumor matastasis formation was potentiated by the addition of batimastat, confirming that targeting MMPs through multiple distinct pathways may improve treatment efficacy. However, in a Phase I evaluation of cancer patients, oral doses of 400 mg administered twice a day resulted in dose-limiting toxicity that consisted of fatigue, confusion, nausea, and vomiting. At the maximum tolerated dose of 300 mg twice a day, mean through plasma concentrations were comparable to those associated with antiangiogenic effect in vivo.

Nitric oxide is a gaseous molecule that is unsuitable for oral administration. However, there are several pharmacologically relevant nitric oxide-donor groups than are known to release nitric oxide in response to conditions found in the human body after administration. Exemplary nitric-donor groups are described in "Nitric Oxide Donors: For Pharmaceutical and Biological Applications"; Peng George Wang, Tingwei Bill Cai, Naoyuki Taniguchi, Wiley (2005), the contents of which are incorporated herein by reference. The effects of nitric oxide on MMPs are complex. Nitric oxide has been reported to possess inhibitory effects on MMP-9 by destabilization of MMP-9 RNA and through effects on MMP-9 activating cytokines, secondary messengers and transcription factors (AP-1). In contrast higher concentrations of nitric oxide have been shown to cause MMP activation through S-nitrosylation of an inhibitory cysteine on the prodomain.

Abbreviations: ALVDD=Asymptomatic left ventricular diastolic dysfunction, AUC=Area under the curve, cGMP=Cyclic guanosine monophosphate, DMSO=Dimethyl supfoxide, DNA=Deoxyribonucleic acid, ECM=Extracellular matrix, FCS=Fetal calf serum, HCF=Human ventricular cardiac fibroblasts, HF=Heart failure, HFpEF=Heart failure with preserved ejection fraction, IF=Interferon, iNOS=Inducible nitric oxide synthase, IQR=Interquartile range, MCP=Monocyte chemotactic protein, MMP=Matrix metalloproteinase, MRI=Magnetic resonance imaging, mRNA=messenger ribonucleic acid, NHP=Non-human primate, NO=Nitric oxide, PBMC=Peripheral blood mononuclear cells, PCR=Polymerase chain reaction, RAAS=Renin-angiotensin-aldosterone system, RNA=Ribonucleic acid, SEM=Standard error of the mean, TIMP=Tissue inhibitor of matrix metalloproteinase, TNFα=Tumor necrosis factor alpha.

SUMMARY OF THE INVENTION

According to a first aspect of the present invention, there is provided a combination of a:
  a first tetracycline (TC) component; and
  a second component capable of releasing nitric oxide (NO) or a nitrate capable of mimicking NO effects in vivo (NO mimetic)

Nitric oxide (NO) is a gaseous molecule that is unsuitable for oral administration. There are several pharmacologically relevant groups than are known to liberate nitric oxide in response to conditions found in the human body after administration or known to mimic nitric oxide's actions, for example, by stimulating cGMP production. The nitrate capable of mimicking NO effects in vivo do not necessarily release NO, but may mimic NO effects in the body with actual release of NO from the second component. For example, one simple NO mimicry effect in vivo is the activation of soluble guanyl cyclase (sGC) leading to elevated cGMP. The inventors have found that combinations of tetracyclines and nitric oxide donors or nitric oxide mimetics such as organic nitrates have favourable effects on MMP expression in vivo. It has been found that nitric oxide release or mimicry through sGC activation when combined with tetracyclines can achieve clinically relevant improvements in MMP modulation efficacy and selectivity relative to tetracyclines by themselves. The combinations of the invention advantageously act as effective MMP modulators (with inhibitory effects on MMP-2 and MMP-9, in particular), and/or modulators of inflammation mediators. Therefore, the various combinations of the invention find utility in medical applications where MMPs and/or inflammation is implicated. Included are, for example, myocardial interstitial disease, cardiac fibrosis, heart failure such as heart failure with diastolic heart failure (DHF), heart failure with preserved ejection fraction (HFpEF), congestive heart failure (CHF), asymptomatic left ventricular diastolic dysfunction (ALVDD), coronary atherosclerosis (inflammation effects), cancers (through effects on tumor angiogenesis, tumor growth and metastasis) and diabetes (inflammation effects). In addition, the combinations of the invention are useful in other inflammatory diseases or diseases associated with inflammation, including but not limited to, inflammatory bowel disease, chronic prostatitis, infections, pulmonary inflammation, osteomyelitis, renal disease, gout, arthritis and shock.

The term "combination" is intended to cover related aspects of the invention wherein (i) the first and second components are associated together through a chemical interaction, such as a covalent bond or an electrostatic interaction or a linker group to form a compound comprising both tetracycline and component capable of releasing nitric oxide (NO) or mimicking its effects (NO mimetic), or (ii) the tetracycline component and the component capable of releasing nitric oxide (NO) or NO mimetic are provided in the form of an admixture of both components, for example, in a single dosage unit; or (iii) the tetracycline component and the component capable of releasing nitric oxide (NO) or NO mimetic, are provided in the form of two or more compositions, for example, separate dosage units, suitable for administration to a patient to provide the desired therapeutic effect.

By "capable of releasing nitric oxide", it is meant the dissociation or release in vivo of a nitric oxide molecule from the compound of the invention, such that the nitric oxide component is no longer associated with, or linked to the tetracycline component or it is meant that the component can mimic NO's effects in vivo such as through activation of sGC.

By "nitric oxide releasing group" or NO mimetic, it is meant a polyatomic substance comprising at least one group capable of releasing nitric oxide or mimicking its effects. Such as group may be a nitrate ester of an alkyl alcohol (organic nitrate). Alternatively the nitric oxide donor or mimetic group may be the conjugate base of nitric acid (nitrate ion). As explained above, second component molecules comprising other nitric oxide mimetic or donor groups are also possible and include nitrate ester, diazeni- umdiolates, N-diazen-1-ium-1,2-diolate (NONOate), S-nitrosothiols, furoxan or L-arginine which is a substrate for nitric oxide synthase. Clinically used nitric oxide mimetic or donor groups that may suitably be used in the combinations of the invention include isosorbide dinitrate, isosorbide 2- and 5-mononitrate, erithrityl tetranitrate, penterithrityl tetranitrate, nicorandil, sinitrodil, glyceryl trinitrate. Preferred "nitric oxide releasing group" or NO mimetics are is arginine, a metal nitrate salt or an aza-$C_1$ to $C_5$ alkyl, aza-$C_1$ to $C_5$ alkenyl, or aza-$C_1$ to $C_5$ alkynyl groups or a hetrocyclic amine group, which is substituted with at least one NO releasing group. Preferably the "nitric oxide releasing group" or NO mimetic is nitrate. In this embodiment, the preferred nitrate esters are selected from $H_2N$-Et-$ONO_2$, $HN$-$(Et$-$ONO_2)_2$, $MeNH$-Et-$ONO_2$, $Me_2N$-Et-$ONO_2$, $H_2N$-pentyl-$ONO_2$ or $H_2N$-cyclopentyl-$ONO_2$,

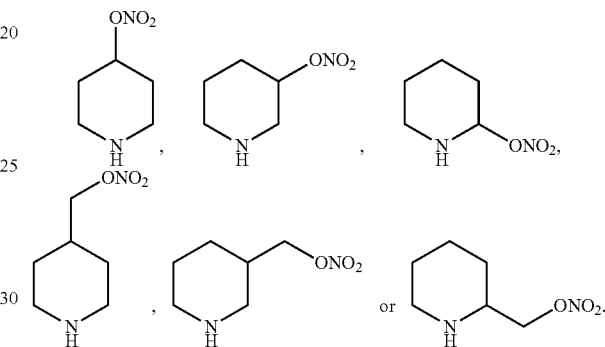

By "associated with" is meant that the tetracycline and the group or molecule capable of releasing nitric oxide (NO) are associated, or linked together by at least one chemical interaction. For example, an ionic or electrostatic interaction, a covalent or a donor bond interaction. This functional group may be involved in at least one of these types of chemical interaction with the tetracycline component either directly through covalent bonding or through electrostatic interactions, or indirectly through a linker component, such as a linker group or molecule, for example, a chemical functional group or molecule.

In a first aspect, the combination of the invention concerns a compound comprising the first and second components. In a second aspect, the combination of the invention concerns an admixture of at least one of the first and at least one of second components. In a third aspect, the combination of the invention concerns two or more separate compositions of at least one of first and at least one of the second components for administration. Accordingly, the second component may be mixed with, administered with, bonded or linked with the first tetracycline component as described above for the purposes of the combinations of the present invention.

Preferably, the combination is a compound in which the first and second components are associated together through a chemical interaction, such as a covalent bond or an electrostatic interaction or a linker group to form a compound comprising both tetracycline and component capable of releasing nitric oxide (NO) or mimicking its effects (NO mimetic).

In this embodiment, the components are associated together through a chemical interaction, such as a covalent bond or an electrostatic interaction or a linker group to form a compound comprising both tetracycline and component capable of releasing nitric oxide (NO) or mimicking its effects (NO mimetic). Suitably, the linker is a methylene (—CH$_2$—), or methylene substituted with a methyl, ethyl or propyl group (—CHMe-, —CHEt- or CHPr—).

Accordingly, in the first aspect, the compound of the invention comprises a first tetracycline component having general formula:

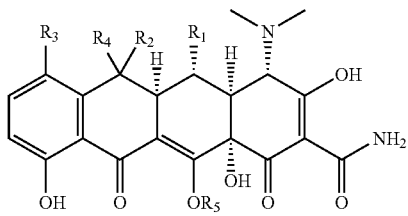

in which

R$_1$ is —H or —OH;

R$_2$ is —H, —OH or -Me;

R$_3$ is —H, or —NMe$_2$;

R$_4$ is —H, —OH or -Me; and

R$_5$ is —H or —OH. Preferably, when R$_2$ is —H or Me, R$_4$ is —OH.

Preferably, the tetracycline may be selected from the group consisting of: tetracycline, minocycline, doxycycline and oxytetracycline. The structures of these tetracyclines are:

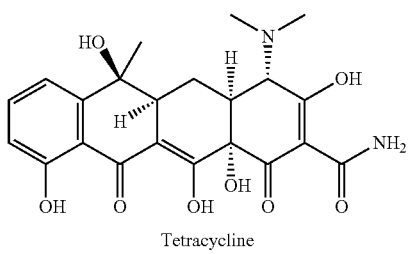

Tetracycline

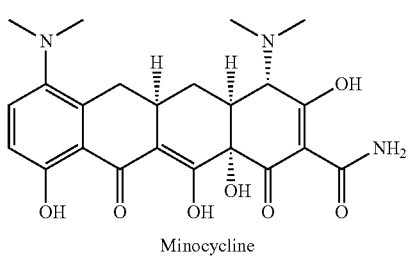

Minocycline

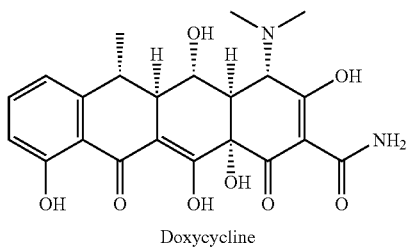

Doxycycline

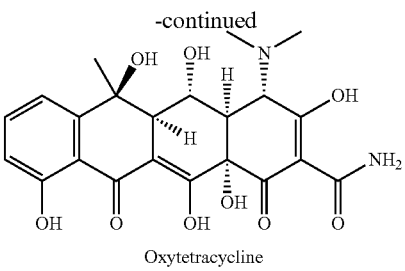

Oxytetracycline

In a particularly preferred embodiment, the tetracycline may be doxycycline, doxycycline hyclate or doxycycline hydrochloride.

In the first aspect, in which the combination of the invention concerns a compound, the second component is designated herein as the "associated molecule" or as the "second component". The second component is either capable of mimicking NO's effects in vivo, capable of releasing nitric oxide spontaneously, or is capable of releasing nitric oxide (NO) through metabolism to form nitric oxide or at least one of its redox congeners. Preferred redox congeners of nitric oxide include any reduced form of nitric oxide (NO). They may be selected from nitroxyl anion (NO$^-$), NO radical (NO.) and nitrosonium cation (NO$^+$ =N=O$^+$). The skilled person will appreciate that the form of nitric oxide redox congener produced will depend on various enzymatic or non-enzymatic metabolic pathways involved in any particular nitric acid metabolism of the compounds of the invention. Preferably, in this embodiment, the second component comprises at least one functional group comprising N(O)$_n$ which is associated with the tetracycline; wherein n is an integer selected from 1-3. Suitably, the at least one functional group comprising N(O)$_n$ is capable of releasing nitric oxide (NO) or acting as an NO mimetic. Preferably n is 3. Suitably, the second component forms at least one chemical bond with the tetracycline component of the compound of the invention. Preferable the chemical bond may be a covalent, a polar covalent bond or a donor (coordinate) bond between the first and second components. Preferably, the bond is a covalent bond. Alternatively, the second component may be associated, or linked, directly with the first tetracycline component through an electrostatic or ionic interaction.

Further alternatively, the second component may be associated, or linked, with the first tetracycline component through a linker group or molecule, which are described below in more detail.

Accordingly, in the first aspect, wherein the combination of the invention concerns a compound, the compound comprises:

a first tetracycline (TC) component; and a second component capable of releasing nitric oxide (NO) or mimicking nitric oxide (NO);

wherein the second component is ionically or covalently bonded to the first component, or is linked thereto, by means of a linker atom or molecule. Preferably, the second component is covalently bonded to the first component. More preferably still, the second component is linked to the first component by a linker atom or molecule. Preferably, the second component comprises at least one functional group having N(O)$_n$, wherein n is 3. In this embodiment, the at least one functional group comprises a nitrate anion (NO$_3^-$). Alternatively, the functional group comprises a nitrate group (—ONO$_2$). Nitrate compounds are particularly preferred because of their clinical use, stability and lipophilicity.

In a preferred embodiment of the first aspect of the invention, the compound is a tetracycline nitrate ester, in which nitrate is directly bonded to the tetracycline component. In this embodiment, the compound of the invention takes the form tetracycline (TC)—$NO_2$, where no linker group or molecule is required. For example, the compound of the invention is doxycycline nitrate, structure shown below. The skilled person will appreciate where the nitrate group can be directly bonded to the tetracycline in this embodiment.

Alternatively, the linker group may be a compound forming a Mannich base attachment to the tetracycline (TC-M-$ONO_2$). Where a linker group is used, more than one nitrate can be appended onto the linker, for example, (TC-M-$(ONO_2)_2$). Finally, the second component molecule may simply be the counter anion ($ONO_2$), wherein an ionic interaction between a cationic form of the tetracycline ($TC^+$) and the nitrate anion provides the basis for the association between the TC and second component of the compound of the invention. The Mannich base is formed by reaction of the amide group of the first tetracycline component with formaldehyde or an aldehyde to form an imine, which is subsequently reacted with an amine forming a Mannich base derivative. Alternatively the TC can be reacted with an immine formed by reacting an aldehyde with amine. In this embodiment, the compound of the invention takes the form tetracycline (TC)-M-$ONO_2$, where M represents the Mannich base attachment or the linker group created by the Mannich base attachment (for example, methylene (—$CH_2$—), or methylene substituted with a methyl, ethyl or propyl group (—CHMe-, —CHEt- or CHPr—), etc., depending on the aldehyde used in the Mannich base reaction), which leads to insertion of the linker group. The Mannich base attachment is to the primary amide of the tetracycline of the invention. The skilled person will appreciate that then, for example, an aldehyde such as paraformaldehyde is used to form the Mannich base linkage, the reaction inserts a methylene group between the first and second components of the compound of the invention. This methylene group then serves as a linker associating the first and second components together by covalent bonding. Different types of methylene linkers with different substitutions may be used by selection of appropriate aldehyde.

Accordingly, in a second embodiment of the first aspect, wherein the combination of the invention concerns a compound, the second component comprises:

(i) a short chain aza-alkyl ($C_1$ to $C_5$), aza-alkenyl ($C_1$ to $C_5$), or aza-alkynyl ($C_1$ to $C_5$) group, which can be linear, branched, or cyclic; and (ii) at least one nitric oxide donor group or NO mimetic selected from a nitrate ester, diazeniumdiolates a N-diazen-1-ium-1,2-diolate (NONOate), S-nitrosothiols, furoxan or a molecule capable of releasing nitric oxide (NO), such as arginine or similar nitric oxide releasing moiety or mimetic.

In this embodiment, the second component may be bonded or linked to the first tetracycline component through its primary amide by a covalent bond giving a compound with general structure:

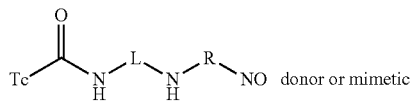

in which R is one of the aza-alkyl ($C_1$ to $C_5$), aza-alkenyl ($C_1$ to $C_5$), or aza-alkynyl ($C_1$ to $C_5$) groups or fragments described above, Tc is the first tetracycline component, and L is a methylene linker, which can be unsubstituted (—$CH_2$—) or substituted with a methyl, ethyl or propyl group (—CHMe-, —CHEt- or CHPr—). The substitution on the methylene linker depends on the aldehyde used in the Mannich base reaction. Examples of the second compound include nitrated aza-alkyl, nitrated aza-alkenyl, or nitrated aza-alkynyl groups In a second embodiment of the first aspect of the invention, the second component comprises:

(i) a short chain aza-alkyl ($C_1$ to $C_5$), aza-alkenyl ($C_1$ to $C_5$), or aza-alkynyl ($C_1$ to $C_5$) group or fragment, which can be linear, branched, or cyclic, and which can be substituted or unsubstituted; and (ii) at least one nitric oxide donor or mimetic group or at least one group comprising $N(O)_n$, wherein n is an integer selected from 1-3, as defined above, hereinafter referred to as a "nitric-oxide donor group".

Examples of the second component include aza-($C_1$ to $C_5$)alkyl, aza-($C_1$ to $C_5$)alkenyl aza-($C_1$ to $C_5$)alkynyl group or fragment which is substituted with at least one nitrate. Preferred examples of the second component include nitrated aza-alkyl, wherein the second component is a nitrated $C_1$ to $C_5$ alkyl amine, more preferably, a nitrated $C_1$ to $C_2$ alkyl amine. Preferably, the nitrated aza-alkenyl is a nitrated $C_1$ to $C_5$ alkenyl amine, more preferably a nitrated $C_1$ to $C_2$ alkenyl amine. Preferably, the nitrated aza-alkynyl group is a nitrated $C_1$ to $C_5$ alkynl amine, more preferably a nitrated $C_1$ to $C_2$ alkynl amine. Preferred examples of the second component comprises a short chain aza-alkyl (alkyl amine) molecule $H_2N$—R, in which R is a $C_1$-$C_5$ alkyl group, more preferably a $C_1$-$C_2$ alkyl group. Preferably, the nitric oxide donor or mimetic group is —$ONO_2$. Examples of the second component are be $H_2N$—R—$N(O)_n$, in which R is a $C_1$-$C_5$ alkyl, alkenyl or alkenyl more preferably a $C_1$-$C_2$ alkyl alkyl, alkenyl or alkenyl. The nitric oxide donor or mimetic group in this example is preferably —$ONO_2$.

In this embodiment, the second component is linked to the first tetracycline component by a Mannich base attachment through a linker L to the amide group of the first tetracycline component, giving a compound with general structure:

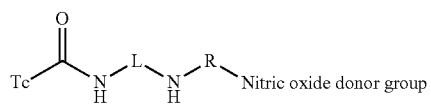

in which R is a aza-alkyl ($C_1$ to $C_5$), aza-alkenyl ($C_1$ to $C_5$), or aza-alkynyl ($C_1$ to $C_5$) group or fragment, Tc is the first tetracycline component, and L is a methylene linker, which can be unsubstituted methylene (—$CH_2$—) or substituted with a methyl, ethyl or propyl group (—CHMe-, —CHEt- or CHPr—).

In a third embodiment of the first aspect of the invention, the second component may be linked to the first tetracycline component by a Mannich base attachment through a linker group L to the amide group of the first tetracycline component, forming a compound with general structure:

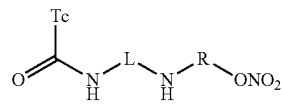

wherein R is an aza-alkyl ($C_1$ to $C_5$), aza-alkenyl ($C_1$ to $C_5$), or aza-alkynyl ($C_1$ to $C_5$) group or fragment, Tc is the first tetracycline component, and L is a methylene linker. The methylene linker may be unsubstituted (—$CH_2$—) or substituted with a methyl, ethyl or propyl group (—CHMe-, —CHEt- or CHPr—). The substitution depends on the aldehyde used in the Mannich base reaction.

In a fourth embodiment of the first aspect of the invention, the second component comprises:

(i) an aza-ethyl molecule (ethyl amine, $EtNH_2$); and (ii) at least one nitrate (—$ONO_2$) group.

Typical examples of second component molecules are $H_2$N-Et-$ONO_2$.

In this embodiment, the second component is linked to the first tetracycline component by a Mannich base attachment through a linker L to the amide group of the first tetracycline component, forming a compound with general structure:

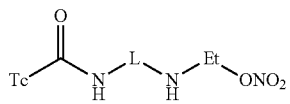

in which Tc is the first tetracycline component, and L is a methylene linker. The methylene linker may be unsubstituted (—$CH_2$—) or substituted with a methyl, ethyl or propyl group (—CHMe-, —CHEt- or CHPr—).

In a preferred fifth embodiment of the first aspect, the second component comprises:

(i) an aza-dimethylethyl molecule (dimethylethyl amine, $Me_2$NEt); and (ii) at least one nitrate (—$ONO_2$) group Typical examples of second component molecules in this example take the form $Me_2$N-Et-$ONO_2$.

In this embodiment, the second component is linked to the first tetracycline component by a Mannich base attachment through a linker L to the amide group of the first tetracycline component, forming a compound with general structure:

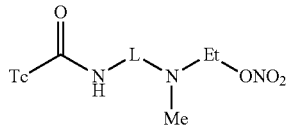

in which Tc is the first tetracycline component, and L is a methylene linker, which can be unsubstituted (—$CH_2$—) or substituted with a methyl, ethyl or propyl group (—CHMe-, —CHEt- or CHPr—).

In a preferred sixth embodiment of the first aspect, the second component comprises:

(i) an aza-diethyl molecule (diethyl amine, EtNHEt); and (ii) at least one nitric oxide releasing or NO mimetic.

Typical examples of second components in this embodiment take the form EtHN-Et-N(O)$_n$, wherein n=1 to 3. Preferably n=3.

In this embodiment, the second component is linked to the first tetracycline component by a Mannich base attachment through a linker L to the amide group of the first tetracycline component, forming a compound with general structure:

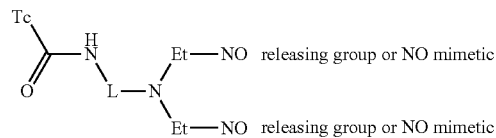

in which Tc is the first tetracycline component, and L is a methylene linker, which can be unsubstituted (—$CH_2$—) or substituted with a methyl, ethyl or propyl group (—CHMe-, —CHEt- or CHPr—). The linker substituent depends on the aldehyde used in the Mannich base reaction.

In a preferred seventh embodiment of the first aspect, the second component comprises an aza-diethyl molecule (diethyl amine, EtNHEt or diethyl methylamine EtNMeEt) and two nitrate groups, wherein one nitrate group (—$ONO_2$) is attached to each ethyl group. Typical examples of second components in this example take the form HN-(Et-$ONO_2$)$_2$. Accordingly, in such embodiments, the second component capable of releasing nitric oxide (NO) having the at least one nitric oxide donor group is N,N-di-ethylnitrate amine.

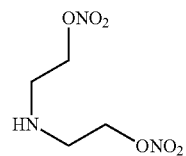

In this embodiment, the second component is linked to the first tetracycline component by a Mannich base attachment through a linker L to the amide group of the first tetracycline component, forming a compound with general structure:

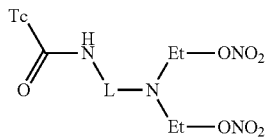

in which Tc is the first tetracycline component, and L is a methylene linker, which can be unsubstituted (—$CH_2$—) or substituted with a methyl, ethyl or propyl group (—CHMe-, —CHEt- or CHPr—). The substituent depends on the aldehyde used in the Mannich base reaction.

In a preferred eight embodiment of the first aspect, the second component comprises:

(i) an aza-pentyl molecule (pentyl amine, pentyl-$NH_2$) or an aza-cyclo-pentyl molecule; and (ii) at least one at least one nitrate (—$ONO_2$) group.

Typical examples of second components in this example take the form $H_2$N-pentyl-$ONO_2$ or $H_2$N-cyclopentyl-$ONO_2$. The second component is covalently bonded or linked to the first tetracycline component through the Mannich base attachment described above.

In a preferred ninth embodiment of the first aspect of the invention, the second component comprises a heterocyclic amine, which can be substituted or unsubstituted. Suitably, the nitric oxide releasing group or the NO mimetic can be linked to the heterocyclic amine at the 2, 3, or 4 positions. Preferably, the heterocyclic amine may be selected from piperidine, piperazine or pyrrolidine. The heterocyclic amine may be substituted with a direct —$ONO_2$ group or a linker-ONO$_2$, wherein the linker is a C$_1$-C$_5$ alkyl group or more preferably a C$_1$-C$_2$ alkyl group.

In a preferred tenth embodiment of the first aspect of the invention, the second component comprises:

(i) a piperidine molecule; and (ii) at least one at least one nitrate (—ONO$_2$) group.

Examples of the second component include:

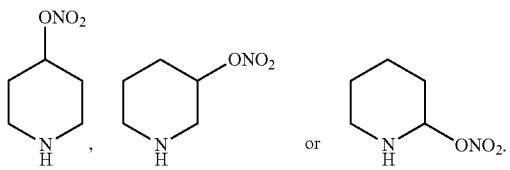

In this embodiment, the second component is linked to the first tetracycline component by a Mannich base attachment through a linker L to the amide group of the first tetracycline component, forming a compound with general structure:

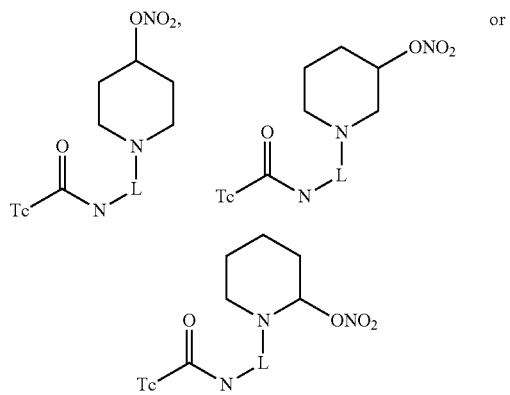

in which, Tc is the first tetracycline component, and L is a methylene linker, which can be unsubstituted (—CH$_2$—) or substituted with a methyl, ethyl or propyl group (—CHMe-, —CHEt- or CHPr—).

In a preferred eleventh embodiment, the second component comprises a combination of:

(i) a piperidine molecule; and (ii) at least one at least one alkyl-nitrate (R—ONO$_2$) group, in which R is a C$_1$-C$_5$ alkylene group. More preferably R is a C$_1$ to C$_2$ alkylene group. Most preferably, the R group is a methylene (—CH$_2$—) group. The skilled person will appreciate that the alkyl nitrate group may be substituted at the 2, 3 or 4 position of the piperidine ring. Preferably, the at least one alkyl nitrate group (-alkyl-ONO$_2$) is at the 3 position of the ring.

In this embodiment, the second component is linked to the first tetracycline component by a Mannich base attachment through a linker L to the amide group of the first tetracycline component, forming a compound with general structure:

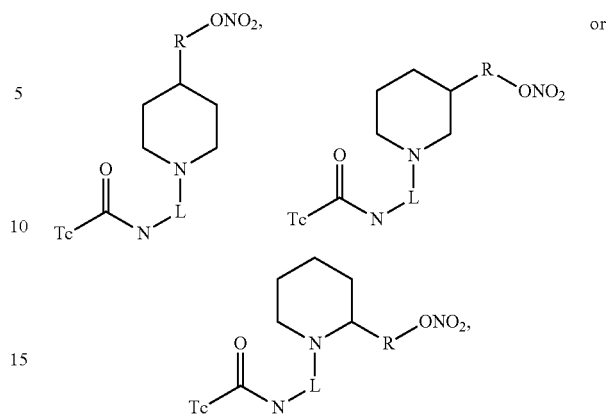

in which Tc is the first tetracycline component, L is a methylene linker, which can be unsubstituted (—CH$_2$—) or substituted with a methyl, ethyl or propyl group (—CHMe-, —CHEt- or CHPr—), and R is a C$_1$-C$_5$ alkylene group. More preferably R is C$_1$ to C$_2$ alkylene group. Most preferably, R is methylene.

In a preferred twelfth embodiment, the second component comprises:

(i) a piperidine molecule; and (ii) at least one at least one —CH$_2$ONO$_2$ group Suitably, the methyl-nitrate groups can be linked at the 2, 3, or 4 ring positions. Position 3 is the most preferred position. Typical examples of second component molecules in this example include:

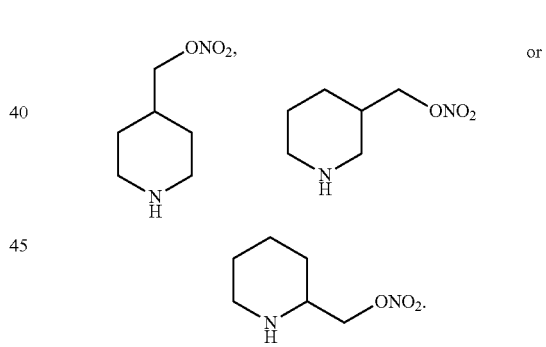

In this embodiment, the second component is linked to the first tetracycline component by a Mannich base attachment through a linker L to the amide group of the first tetracycline component, forming compound with general structure:

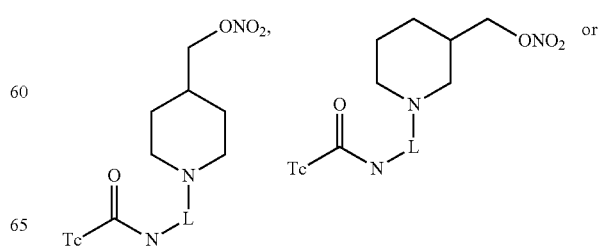

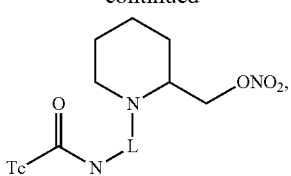

in which, Tc is the first tetracycline component, L is a methylene linker, which can be unsubstituted (—CH₂—) or substituted with a methyl, ethyl or propyl group (—CHMe-, —CHEt- or CHPr—).

In a preferred thirteenth embodiment, the second component is a nitrate anion. The nitrate anion is involved in at least one ionic or electrostatic interaction with the tetracycline component. In an example of this embodiment, the second component may be metal nitrate salt. Preferably, the nitrate salt is silver nitrate. Silver nitrate forms a nitrate ionic salt with the tetracycline (TC⁺NO₃⁻). Typically, a nitrate salt can be formed by reaction of the TC hydrochloride with AgNO₃, for example.

The preferred compounds of the invention may be selected from:

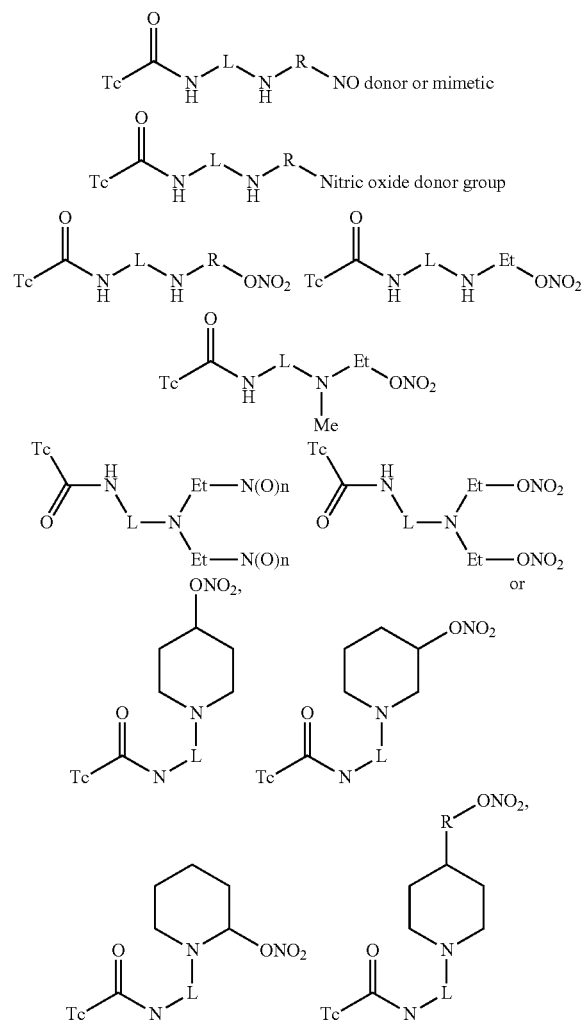

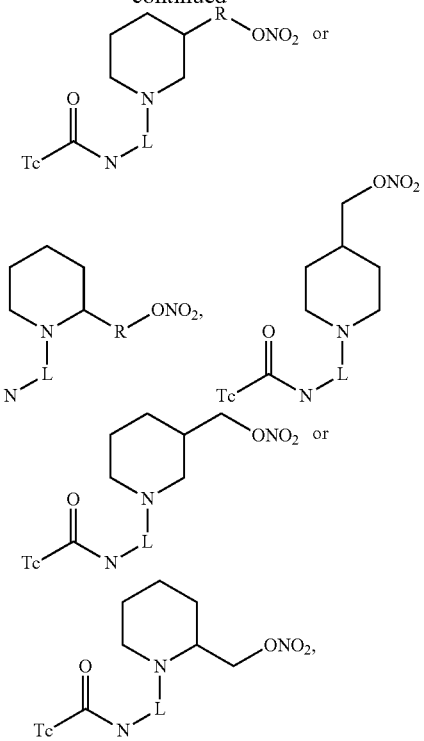

wherein linker L is a methylene (—CH₂—), or methylene substituted with a methyl, ethyl or propyl group (—CHMe-, —CHEt- or CHPr—), R is a $C_1$-$C_5$ alkylene group.

In a preferred fourteenth embodiment of the first aspect of the invention, the second component may comprise arginine. Preferably, the second component molecule is L-arginine. L-arginine is a substrate for nitric oxide synthase (NOS) and its metabolites include nitric oxide (NO). Suitably, the L-arginine may be linked to the first tetracycline component through a linker group or molecule as described above.

In a preferred fifteenth embodiment of the first aspect of the invention, the compound may be selected from the group consisting of:

6-deoxy-5-oxytetracycline nitrate salt;

doxycycline-5-nitrate

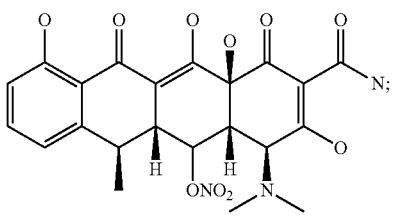

doxycycline-12a-nitrate;

minocycline-12a-nitrate;

amido-N-[3-methylnitratepiperidinomethyl]-α-6-deoxy-5-oxytetracycline;

amido-N—[N,N-diethylnitrate-aminomethyl]-α-6-deoxy-5-oxytetracycline (amido-N—[bis-(β-nitrooxyethyl)aminomethyl]-α-6-deoxy-5-oxytetracycline)

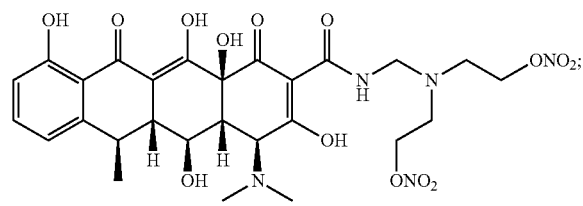

amido-N-[(3-nitrooxyethyl)aminomethyl]-α-6-deoxy-5-oxytetracycline

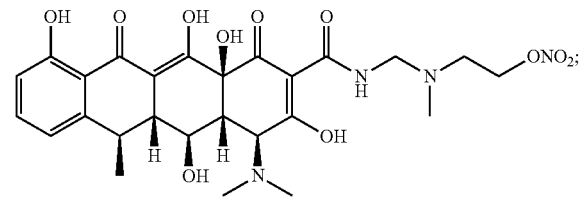

amido-N-[3-(nitrooxymethyl)piperidinomethyl]-α-6-deoxy-5-oxytetracycline

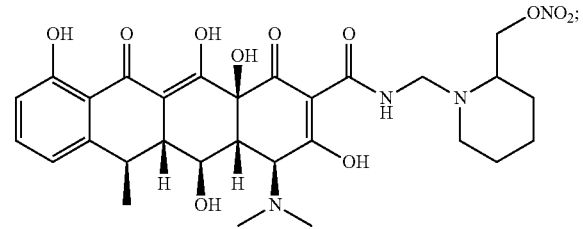

amido-N-[3-(nitrooxymethyl)piperidinomethyl]-α-6-deoxy-5-oxytetracycline

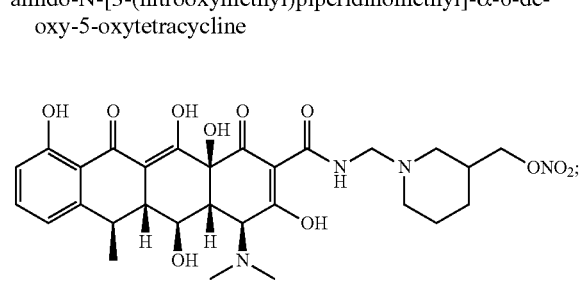

amido-N-[4-(nitrooxymethyl)piperidinomethyl]-α-6-deoxy-5-oxytetracycline

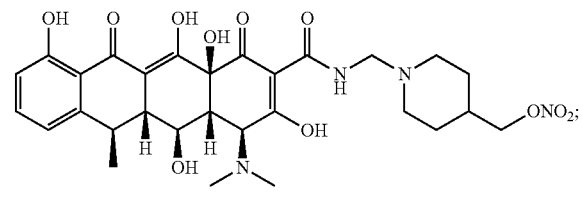

amido-N-[4-nitrooxypiperidinomethyl]-α-6-deoxy-5-oxytetracycline

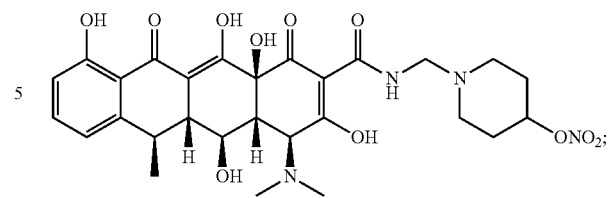

amido-N-[4-nitrooxypiperidinomethyl]-tetracycline

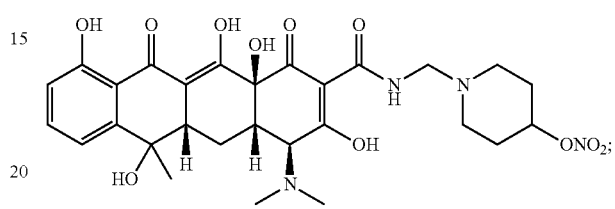

amido-N—[bis-(β-nitrooxyethyl)methylaminomethyl]-α-6-deoxy-5-oxytetracycline

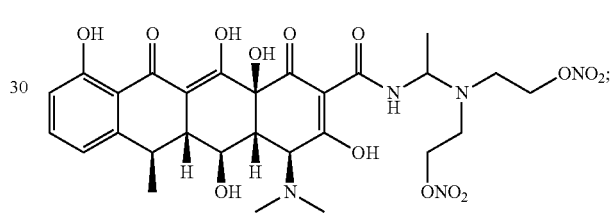

amido-N—[bis-(β-nitrooxyethyl)methylaminomethyl]-α-6-deoxy-5-oxytetracycline

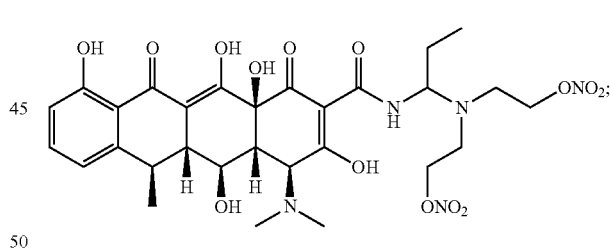

amido-N—[bis-(β-nitrooxyethyl)ethylaminomethyl]-tetracycline

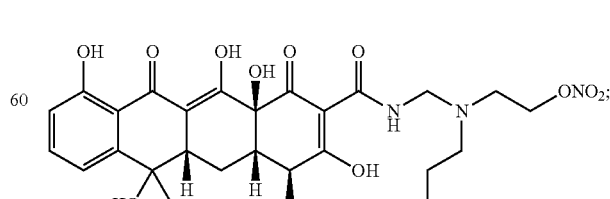

amido-N-[(β-nitrooxyethyl)aminomethyl]-tetracycline

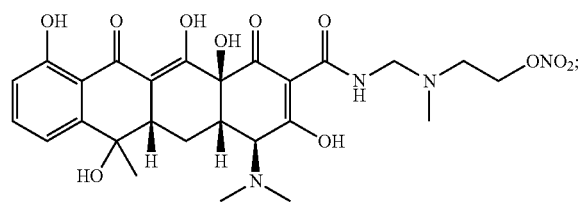

amido-N-[4-(nitrooxymethyl)piperidinomethyl]-tetracycline

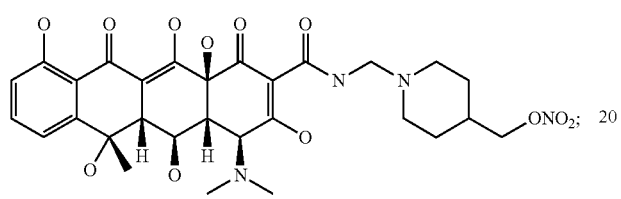

amido-N-[3-(nitrooxymethyl)piperidinomethyl]-tetracycline

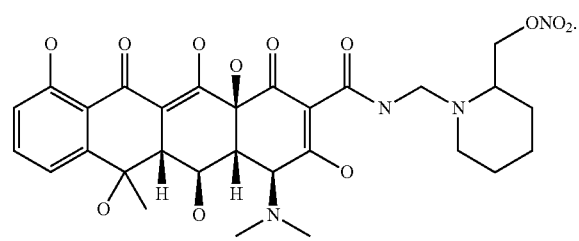

In the second aspect of the invention, the combination of the invention may be provided as an admixture of the first and second components of the invention. An admixture means a mixture the components where they are not chemically bonded or associated together on a molecular level. Preferably, in this aspect, at least one of the first tetracycline components described above may be mixed with at least one of the second components examples described above to form an admixture.

In the third aspect of the invention, the combination of the invention may be provided in the form of two or more separate compositions of at least one tetracycline and at least one second component capable of releasing NO or otherwise mimicking the effect of NO in vivo, for administration to a patient to provide the desired therapeutic effect achieved by the admixtures or compound of the invention.

Examples of the second components of the invention include aza-alkyl, aza-alkenyl, or aza-alkynyl groups which are substituted with at least one NO releasing group, as defined above. Preferably, the NO releasing group is a nitrate group. Preferably, the nitrated aza-alkyl, comprises a $C_1$ to $C_5$ alkyl, more preferably, a $C_1$ to $C_2$ alkyl group. Preferably, the nitrated aza-alkenyl comprises a $C_1$ to $C_5$ alkenyl, more preferably a $C_1$ to $C_2$ alkenyl group. Preferably, the nitrated aza-alkynyl comprises a $C_1$ to $C_5$ alkynl, more preferably a $C_1$ to $C_2$ alkynl group. Examples of the second component include $H_2N-R-N(O)_n$, in which R is a $C_1$-$C_5$ alkyl, alkenyl or alkenyl, more preferably a $C_1$-$C_2$ alkyl alkyl, alkenyl or alkenyl group. The nitric oxide donor group in this example is preferably —$ONO_2$. Typical examples of second component molecules are $H_2N$-Et-$ONO_2$, HN-(Et-$ONO_2)_2$, MeNH-Et-$ONO_2$, $Me_2N$-Et-$ONO_2$, $H_2N$-pentyl-$ONO_2$ or $H_2N$-cyclopentyl-$ONO_2$. Further examples of second components include:

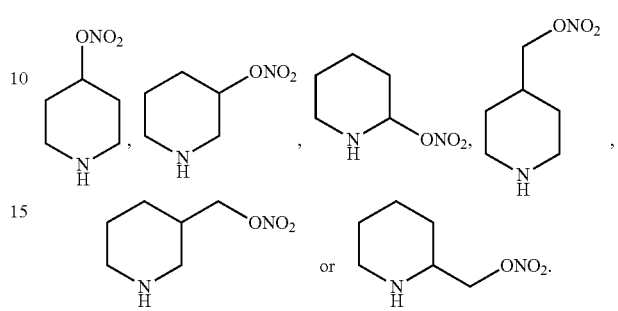

Suitably, the second component may be metal nitrate salt. Preferably, the nitrate salt is silver nitrate. Alternatively, the second component molecule may be L-arginine. Clinically used nitric oxide mimetic or donor groups which may be used as second components within the various aspect of the invention and include isosorbide dinitrate, isosorbide 2- and 5-mononitrate, erithrityl tetranitrate, penterithrityl tetranitrate, nicorandil, sinitrodil, glyceryl trinitrate. These clinically used nitrates are particularly preferred in the admixtures aspect of the invention.

According to a fourth aspect of the present invention, there is provided a method of preparing an admixture comprising the step of:
(i) mixing together a first tetracycline component, and
(ii) a second component capable of releasing nitric oxide (NO) or capable of otherwise mincking NO in vivo.

According to a fifth aspect of the present invention, there is provided a method of preparing a compound of the invention, the method comprising the step of:
(i) reacting together a first tetracycline component, and
(ii) a second component capable of releasing nitric oxide (NO) or acting as an NO mimetic,
such that the second component becomes ionically or covalently bonded to the first component, or linked thereto, by means of a linker atom or molecule. In other words, the first tetracycline component becomes associated or linked with the molecule that is capable of releasing nitric oxide (NO) or mimicking its effects.

Preferably, the method comprises reacting a second component compound having at least one functional group comprising $N(O)_n$, wherein n is from 1 to 3, with a first tetracycline component, such that the tetracycline component becomes associated or linked with the compound having at least one functional group comprising $N(O)_n$. It will be appreciated that the second component is capable of releasing nitric oxide (NO).

The skilled person will appreciate that the second component that is capable of releasing nitric oxide (NO) may be involved in at least one type of chemical interaction with the first tetracycline component either directly through covalent bonding or through electrostatic interactions, or indirectly through a linker, such as a chemical functional group or molecule.

In a preferred embodiment, the second component reacts with the first tetracycline component to form a Mannich base link with the tetracycline primary amide. It will be appreciated that this reaction occurs under conditions allowing Mannich base formation. Accordingly, in preferred embodiment, the reaction of the first and second components of the compound of the invention occurs in the presence of an aldehyde. Preferably, the aldehyde is formaldehyde. More preferably still, the aldehyde is paraformaldehyde, which, in the Mannich base attachments results in insertion of a methylene group between the first and second components.

In a preferred embodiment of the method of preparing the compound of the invention, the second component molecule is provided in solution. Suitably, the second component is provided in solution with an alcohol. Preferably, the second component is provided in a secondary alcohol, for example, isopropyl alcohol.

The second component is provided in solution with a secondary alcohol by heating to a temperature of 65-85° C., preferably 75° C. The second component provided in solution with a secondary alcohol is then reacted with the first component at a temperature of 30-50° C., preferably 40° C.

Suitably, the first tetracycline component is provided in solution with an alcohol, an ether or a nitrile. Preferably, the alcohol may be selected from methanol, isopropyl alcohol, or a mixture thereof. Preferably, the ether is a polar ether, for example, tetrahydrofuran (THF). Preferably, the nitrile is acetonitrile.

It will be appreciated that the first tetracycline (TC) component and the second component of the compound of the invention can be any of the tetracylines or second component molecules described herein. However, in a preferred embodiment, the tetracycline component is doxycycline. The preferred second component molecule is N,N-diethylnitrate amine.

The solution of the tetracycline component and the solution of the second component are mixed to start the reaction. Preferably, the mixture of the tetracycline and the second component proceeds under constant stirring. Suitably, the reaction is conducted at a temperature of 20-50° C. Preferably, the reaction is conducted at a temperature of 20° C. Alternatively, the reaction is conducted at a temperature of 40° C. The reactants may be stir to facilitate reaction for from about 0.5 to about 18 hours. Preferable, the reaction is conducted for at least 0.5 hour. Alternatively, the reaction is conducted for at least 2 hours. Further alternatively, the reaction is conducted for at least 16 hours. The skilled person will appreciate the time necessary for completion of reaction will depend on the nature of the specific tetracycline component, the second component, their solubilities in the solvents of choice.

In a preferred embodiment, the method of preparing a compound according to the first aspect of the present invention comprises the step of reacting a nitrate-containing group with tetracycline, optionally in the presence of an aldehyde forming a Mannich base with the tetracycline primary amide.

Preferably, the aldehyde is formaldehyde. Further preferably, the aldehyde is paraformaldehyde.

Alternatively, the at least one nitrate-containing group comprises a metal nitrate. Optionally, the at least one nitrate-containing group comprises silver nitrate.

According to a sixth aspect of the present invention, there is provided a pharmaceutical composition comprising a combination of a:
a first tetracycline (TC) component; and
a second component capable of releasing nitric oxide (NO);
wherein the second component is combined with the first tetracycline component.

The term "combined" is intended to cover embodiments wherein (i) the first and second components are associated together through an interaction of the types described below to form a compound comprising both tetracycline and component capable of releasing nitric oxide (NO), and (ii) the tetracycline component and the component capable of releasing nitric oxide (NO) are provided in the form of an admixture of both components, for example, in a single dosage unit; and (iii) the tetracycline component and the component capable of releasing nitric oxide (NO) are provided in the form of two or more separate dosage units for substantially simultaneously administration to a patient.

Accordingly, in a preferred embodiment, the pharmaceutical composition comprises an admixture of the first tetracycline (TC) component; and the second component capable of releasing nitric oxide (NO). In a particularly preferred embodiment, the pharmaceutical composition comprises a compound of the invention.

According to a seventh aspect of the present invention, there is provided a method of treating a disease or condition by administering a therapeutically effective amount of the combination of the invention, wherein the combination comprises:
a first tetracycline (TC) component; and
a second component capable of releasing nitric oxide (NO);
wherein the second component is combined with the first tetracycline component.

Suitably, the method of treating a disease or condition comprises administering a therapeutically effective amount of the combination of the invention to a patient in need thereof. The combination may be administered by providing the patient with a therapeutically effective amount of the compounds described herein. Alternatively, the combination may be administered by providing the patient with a therapeutically effective amount of an admixture of the first tetracycline component and the second component capable of releasing nitric oxide (NO). Alternatively still, the combination may be administered by providing the patient with a therapeutically effective amount of the first and second components by co-administering the tetracycline and the second component capable of releasing nitric oxide (NO), as part of a suitable dosage regimen.

Accordingly, the combinations, the compound or the pharmaceutical compositions of the invention may be used in the medical field. More suitably, the combinations or the compounds of the invention or the pharmaceutical compositions comprising the combination or the compound of the invention can be used in the medical field. The combination, the compound or the pharmaceutical composition of the invention may be used as a medicament or may be used in the manufacture of a medicament for the treatment of, alleviation of, and/or prevention of a disease. In a particularly preferred embodiment, the combination, the compound or the pharmaceutical composition of the invention may be used in the treatment or prevention of inflammatory and/or cardiovascular diseases selected from the group consisting of: myocardial interstitial disease, cardiac fibrosis, heart failure such as heart failure with diastolic heart failure (DHF), heart failure with preserved ejection fraction (HFpEF), congestive heart failure (CHF), asymptomatic left ventricular diastolic dysfunction (ALVDD), coronary atherosclerosis (inflammation effects), cancers (through effects on tumor angiogenesis, tumor growth and metastasis) and diabetes (inflammation effects), inflammatory bowel disease, chronic prostatitis, infections, pulmonary inflammation, osteomyelitis, renal disease, gout, arthritis and shock.

With regard to the admixtures combination aspect of the invention. Admixture of doxycycline and nitrate A (diethanolamine dinitrate), in particular, can be used to treat invasive bladder cancer, chronic prostatitis, acute pyelpnephritis, non-Hodgkins lymphoma, pulmonary infections and osteomyelitis through the effect on IL8. Whereas, an admixture of doxycycline and nitrate A (Diethanolamine dinitrate), in particular, can be used to treat inflammatory bowel disease through effects on IL4. Furthermore, admixtures of doxycycline and nitrate A (Diethanolamine dinitrate) can be used to treat fever, anemia, cryopyrinopathies (hereditary periodic fever syndromes), gout and pseudogout, Septic shock (IL-1β). Alternatively, admixtures of doxycycline and nitrate B (Nitroxymethyl piperidine) can be used to treat fever, anemia, cryopyrinopathies (hereditary periodic fever syndromes), gout and pseudogout, Septic shock (IL-1β). However, admixtures of doxycycline and nitrate A (Diethanolamine dinitrate) are preferred in treating these particular conditions.

With regard to use of the compounds of the invention, preferably, the disease is a cardiovascular disease, such as heart failure. In a particularly preferred embodiment, the combination, the compound or the pharmaceutical composition of the invention is used in treatment or prevention of heart failure caused by or associated with diastolic dysfunction.

In a preferred embodiment, the combinations, the compounds or the pharmaceutical compositions of the invention may be used in the treatment of cancer. Suitably, the cancer may be at least one of the group consisting of: bone metastasis, breast cancer, pancreatic cancer, lung cancer, bladder cancer, colorectal cancer, ovarian cancer, prostate cancer, gallbladder cancer or cancerous brain tumors. Suitably, the cancer is breast or colorectal cancer. The combinations and compounds described herein may be used in conjunction with other drug actives or therapeutic agents known to the skilled person. The other therapeutic agent can provide additive or synergistic value relative to the administration of the combination or the compound of the invention alone, and may be selected from lipid-lowering agents that reduce blood levels of cholesterol and trigylcerides, agents that normalize blood pressure, agents, such as aspirin or platelet ADP receptor antatoginist (e.g., clopidogrel and ticlopidine), that prevent activation of platelets and decrease vascular inflammation, and pleotrophic agents such as peroxisome proliferator activated receptor (PPAR) agonists, with broad-ranging metabolic effects that reduce inflammation, promote insulin sensitization, improve vascular function, and correct lipid abnormalities. Further advantages may arises from combination with another therapeutic agent for cardiovascular disease. Examples of such agents include, but are not limited to an anti-inflammatory agent, an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, and/or combinations thereof. Antiinflammatory agents include immunosuppressants, TNF inhibitors, corticosteroids, non-steroidal anti-inflammatory drugs (NSAIDs), disease-modifying anti-rheumatic drugs (DMARDS), and the like. Exemplary antiinflammatory agents include, for example, prednisone; methylprenisoione (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine. The additional therapeutic may be a chemotherapeutic drugs or anti-proliferative agent selected from alkylating agents, antimetabolites, anthracyclines, plant alkaloids, topoisomerase inhibitors, or other antitumour agents, monoclonal antibodies, tyrosine kinase inhibitors, hormones. Exemplary anti-proliferative agents include vinca alkaloids (e.g. vinblastine), the anthracyclines (e.g. adriamycin), the epipodophyllotoxins (e.g. etoposide), antibiotics (e.g. actinomycin D and gramicidin D), antimicrotubule drugs (e.g. colchicine), protein synthesis inhibitors (e.g. puromycin), toxic peptides (e.g. valinomycin), topoisomerase I inhibitors (e.g. topotecan), DNA intercalators (e.g. ethidium bromide), anti-mitotics, vinca alkaloids (e.g. vinblastine, vincristine, vindesine and vinorelbine), epothilones (e.g. epothilone A, epothilone B and discodermolide), nocodazole, colchicine, colchicine derivatives, allocolchicine, Halichondrin B, dolstatin 10, maytansine, rhizoxin, thiocolchicine, trityl cysterin, estramustine, nocodazole, platinum-based agents (e.g. cisplatin, paraplatin, carboplatin, but not the subject platinum-based chemotherapeutic agents as defined herein), camptothecin, 9-nitrocamptothecin (e.g. Orethecin, rubitecan), 9-aminocamptothecin (IDEC-13'), exatecan (e.g. DX-8951f), lurtotecan (GI-147211 C), BAY 38-3441, the homocamptothecins such as diflomotecan (BN-80915) and BN-80927, topotecan (Hycamptin), NB-506, J107088, pyrazolo[1,5-a]indole derivatives, such as GS-5, lamellarin D, irinotecan (Camptosar, CPT-11), and antibodies, such as 1 D1 0, Hu1D10, 1 D09C3, 1C7277, 305D3, rituximab, 4D5, Mab225, C225, Daclizumab (Zenapax), Antegren, CDP 870, CMB-401, MDX-33, MDX-220, MDX-477, CEA-CIDE, AHM, Vitaxin, 3622W94, Therex, 5G1.1, IDEC-131, HU-901, Mylotarg, Zamyl (SMART M195), MDX-210, Humicade, LymphoCIDE, ABX-EGF, 17-1A, Epratuzumab, Cetuximab (Erbitux), Pertuzumab (Omnitarg, 2C4), R3, CDP860, Bevacizumab (Avastin), tositumomab (Bexxar), Ibritumomab tiuxetan (Zevalin), M195, 1D10, Hu1D10 (Remitogen, apolizumab), Danton/DN1924, an "HD" antibody such as HD4 or HD8, CAMPATH-1 and CAMPATH-1H or other variants, fragments, conjugates, derivatives and modifications thereof, or other equivalent compositions with improved or optimized properties.

For example, it is known in the art that doxycycline with zoledronic acid is useful in breast cancer treatment. Adriamycine and 1-beta-D-arabinofuranosykl cytoside combinations are useful in delay of tumor relapse. Combination with cyclophosphamide may also be useful in chemotherapy.

In a eighth aspect of the invention, the combinations or the compounds described herein may be used in a screening method to identify further compounds having benefits in the disease states mentioned above. In a ninth aspect, the combinations or the compounds described herein may be used in determining the suitable of the combination and/or the compounds of the invention for the treatment the disease states mentioned herein.

Further Definitions For the purposes of this specification, in the case of a polyatomic molecule represented by text, a single bond extending between any two atoms is represented by a solid dashed line (—), a double bond extending between any two atoms is represented by a double solid dashed line (=), and a triple bond extending between any two atoms is represented by a triple solid dashed line (≡), unless otherwise stated. By "short chain" is meant a polyatomic molecule comprising at least one carbon atom. Optionally, the polyatomic molecule comprises 1-6 carbon atoms. Further optionally, the polyatomic molecule comprises 1-3 carbon atoms. By the term "linear" is meant a molecule comprising at least two atoms, any of which can be the same or different, wherein each atom of the molecule is bonded to an adjacent atom in a substantially straight series. Each atom can be bonded to an adjacent carbon atom by a single-, double-, triple-, or higher order-bond. By the term "branched" is meant a molecule comprising at least three atoms, any of which can be the same or different, bonded in a substantially straight series, wherein the molecule further comprises at least one other atom, which is not bonded to either of the terminal atoms of the substantially straight series. Each atom can be bonded to an adjacent atom by a single-, double-, triple-, or higher order-bond. By "tetracycline" it is meant, the compound (4S,4aS,5aS,6S,12aS)-4-(dimethylamino)-3,6,10,12,12a-pentahydroxy-6-methyl-1,11-dioxo-4,4a,5,5a-tetrahydrotetracene-2-carboxamide. By "minocycline" it is meant, the compound (4S,4aS,5aR,12aS)-4,7-bis(dimethylamino)-3,10,12,12a-tetrahydroxy-1,11-dioxo-4a,5,5a,6-tetrahydro-4H-tetracene-2-carboxamide. By "doxycycline" is meant the compound (4S,4aR,5S,5aR,6R,12aS)-4-(dimethylamino)-3,5,10,12,12a-pentahydroxy-6-methyl-1,11-dioxo-1,4,4a,5,5a,6,11,12a-octahydrotetracene-2-carboxamide. By "oxytetracycline" it is meant, the compound (4S,4aR,5S,5aR,6S,12aS)-4-(dimethylamino)-3,5,6,10,12,12a-hexahydroxy-6-methyl-1,11-dioxo-4,4a,5,5a-tetrahydrotetracene-). In a further aspect, there is provided a combination, compound, composition or use substantially as described herein with reference to the accompanying figures and examples. There is provided a compound comprising a tetracycline, and at least one functional group comprising N(O)n associated with the tetracycline; wherein n is an integer selected from 1-3. Optionally, n is 1. Further optionally, the at least one functional group comprises NO. Still further optionally, the at least one functional group comprises a nitroso group (—N=O). Alternatively, the at least one functional group comprises NO and is selected from a diazeniumdiolate molecule; a NONOate molecule ($R_1R_2N$—(NO—)—N=O; wherein $R_1$ and $R_2$ are each independently selected from alkyl groups); and a thionitrite molecule (—SNO). Alternatively, n is 2. Optionally, the at least one functional group comprises $NO_2$. Further optionally, the at least one functional group comprises a nitro group (—$NO_2$). Alternatively, the at least one functional group comprises a nitrosooxy (—ONO) group. Further alternatively, the at least one functional group comprises $NO_2$ and is selected from arginine. Optionally, the at least one functional group is L-arginine, and optionally acts as a substrate for nitric oxide synthase. Further alternatively, n is 3. Optionally, the at least one functional group comprises NO3. Further optionally, the at least one functional group comprises a nitrate group (—$ONO_2$), for example, a nitrate ester, optionally a nitrate ester of an alcohol. Still further optionally, the at least one functional group comprises a nitrate group (—ONO2), for example, a nitrate ester of an alkyl alcohol. Alternatively, the at least one functional group comprises a nitrate group (—ONO2), for example, a conjugate base of nitric acid (nitrate ion). By "associated with" is meant involving at least one chemical interaction. Optionally, the at least one functional group comprising N(O)n is involved in at least one chemical interaction with the tetracycline. Further optionally, the at least one functional group comprising N(O)n involves at least one electrostatic interaction with the tetracycline. Optionally, the at least one functional group comprising N(O)n forms at least one chemical bond with the tetracycline. Further optionally, the at least one functional group comprising N(O)n is a nitrate ester, which forms at least one chemical bond with the tetracycline. Optionally or additionally, the at least one functional group comprising N(O)n forms at least one chemical bond with the tetracycline via a linker molecule. Further optionally, the at least one functional group comprising N(O)n forms at least one chemical bond with the tetracycline via a linker molecule, wherein the at least one functional group comprising N(O)n is attached as a Mannich base to the tetracycline, optionally to the primary amide of the tetracycline. Optionally, the chemical bond is an ionic bond, wherein the interaction between the at least one functional group comprising N(O)n and the tetracycline is an interaction between oppositely charged atoms (or ions). Optionally, the oppositely charged atoms (or ions) are respectively located on or at the tetracycline and the at least one functional group comprising N(O)n. Preferably, the at least one functional group comprising N(O)n is selected from arginine and nitrate ion (ONO3-). Alternatively, the at least one chemical bond is a covalent bond between the at least one functional group comprising N(O)n and the tetracyline. Optionally, the electrons are respectively located on or at each of the at least one functional group comprising N(O)n and the tetracycline. Further optionally, the electrons are common (shared) electrons of the at least one functional group comprising N(O)n and the tetracycline, forming a covalent bond therebetween. Preferably, the compound, or the at least one functional group, is capable of releasing a molecule comprising N(O)n; wherein n is an integer selected from 1-3. Optionally, the compound, or the at least one functional group, is capable of releasing a molecule comprising NO (nitric oxide). Alternatively, the compound, or the at least one functional group, is capable of releasing NO2 (nitrogen dioxide). Further alternatively, the compound, or the at least one functional group, is capable of releasing NO3 (nitrate). By "capable of releasing a molecule" is meant dissociation of a molecule from the compound, such that the molecule is no longer associated with the tetracycline. Nitric oxide is a gaseous molecule that is unsuitable for oral administration. There are several pharmacologically relevant nitric-donor groups than are known to release nitric oxide in response to conditions found in the human body after administration. Exemplary nitric-donor groups are described in "Nitric Oxide Donors: For Pharmaceutical and Biological Applications"; Peng George Wang, Tingwei Bill Cai, Naoyuki Taniguchi, Wiley (2005), which is incorporated herein by reference. Optionally, the tetracycline is doxycycline. By "doxycycline" is meant the compound (4S,4aR,5S,5aR,6R,12aS)-4-(dimethylamino)-3,5,10,12,12a-pentahydroxy-6-methyl-1,11-dioxo-1,4,4a,5,5a,6,11,12a-octahydrotetracene-2-carboxamide. Optionally, the at least one functional group comprising N(O)n comprises: (a) a short-chain a short chain aza-alkyl, aza-alkenyl, or aza-alkynyl molecule, which can be linear, branched, or cyclic, and which can be substituted or unsubstituted; and (b) at least one group comprising $N(O)_n$, wherein n is an integer selected from 1-3, hereinafter referred to as a nitric-oxide donor group. Optionally, the at least one nitric oxide donor group comprises (a) a short-chain a short chain aza-alkyl molecule, which can be linear, branched or cyclic, and which can be substituted or unsubstituted; and (b) at least one at least one nitric oxide donor group. Optionally, the at least one nitric oxide donor-group comprises an amine, which can be linear, branched or cyclic, and which can be substituted or unsubstituted. Further optionally, the at least one nitric oxide donor group comprises a secondary amine, which can be linear, branched or cyclic, and which can be substituted or unsubstituted. Optionally, the at least one nitric oxide donor group comprises an aza-ethyl molecule (ethyl amine) and at least one at least one nitrate group. Further optionally, the at least one nitric oxide donor group comprises an aza-diethyl molecule (diethyl amine) and at least one at least one nitric oxide donor group. Preferably, the at least one nitric oxide donor group is a nitrate-ester containing group. Optionally, the at least one nitric oxide donor group comprises an aza-diethyl molecule (diethyl amine), wherein one nitrate group is attached to each ethyl group. Preferably, the at least one nitric oxide donor group is N,N-di-ethylnitrate amine. Optionally, the at least one nitric oxide donor group comprises a heterocyclic amine, which can be substituted or unsubstituted. Optionally, the at least one nitric oxide donor group comprises an aza-pentyl molecule and at least one at least one nitrate group. Further optionally, the at least one nitric oxide donor group comprises an aza-cyclo-pentyl molecule and at least one at least one nitrate group. Still further optionally, the at least one nitric oxide donor group comprises a piperidine molecule and at least one at least one nitrate group. Optionally, the at least one nitric oxide donor group comprises a piperidine molecule and at least one at least one alkyl-nitrate group. Further optionally, the at least one nitric oxide donor group comprises a piperidine molecule and at least one at least one methyl-nitrate group. Optionally, the at least one nitric oxide donor group comprises a piperidine molecule and at least one at least one alkyl-nitrate group. Further optionally, the at least one nitric oxide donor group comprises a piperidine molecule and at least one at least one methyl-nitrate group. Optionally, the at least one nitrate group, optionally the at least one alkyl-nitrate group, is attached to a carbon atom of the heterocyclic amine, optionally a carbon atom of the piperidine molecule. Further optionally, the at least one nitrate group, optionally the at least one alkyl-nitrate group, is attached to the carbon atom at position 3 of the heterocyclic amine, optionally the carbon atom at position 3 of the piperidine molecule. Optionally, the compound is amido-N—[N,N-diethylnitrate-aminomethyl]-α-6-deoxy-5-oxytetracycline. Alternatively, the compound is amido-N-[3-methylnitratepiperidinomethyl]-α-6-deoxy-5-oxytetracycline. Further alternatively, the compound is 6-deoxy-5-oxytetracycline nitrate salt.

BRIEF DESCRIPTION OF THE DRAWINGS

Embodiments of the present invention will be described, with reference to the accompanying drawings, in which.

DETAILED DESCRIPTION OF THE INVENTION

Figure 1:
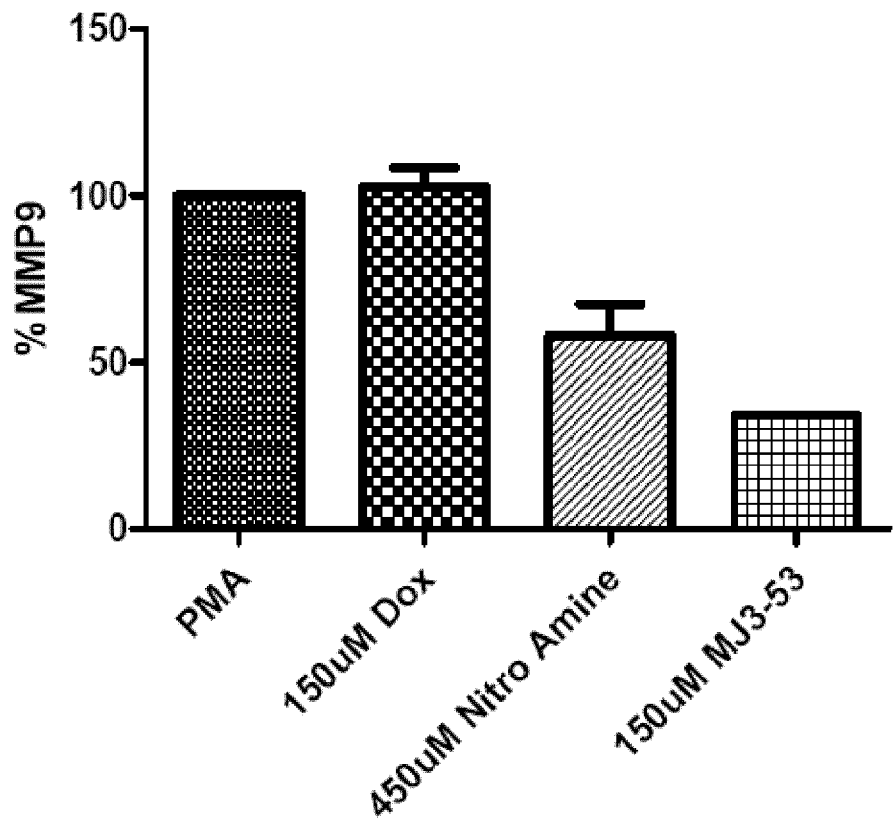
FIG. 1 is a graph depicting MMP-9 activity in response to PMA, 150 □M of doxycycline, 450 □M of nitro amine and 150 □M of MJ3-53 (Manich base dinitrate)

Embodiments of the present invention will now be exemplified, with reference to the following non-limiting examples.

EXAMPLE 1

Preparation of Nitrate-Containing Group, N,N-Diethylnitrate Amine

All materials were purchased from the Sigma-Aldrich chemical company. With reference to Scheme 1, 1.5 mL fuming nitric acid was dissolved in 10 mL DCM at −15° C. Diethanolamine (0.42 g, 4 mmole) dissolved in DCM (3 mL) was added dropwise over 20 minutes. The reaction mixture was then left stirring for a further 30 minutes before acetic anhydride (2 mL) was added to quench the reaction. The reaction was then left stirring for a further 5 minutes to form a precipitate. The precipitate was filtered washed with cold DCM and dried under vacuum to give N,N-diethylnitrate amine as a white solid.

HRMS ESI+ve C4H9N3O6 [M+H] requires 196.0570, found 196.0574. 1H NMR δ 3.52-3.54 triplet (2×CH2-O), δ 4.81-4.83 multiplet (2×CH2-N).

Scheme 1

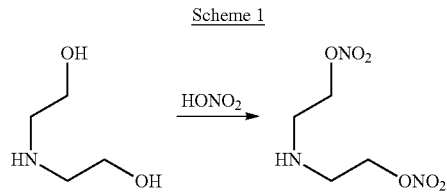

EXAMPLE 2

Preparation of Nitrate-Containing Group, 3-Methylnitrate Piperidine

With reference to Scheme 2, 1.5 mL fuming nitric acid was dissolved in 10 mL DCM at −15° C. 3-hydroxymethyl piperidine (0.46 g, 4 mmole) dissolved in DCM (3 mL) was added dropwise over 20 minutes. The reaction mixture was then left stirring for a further 30 minutes before acetic anhydride (2 mL) was added to quench the reaction. The reaction was then left stirring for a further 5 minutes.

The pH of the reaction mixture was then adjusted to 14 with 7M NaOH. The reaction mixture was then extracted with DCM (3×2o mL) and the combined organic extracts were washed with brine, dried over Na2SO4, filtered and solvent removed in vacuo to give 4-methyl nitrate piperidine as a pale yellow oil.

HRMS ESI+ve C6H12N2O3 [M+H]+ requires: 161.0921; found: 161.0923. 1H NMR: δ 3.62 multiplet (CH2-ONO2), δ 3.35-3.20 multiplet (C2, C6 CH2), 2.19 multiplet (C3CH) 2.11-1.90 multiplet (C5CH2).

Scheme 2

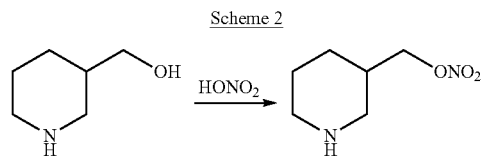

EXAMPLE 3

Preparation of Amido-N—[N,N-Diethylnitrate-Aminomethyl]-α-6-Deoxy-5-Oxytetracycline Referring to Scheme 3, N,N-di-ethylnitrate amine (0.095 g, 0.487 mmole; as prepared in Example 1) and paraformaldehyde (0.016 g, 0.487 mmole) were suspended in 10 mL isopropyl alcohol and heated to 75° C. under an inert atmosphere for 30 minutes until a clear solution was obtained. The reaction mixture was then cooled to 40° C. and doxycycline hyclate (0.250 g, 0.487 mmole), dissolved in a mixture of 5 mL isopropyl alcohol and 0.5 mL methanol, was added dropwise over 5 minutes. The reaction mixture was stirred at 40° C. for a further two hours. Upon completion of the reaction, the mixture was cooled and solvent removed to give amido-N—[N,N-diethylnitrate-aminomethyl]-α-6-deoxy-5-oxytetracycline as a pale yellow solid.

MS ESI-ve C27H33N5O14 [M−H]− requires 650.1951, found 650.1938. 1H NMR: δ 4.05 ppm singlet (Mannich methylene), δ 7.5, 6.95 ppm triplets and 7.85 ppm doublet (three phenyl protons) 2.9 ppm & 2.8 ppm singlets (dimethylamino, C4), δ 9.6 ppm singlet (amide), 3.52-3.54, triplet and 4.81-4.83, multiplet (diethyl amino nitrate).

Scheme 3

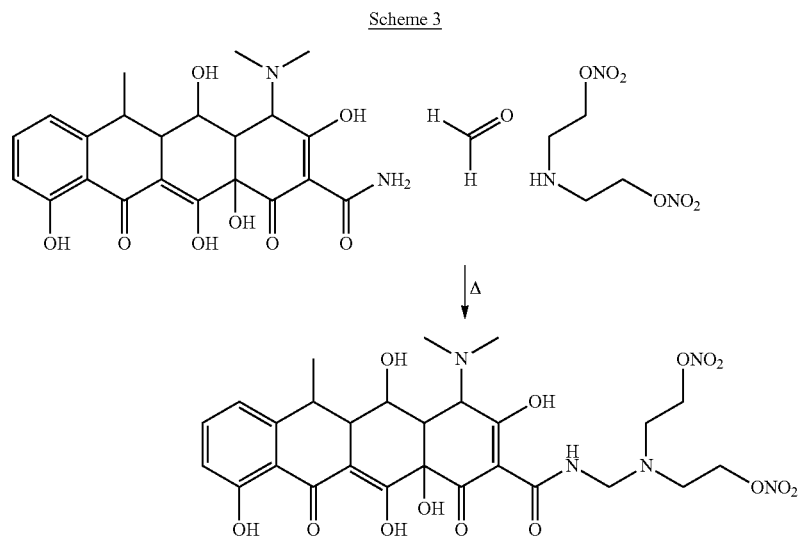

or alternative synthesis:

Amido-N-[Bis-(β-Nitrooxyethyl)Aminomethyl]-α-6-Deoxy-5-Oxytetracycline

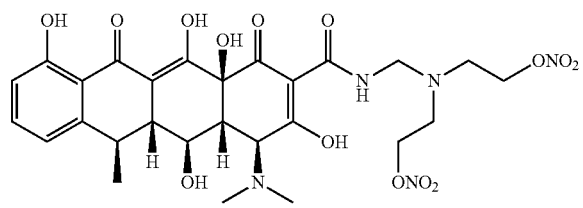

Diethanolamine-dinitrate (234 mg, 1.2 mM, 1.2 eq), doxycycline free base (414 mg, 1 mM, 1.0 eq) and para-formaldehyde (60 mg, 2 mM, 2 eq) were dissolved in anhydrous tetrahydrofuran (10 ml) and heated to refluxing for 2 h under nitrogen environment. Then another portion paraformaldehyde (60 mg, 2 mM, 2 eq) were added into the reaction mixture. After refluxing for another 2 h, the reaction mixture was cooled to room temperature and filtered. The filtrates were collected and the solvent was removed. The resulting solids were dried under vacuum to afford the title compound as a brown microcrystalline solid (162 mg, 25%). m p.=101-104° C. Calculated for $C_{27}H_{32}N_5O_{14}$=650.2024; found $(M-H)^-$=650.1965. $^1$H NMR (400 MHz, $d_6$-DMSO) δ 15.2 (1H, s), 11.5 (1H, s), 9.64 (1H, s), 9.1 (1H, s), 7.54 (1H, t, J=8), 6.94 (1H, d, J=8), 6.88 (1H, d, J=8), 5.4 (1H, s), 4.8 (4H, t, J=5), 4.65 (1H, dd, J=12, 7) 4.44 (1H, dd, J=12, 7) 4.17 (1H, s) 3.46-3.44 (5H, m) 2.73-2.65 (7H, m) 2.50-2.52 (1H, m) 1.47 (3H, d, J=7). $^{13}$C NMR (400 MHz, $d_6$-DMSO) ppm: 192.5, 171.6, 161.1, 147.8, 136.6, 115.8, 115.6, 115.5, 107.2, 73.2, 71.6, 68.8, 68.6, 68.0, 67.0, 62.0, 49.8, 45.2, 44.2, 41.3, 31.2; 15.8.

IR (KBr) ν (cm$^{-1}$): 3382; 2969; 1648; 1383; 1283; 849.

EXAMPLE 4

Preparation of Amido-N-[3-Methylnitratepiperidinomethy]-α-6-Deoxy-5-Oxytetracycline Referring to Scheme 4, to 6-deoxy-5-oxytetracycline hyclate (0.461 g, 0.899 mmole) in anhydrous THF (10 mL) was added 3-methylnitrate piperidine (as prepared in Example 2) and 0.1 mL 37% formaldehyde solution. The reaction mixture was stirred at 40° C. for 16 hours. The reaction mixture was then cooled and solvent removed under reduced pressure to give amido-N-[4-methylnitratepiperidinomethyl]-α-6-deoxy-5-oxytetracycline as a pale yellow solid. MS APCI C29H36N4O11 [M+NH4] requires 616.2831 found 616.2944. $^1$H NMR: δ 4.05 ppm singlet (Mannich methylene), δ 7.5, 6.95 ppm triplets and 7.85 ppm doublet (three phenyl protons) 2.9 ppm & 2.8 ppm singlets (dimethylamino, C4), δ 9.6 ppm singlet (amide), δ 3.62 multiplet ($CH_2$—$ONO_2$), δ 3.35-3.20 multiplet (C2, C6CH2), 2.19 multiplet (C3CH) 2.11-1.90 multiplet (C5CH$_2$)

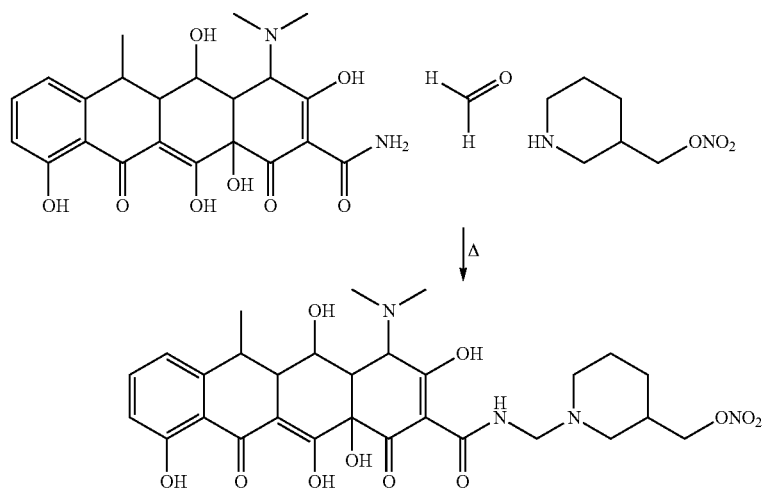

or alternative synthesis:

Amido-N-[3-(Nitrooxymethyl)Piperidinomethyl]-α-6-Deoxy-5-Oxytetracycline

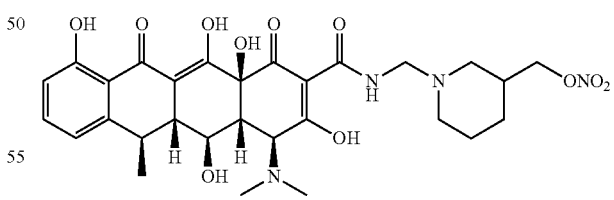

3-Nitrooxymethyl piperidine (192 mg, 1.2 mM, 1.2 eq), doxycycline free base (414 mg, 1 mM, 1.0 eq) and para-formaldehyde (60 mg, 2 mM, 2 eq) were dissolved in anhydrous tetrahydrofuran (10 ml) and heated to refluxing for 2 h under nitrogen environment. Then another portion of paraformaldehyde (60 mg, 2 mM, 2 eq) was added into the reaction mixture. After refluxing for another 2 h, the reaction mixture was cooled to room temperature and filtered. The filtrates were collected and the solvent was removed. The resulting solids were dried under vacuum to afford the title compound as a pale yellow microcrystalline solid (153 mg, 25%). Calculated for $C_{29}H_{35}N_4O_{11}$=615.2308; found $(M-H)^-$=615.2291. $^1H$ NMR (400 MHz, $d_6$-DMSO) δ 15.3 (1H, s) 11.6 (1H, s) 10.12 (1H, s) 9.64 (1H, s) 7.54 (1H, t, J=8) 6.94 (1H, d, J=8) 6.88 (1H, d, J=8) 5.72 (1H, s) 4.65 (1H, dd, J=12.7) 4.45-4.30 (3H, m) 4.07 (1H, s) 3.22-3.35 (2H, m) 2.98-2.89 (2H, m) 2.80-2.65 (8H, m) 2.15-1.96 (2H, m) 1.89-1.75 (2H, m) 1.52-1.4 (4H, m).

Scheme 4

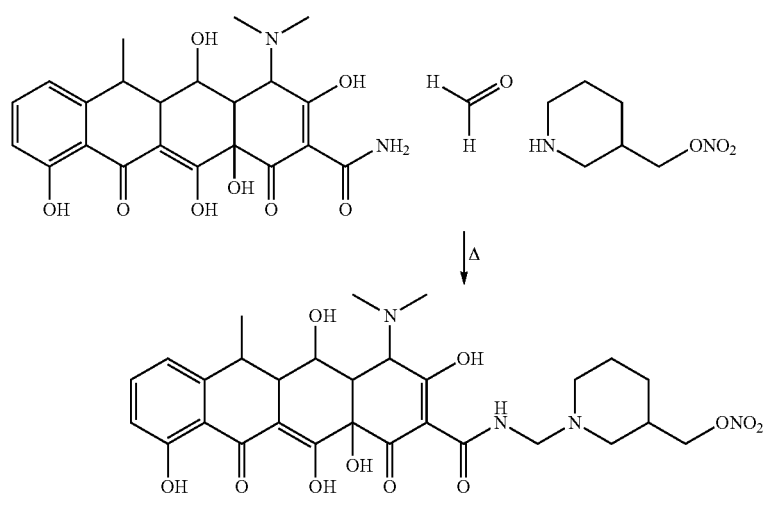

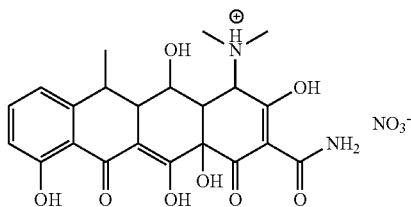

EXAMPLE 5

Preparation of 6-Deoxy-5-Oxytetracycline Nitrate Salt

With reference to Scheme 5, a nitrate salt is prepared by adding silver nitrate (0.50 g, 2.96 mmole) to a solution of doxycycline hydrochloride (1.52 g, 2.96 mmole) in acetonitrile (20 mL). The solution is then stirred at room temperature for 30 minutes.

After 30 minutes, a white precipitate of silver chloride was removed by filtration to leave a pale yellow solution. This solution was added dropwise to cold diethyl ether (100 mL) to form a pale yellow precipitate that was filtered, washed with cold diethyl ether, and dried under vacuum.

HRMS ESI C22H24N2O8 [M]+ requires 445.1605, found 445.1602.

Scheme 5

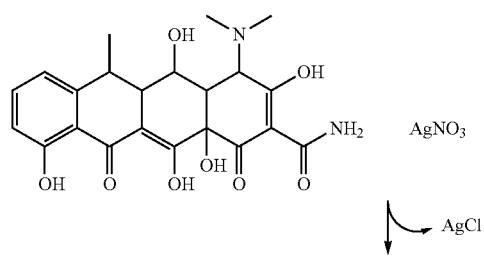

EXAMPLE 6

Docycycline-5-Nitrate

A solution of doxycyline (414 mg, 1 mmol) in 5 ml THF was added to the solution of $Cu(NO_3)_2$ (750 mg, 3 mmol) in 15 ml of acetic anhydride, which had been reacted for 2 h at room temperature. After reacted at −10° C. for 3 hour, the reaction mixture was filtered. The solvent of the filtrate was removed and dried under vacuum to give an amber solid (215, 44%). Calculated for $C_{22}H_{24}N_3O_{10}$=490.1456; found $(M+H)^+$=490.1469.

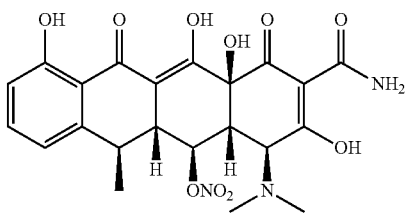

EXAMPLE 7

4-Nitrooxymethyl piperidine (192 mg, 1.2 mM, 1.2 eq), doxycycline free base (414 mg, 1 mM, 1.0 eq) and para-formaldehyde (60 mg, 2 mM, 2 eq) were dissolved in anhydrous tetrahydrofuran (10 ml) and heated to refluxing for 2 h under nitrogen environment. Then another portion of paraformaldehyde (60 mg, 2 mM, 2 eq) was added into the reaction mixture. After refluxing for another 2 h, the reaction mixture was cooled to room temperature and filtered. The filtrates were collected and the solvent was removed. The resulting solids were dried under vacuum to afford the title compound as a pale yellow microcrystalline solid (128 mg, 21%). m p.=130-132° C. Calculated for $C_{29}H_{35}N_4O_{11}$=615.2308; found (M−H)$^−$=615.2277. $^1$H NMR (400 MHz, d$_6$-DMSO) δ 15.3 (1H, s) 11.6 (1H, s) 9.64 (1H, s) 9.1 (1H, s) 7.54 (1H, t, J=8) 6.94 (1H, d, J=8) 6.88 (1H, d, J=8) 5.72 (1H, s) 4.65 (1H, dd, J=12, 7) 4.45-4.30 (3H, m) 4.07 (1H, s) 3.22-3.35 (2H, m) 2.98-2.89 (2H, m) 2.73-2.65 (7H, m) 2.50 (1H, m) 2.15-1.96 (2H, m) 1.89-1.75 (2H, m) 1.52-1.4 (5H, m). $^{13}$C NMR (400 MHz, d$_6$-DMSO) ppm: 192.5, 171.6, 161.1, 147.8, 136.7, 115.8, 115.6, 115.5, 107.1, 76.4, 68.9, 68.2, 66.6, 50.7, 45.3, 41.6, 38.4, 31.2, 26.6, 15.8.

IR (KBr) ν (cm$^{-1}$): 3401; 29769; 1634; 1383; 1279; 867.

EXAMPLE 8

Amido-N-[4-nitrooxypiperidinomethyl]-α-6-deoxy-5-oxytetracyline

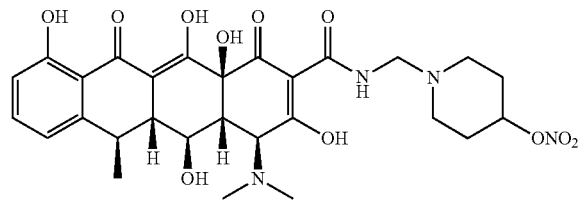

4-nitrooxypiperidine (175 mg, 1.2 mM, 1.2 eq), doxycycline free base (414 mg, 1 mM, 1.0 eq) and paraformaldehyde (60 mg, 2 mM, 2 eq) were dissolved in anhydrous tetrahydrofuran (10 ml) and heated to refluxing for 2 h under nitrogen environment. Then another portion of paraformaldehyde (60 mg, 2 mM, 2 eq) was added into the reaction mixture.

After refluxing for another 2 h, the reaction mixture was cooled to room temperature and filtered. The filtrates were collected and the solvent was removed. The resulting solids were dried under vacuum to afford the title compound as a pale yellow microcrystalline solid (192 mg, 32%). Calculated for $C_{28}H_{33}N_4O_{11}$=601.2151; found (M−H)$^−$=601.2152. $^1$H NMR (400 MHz, d$_6$-DMSO) δ 15.3 (1H, s) 11.6 (1H, s) 9.64 (1H, s) 7.54 (1H, t, J=8) 6.94 (1H, d, J=8) 6.88 (1H, d, J=8) 5.72 (1H, s) 5.27-5.30 (m, 1H) 4.65 (1H, dd, J=12, 7) 4.43 (1H, dd, J=12, 7) 4.07 (1H, s) 3.22-3.25 (4H, m) 2.73- 2.65 (7H, m) 2.50 (1H, m), 1.88-1.91 (2H, m) 1.47 (3H, d, J=7).

EXAMPLE 9

Amido-N-[3-(nitrooxymethyl)piperidinomethyl]-α-6-deoxy-5-oxytetracycline

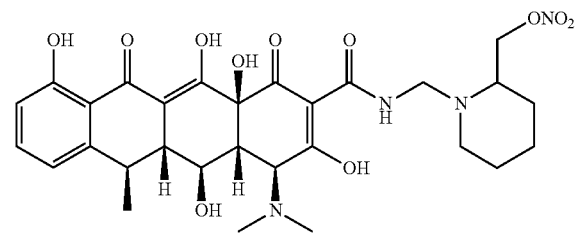

3-Nitrooxymethyl piperidine (192 mg, 1.2 mM, 1.2 eq), doxycycline free base (414 mg, 1 mM, 1.0 eq) and paraformaldehyde (60 mg, 2 mM, 2 eq) were dissolved in anhydrous tetrahydrofuran (10 ml) and heated to refluxing for 2 h under nitrogen environment. Then another portion of paraformaldehyde (60 mg, 2 mM, 2 eq) was added into the reaction mixture. After refluxing for another 2 h, the reaction mixture was cooled to room temperature and filtered. The filtrates were collected and the solvent was removed. The resulting solids were dried under vacuum to afford the title compound as a pale yellow microcrystalline solid (171 mg, 28%). Calculated for $C_{29}H_{35}N_4O_{11}$=615.2308; found (M−H)$^−$=615.2305.

EXAMPLE 10

Amido-N-[(β-nitrooxyethyl)aminomethyl]-α-6-deoxy-5-oxytetracycline

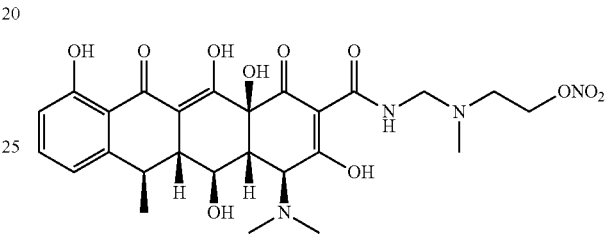

1-Methylaminoethyl nitrate (200 mg, 1.88 mM, 1.2 eq), doxycycline free base (700 mg, 1.55 mM, 1.0 eq) and paraformaldehyde (93 mg, 3.1 mM, 2 eq) were dissolved in anhydrous tetrahydrofuran (10 ml) and heated to refluxing for 2 h under nitrogen environment. Then another portion paraformaldehyde (93 mg, 3.1 mM, 2 eq) were added into the reaction mixture. After refluxing for another 2 h, the reaction mixture was cooled to room temperature and filtered. The filtrates were collected and the solvent was removed. The resulting solids were dried under vacuum to afford the title compound as a pale yellow microcrystalline solid (261 mg, 30%). Calculated for $C_{26}H_{31}N_4O_{11}$=575.1995; found (M−H)$^−$=575.2032. $^1$H NMR (400 MHz, d$_6$-DMSO) δ 15.2 (1H, s), 11.5 (1H, s), 9.64 (1H, s), 9.64 (1H, s), 7.54 (1H, t, J=8), 6.94 (1H, d, J=8), 6.88 (1H, d, J=8), 5.4 (1H, s), 4.8 (2H, t, J=5), 4.65 (1H, dd, J=12, 7) 4.44 (1H, dd, J=12, 7) 4.17 (1H, s) 3.46-3.44 (3H, m) 2.73-2.65 (7H, m) 2.50-2.52 (1H, m) 1.47 (3H, d, J=7).

EXAMPLE 11

Amido-N-[4-nitrooxypiperidinomethyl]-tetracycline

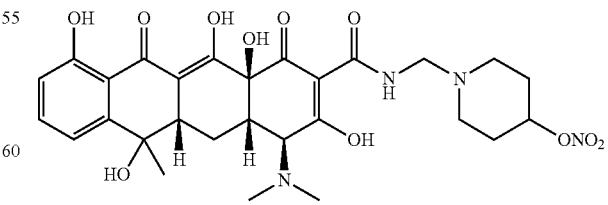

4-nitrooxypiperidine (175 mg, 1.2 mM, 1.2 eq), tetracycline free base (414 mg, 1 mM, 1.0 eq) and paraformaldehyde (60 mg, 2 mM, 2 eq) were dissolved in anhydrous tetrahydrofuran (10 ml) and heated to refluxing for 2 h under nitrogen environment. Then another portion of paraformaldehyde (60 mg, 2 mM, 2 eq) was added into the reaction mixture. After refluxing for another 2 h, the reaction mixture was cooled to room temperature and filtered. The filtrates were collected and the solvent was removed. The resulting solids were dried under vacuum to afford the title compound as a brown microcrystalline solid (216 mg, 36%). Calculated for $C_{28}H_{33}N_4O_{11}$=601.2151; found (M–H)⁻=601.2147. $^1$H NMR (400 MHz, d$_6$-DMSO) δ 15.3 (1H, s) 11.6 (1H, s) 9.64 (1H, s) 9.64 (1H, s) 7.54 (1H, t, J=8) 7.1 (1H, d, J=8) 6.93 (1H, d, J=8) 5.27-5.30 (m, 1H) 5.10 (1H, s) 4.65 (1H, dd, J=12, 7) 4.43 (1H, dd, J=12, 7) 4.07 (1H, s) 3.22-3.25 (4H, m) 2.65-2.73 (7H, m) 2.50 (1H, m), 2.04-2.13 (2H, m) 1.88-1.91 (2H, m) 1.53 (3H, s).

EXAMPLE 12

Amido-N-[bis-(β-nitrooxyethyl)aminoethyl]-α-6-deoxy-5-oxytetracycline

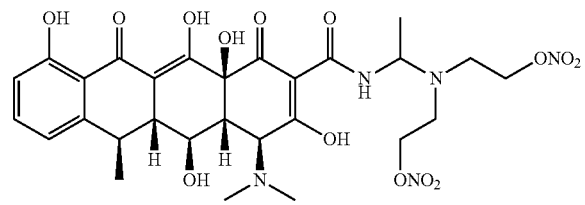

Diethanolamine dinitrate (195 mg, 1 mmol, 1 eq) doxycycline free base (450 mg, 1 mmol, 1 eq) and acetaldehyde (110 uL, 88 mg, 2 eq) were dissolved in anhydrous tetrahydrofuran (10 ml) and heated to reflux for 2 hours under nitrogen environment. A further 2 equivalents of acetaldehyde were added to the reaction mixture and the reaction continued for a further 2 h. The reaction mixture was then cooled to room temperature and filtered. THF was removed from the filtrate via rotary evaporation and the resultant residue was dried under vacuum to give an amber solid. (235 mg, 35%) $^1$H NMR (400 MHz, d$_6$-DMSO) δ 15.2 (1H, s), 11.5 (1H, s), 9.64 (1H, s), 7.54 (1H, t, J=8), 6.94 (1H, d, J=8), 6.88 (1H, d, J=8), 5.4 (1H, s), 4.57 (4H, t, J=5), 4.44, 1H, dd, J=12, 7) 4.17 (1H, s) 3.46-3.44 (5H, m) 2.73-2.65 (7H, m) 2.50-2.52 (1H, m) 1.78 (3H, d, J=7) 1.47 (3H, d, J=7).

EXAMPLE 13 & 14

Figure 2:
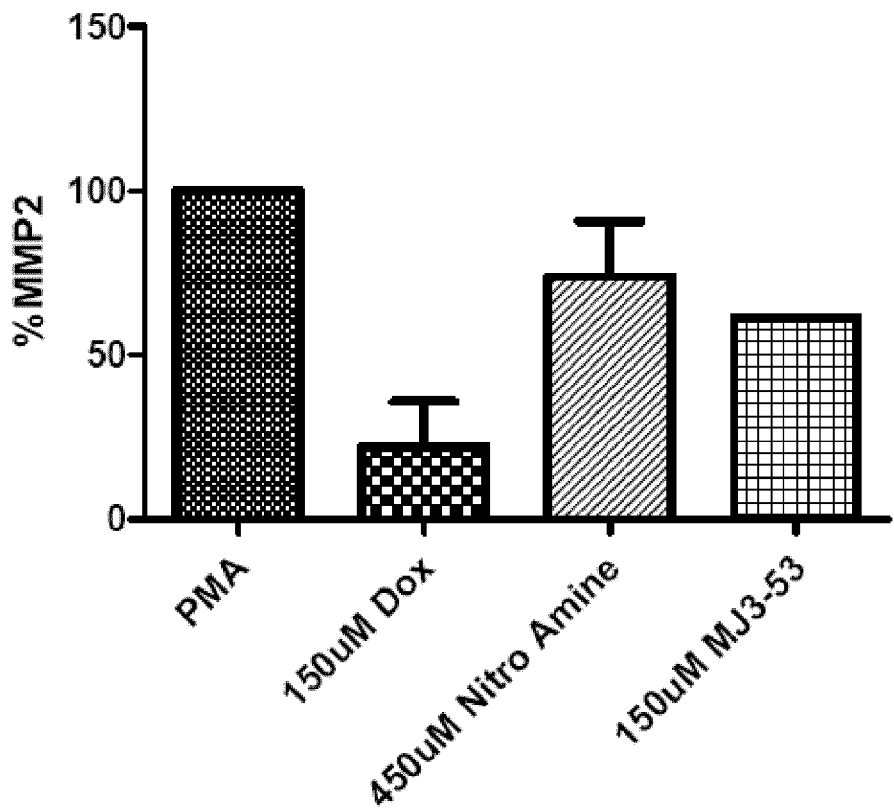
FIG. 2 is a graph depicting MMP-2 activity in response to PMA, 150 □M of doxycycline, 450 □M of nitro amine and 150 □M of MJ3-53 (Manich base dinitrate)
Figure 3:
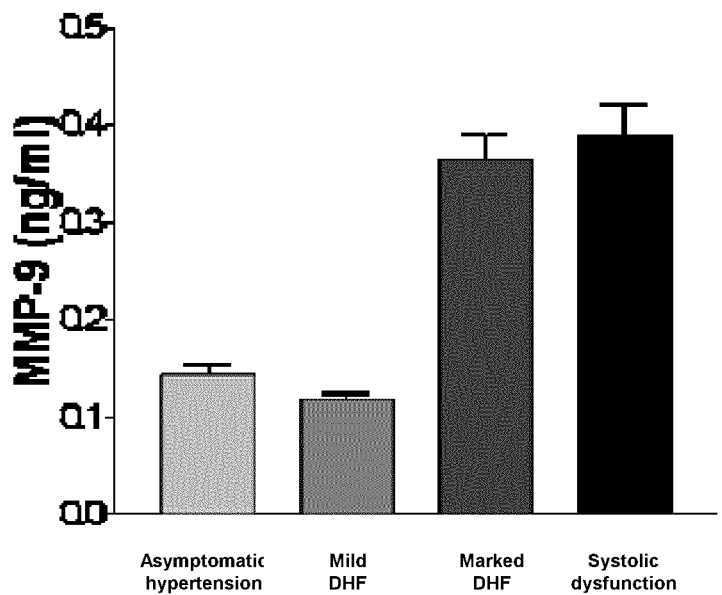
FIG. 3 is a graph depicting MMP-9 expression in patients with varying degrees of DHF.
Figure 4:
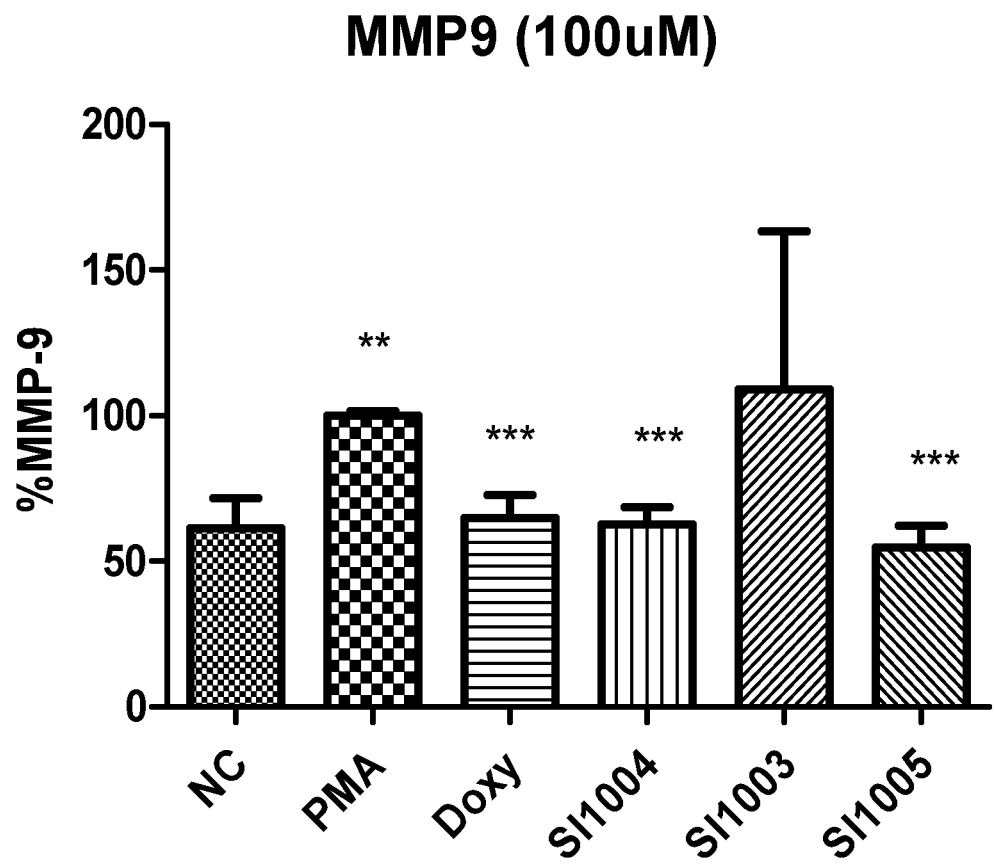
FIG. 4 demonstrates the effect of SI1003, SI1004, SI1005 and doxycycline on MMP-9 activity in PMA stimulated breast cancer cells (NC=negative control).

*Doxycycline*-12a-nitrate; and minocycline-12a-nitrate; both of which may be prepared by mild nitration under acidic conditions. In vitro pharmacological evaluation Cells (CaCo2 cells) were seeded onto a 12-well plate, and allowed to grow to 70% confluence. When cells were 70% confluent, the media on the cells were replaced with serum-free media. Cells were then treated with increasing concentrations of test compound (50 ☐M-250 ☐M), for 3 hours in a 37° C. incubator. After 3 hours, 10 ☐M PMA (Phorbol 12-myristate 13-acetate) was added to the cells to induce production of MMPs. Cells were incubated for 24 hours in a 37° C. incubator. After 24 hours, the media from each well were collected and centrifuged at max speed for 5 minutes to pellet any cellular debris, and the media was removed to fresh microfuge tubes. A Bradford assay was conducted to determine the protein concentration of each media sample. An equal protein concentration of each media sample was loaded onto a zymography gel, which was run for 150V/2 hours. Following this, the zymography gel was washed three times for 20 minutes in 2.5% Triton X Buffer and was washed 2 times in zymography buffer before being incubated in zymography buffer at 37° C. for 48-72 hours to allow any MMP9 and MMP2 present to digest the gelatinase in the gel. Following this, the gels were stained in coomassie blue stain for 3 hours with gentle rocking and destained for 1 hour, resulting in a blue gel with clear bands where MMP's that were present had digested through the gelatine in the zymography gels. Densitometry analysis was performed to quantitate the amount of MMPs present relative to the PMA positive control sample. Referring to FIG. 1, addition of 150 uM of doxycycline did not affect MMP-9 levels. N,N-diethylnitrate amine, at equimolar concentrations to the Mannich base dinitrate (amido-N—[N,N-diethylnitrate-aminomethyl]-α-6-deoxy-5-oxytetracycline) on its own, inhibited MMP-9 by over 50%. However, the combination of doxycycline with the nitrate amine amido-N—[N,N-diethylnitrate-aminomethyl]-α-6-deoxy-5-oxytetracycline] (MJ3-53) suppressed MMP-9 activity by approximately 60%. Referring to FIG. 2, it can be seen that MMP-2 activity was significantly inhibited by doxycycline (80%), and the combination with amido-N—[N,N-diethylnitrate-aminomethyl]-α-6-deoxy-5-oxytetracycline reduced MMP-2 activity by about 40%. These data demonstrate that a compound of the present invention is capable of significantly altering MMP expression, and finds utility in treating or preventing heart failure, optionally heart failure caused by or associated with diastolic dysfunction; where MMP-9 levels are three times higher in the advanced stages compared with mild DHF. In DHF, MMP2 is 40 to 50% higher and MMP9 is 200-300% higher in heart failure patients than in asymptomatic hypertensive patients. In the present example, surprisingly, the amido-N—[N,N-diethylnitrate-aminomethyl]-α-6-deoxy-5-oxytetracycline inhibits MMP9 more than by the constituent doxycycline and N,N-diethylnitrate amine. Moreover, the pattern of MMP 2 and MMP9 inhibition may be more beneficial than doxycycline alone, which, in these examples, did not reduce MMP9.

In-vitro/in-vivo Effects of Doxycycline and SI1004

The purpose of this study was to evaluate the in-vitro/in-vivo effects of doxycycline and SI1004, a novel NO-releasing analogue of doxycycline which could be applied to the treatment of disorders associated with elevated MMP-9 including ALVDD and HFpEF.

Methods

Direct Inhibition of Recombinant MMP-2 and MMP-9 with SI1004 and Doxycycline.

Nitrocycline, SI1004, a dinitroxyethyl conjugate with doxycycline was prepared in-house using conventional chemical approaches and characterised by $^1$H, $^{13}$C NMR, High Resolution Mass Spectroscopy and High Performance Liquid Chromatography. Doxycycline hyclate was obtained from Sigma-Aldrich Ireland. In order to determine the relative direct inhibitory effects of SI1004 and doxycycline on MMP-2 and MMP-9 we used human recombinant enzymes (R&D Systems, Ireland) with the synthetic broad-spectrum fluorogenic substrate (7-methoxycoumarin-4-yl)-acetyl-pro-Leu-Gly-Leu-(3-(2,4-dinitrophenyl)-L-2,3-di-aminopropionyl)-Ala-Arg-NH$_2$ (R&D Systems, UK) as previously described (34).

Effects of SI1004 and Doxycycline on Human Ventricular Cardiac Fibroblast (HCF) proliferation and on TNF-α treated HCF MMP-2 and MMP-9 transcription.

The impact of SI1004 and doxycycline on MMP-2 and MMP-9 transcription was evaluated in primary HCFs purchased from ScienCell Research Laboratories. Cells were cultured in Dulbecco's modified eagles medium (DMEM) (Gibco), supplemented with 10% Fetal Calf Serum (FCS) (Gibco) and penicillin-streptomycin antibiotics (Gibco) in a 5% $CO_2$ humidified incubator kept at 37° C. To investigate effects of test articles on cell proliferation, HCF cells were serum starved for 72 hours and then treated with either 75 or 150 µM of test article in DMSO in 2% FCS for a further 72 hours. Cell viability was measured using the CellTitre-Glo Luminescent Cell Viability Assay (Promega) which measures ATP as an indicator of the number of metabolically active cells. To investigate the relative effects of doxycycline and SI1004 on TNFα treated HCF transcription of MMP-2 and MMP-9, cells were treated with 10 ng/mL human recombinant TNFα (R&D Systems) for 72 hours in the presence of 75 µM or 150 µM of test article in DMSO. RNA was isolated using a NucleoSpin RNA II Kit (Macherey-Nagel). First strand cDNA synthesis was carried out using SuperScript II RT (Invitrogen). QPCR primers were designed so that one of each primer pair was exon/exon boundary spanning to ensure only mature mRNA was amplified. The sequences of the gene-specific primers used are as follows; MMP-2, 5'-CACGTGACAAGCCCATGGGGC-CCC-3' (forward), 5'-GCAGCCTAGCCAGTCGGATTT-GATG-3' (reverse); MMP-9,5'-GTGCTGGGCTGCT-GCTTTGCTG-3' (forward), 5'-GTCGCCCTCAAAGGTTTGGAAT-3' (reverse). QPCR reactions were normalized by amplifying the same cDNA with GAPDH primers, 5'-ACAGTCAGCCGCATCTTCTT-3' (forward), 5'-ACGACCAAATCCGTTGACTC-3' (reverse). QPCR was performed using Platinum SYBR Green qPCRSuperMix-UDG (Invitrogen). Amplification and detection were carried out using the Mx3000P System (Stratagene). The PCR cycling program consisted of 40 three-step cycles of 15 seconds/95° C., 30 seconds/TA and 30 seconds/72° C. Each sample was amplified in duplicate. In order to confirm signal specificity, a melting program was carried out after the PCR cycles were completed. The samples were quantified by comparison with a standard calibration curve created at the same time and the data was normalized by an internal control (glyceraldehyde 3-phosphate dehydrogenase).

Effects of SI1004 and Doxycycline on MMPs, TIMP-1 and Inflammatory Markers in Human Peripheral Blood mononuclear cells (PBMC) stimulated with TNF-α.

To further explore the relative impact of SI1004 and doxycycline on inflammatory cells (PBMC), venous blood (30 mL) was collected from three healthy volunteers (age 30-37) in 10 mL S-Monovette tubes with anti-coagulant 9NC (Sarstedt). The blood was mixed with an equal volume of D-PBS (Gibco) and two volumes of the mixture were layered over one volume of Lymphoprep gradient solution (Axis-Shield). PBMC were isolated by centrifugation at 400 g for 40 minutes. PBMC were collected from the plasma/lymphoprep interface and washed three times in D-PBS/0.1% BSA/2 mM EDTA. PBMC were suspended at $1 \times 10^6$ cells/mL in pre-warmed RPMI 1640/10% FCS/2 mM L-glutamine/100 µg/mL penicillin G/100 µg/mL Streptomycin (all from Gibco). Cells ($0.2 \times 10^6$) were plated at a concentration of $1.0 \times 10^6$ in 96-well plates in duplicates, stimulated with 10 ng/mL TNFα (R&D Systems) with/without doxycycline hyclate or SI1004 (at 75 and 150 µM) and incubated for 24 hours at 37° C. On the following day, all samples were centrifuged and supernatants were stored at −80° C. for immunoassays. Percent PBMC viability following drug treatment was determined using the CellTiter-Glo Luminescent Cell Viability Assay (Promega) according to the manufacturer instructions. The cytokine profile of the cell supernatants was analysed using an ultra-sensitive immunoassay with electrochemiluminescence detection according to the manufacturer's instructions (Meso Scale Discovery). MMP secretion was also quantified using multiplex immunoassays with electrochemiluminescence detection as instructed by the manufacturer (MMP2/10 Duplex and MMP1/3/9 Triplex assays—MesoScale Discovery). Single-plex assays were used for monocyte chemotactic protein (MCP)-1 (Meso Scale Discovery). Plates were analyzed using a Meso Scale Discovery Sector Imager 2400 instrument. Secreted TIMP-1 was quantified using a standard ELISA (Amersham, GE Healthcare). TH1/TH2 10-plex assay was used to study IFNγ, IL-1β, IL-2, IL-4, IL-5, IL-8, IL-10, IL-12p70, IL-13, and TNFα. The sensitivity (lowest level of detection) of the assays was 0.12 ng/mL and 0.1 ng/mL for MMP-2 and MMP-9, respectively. The coefficient of variation of the lower limit of the standard curve for MMP-2 and MMP-9 was 4.9% and 1.2% respectively. Plates were analyzed using a Meso Scale Discovery Sector Imager 2400 instrument.

Relative Effects of SI1004 and Doxycycline on Total MMP-2 and MMP-9 Levels on Acute and Repeated Oral administration over three days with dose titration following day one in non-human primates (NHP).

A total of 12 purpose bred, purpose bred, naïve, non-human primates (cynomolgus monkeys, 2.9-4 kg) were sourced and randomly allocated in a parallel group design (n=6 per group) to receive SI1004, SI1005 and equimolar doses of doxycycline daily (1.6 mg/kg doxycycline hyclate equivalents, on day 1 and 4.8 mg/kg doxycycline equivalents on days 2 and 3) by oral gavage in aqueous vehicle over a 3 day period. Studies were carried out consecutively in two contract research organization sites (Charles River, Sparks, Nev., US and Charles River, Shanghai, China). The study protocol was approved by PCS-SHG Institutional Animal Care and Use Committee before conduct. During the study, care and use of animals was conducted in accordance with the guidelines of the USA National Research Council and the Canadian Council on Animal Care. The cynomolgus monkey was chosen for this study in order to maximize the likelihood of identifying responses that are similar to those that may be expected in humans. Each animal was identified by a cage label and body tattoo and was acclimated to orogastric dosing on at least two occasions prior to the initiation of dosing. The vehicle (1% (w/v) tween 80 and 0.5% (w/v) carboxymethylcellulose in deionized water) or 1.6 mg/kg doxycycline hyclate (0 hours) or 4.8 mg/kg doxycycline hyclate (24, 48 hours) or the molar equivalent(s) of SI1004 or SI1005 were administered using an orogastric tube inserted through the mouth and advanced into the stomach. The animals were temporarily restrained (i.e. manually) for dose administration, and were not sedated. Disposable sterile syringes and orogastric tubes were used for each animal/dose. Each dose was followed by a tap water flush of approximately 5 mL. Blood samples and blood pressure measurements were taken at the following timepoints: pre-dose (0 hours) and at 2, 4, 6, 12, 24, 26, 30, 36, 48, 50, 54, 60 and 72 hours after first administration of test article. We have previously demonstrated an acute phase response in this model to repeated venepuncture (3-6 fold increase in high sensitivity C-reactive protein from baseline at 12 and 24 hours post dose respectively, (both p=0.01 vs baseline), data not shown). Blood (300 µL) for serum preparation was collected intoBD Vacutainer®+Serum SST™ tubes to accelerate clotting 20 minutes prior to centrifugation to allow complete clotting to occur and centrifuged at 1500-2200 rpm at 2-8° C. for 10-15 minutes. Under these conditions blood cells containing MMP, principally neutrophils and platelets, undergo full degranulation. Since artifactual elevation of MMP-9 was an unavoidable feature of repeated venipuncture in our model, it was logical to stimulate full MMP-9 release during sample collection. This provided greater inter-animal reproducibility and a more dynamic analytical range for assessing the relative effects of the test articles. Subsequent MMP-9 values provide an index of total MMP-9 including circulating enzyme, amplified by repeated venipuncture, along with the cellular load released from storage granules during clotting. The latter is influenced by earlier inflammatory signaling, transcription and storage. The serum was transferred to a cryovial and immediately stored at −70° C. until analyzed for MMP-2 and MMP-9 via a Luminex ELISA (total MMP-2 and MMP-9) within 48 hours of collection. The analysis of each time point was repeated within 5 days. Values that differed by more than 15% were repeated. The primary study endpoint was the change in plasma MMP-2 and MMP-9 levels at 72 hours. Secondary endpoints were area under the curve (AUC) values of MMP-2 and MMP-9 over the following periods: 0-24, 0-48 and 0-72 hours. Additional 0.4 mL aliquots were placed in $K_2$EDTA tubes and processed to plasma for combined nitrate/nitrate ($NO_x$) analysis using a modified Greiss assay as previously described (35). Simultaneous blood pressure measurements were made in triplicate using a femur cuff linked to an automated Omron analyzer. Data are presented as mean±standard error of the mean (SEM) for continuous normal variables, median, inter-quartile range (IQR) with 95% confidence intervals for non-normal continuous variables and frequencies and percents for nominal/categorical variables. Comparisons between doxycycline and SI1004 groups in the NHP study were made on changes over the study period using independent two-sample t-tests for continuous normally distributed data, Mann-Whitney for skewed continuous and chi-squared for categorical data. Within group tests, comparing baseline to 24, 48 and 72 hour values, were conducted using paired sample t-tests and paired sample Wilcoxon tests where appropriate. Analyses were carried out using SPSS V.13 statistical software (Statistical Package for the Social Sciences: SPSS Inc, Chicago, Ill., 2001).

Results

Effects of Doxycycline and SI1004 on Activity of Recombinant Human MMP-2 and MMP-9

Doxycycline and SI1004 had similar direct inhibitory effects on MMP-2 and MMP-9 enzymatic activity. Doxycycline (100 µM) inhibited recombinant human MMP-2 (34.0±3.5%) and MMP-9 (33.3±3.5%) ($p<0.05$). Similarly SI1004 (100 µM) inhibited MMP-2 and MMP-9 by 29.7±2.1% and 26.6±1.7% respectively ($p<0.05$). However, there was no direct inhibition of either enzyme by the test articles at 10 µM. These values suggest weak, non-selective inhibition of both gelatinases at enzyme level and are consistent with doxycycline's low binding affinity for the MMPs.

Effects of Doxycycline and SI1004 on Human Cardiac Fibroblasts

In contrast to doxycycline hyclate, SI1004 significantly inhibited TNFα induced upregulation of MMP-9 mRNA ($p=0.01$, FIG. 1A). MMP-9 protein levels were below the lower limit of quantification in doxycycline hyclate or SI1004 treated cell supernatants. There were no significant effects of doxycycline hyclate or SI1004 on MMP-2 mRNA expression. Also, unlike doxycycline, SI1004 (75-150 µM) caused significant inhibition of HCF proliferation in 2% FCS following serum starvation for 72 hours, ($p=0.02$, FIG. 1B).

Effects of Doxycycline and SI1004 on Markers of Inflammation and Collagen Turnover in Human Peripheral Blood Mononuclear Cells The effects of doxycycline hyclate and SI1004 on MMPs, TIMP-1, inflammatory cytokines and MCP-1 are presented in Table 1. Both compounds significantly inhibited PBMC supernatant MMP-9, TIMP-1, IFNγ, IL-8, IL-12p70 and MCP-1 (all $p<0.05$). SI1004 (150 µM) but not doxycycline, inhibited IL-1β production at 150 µM ($p=0.03$). Doxycycline inhibited TIMP-1 to a greater extent than SI1004 at both concentrations ($p<0.05$) and doxycycline, but not SI1004, inhibited MMP-3 ($p<0.02$).

Figure 12:
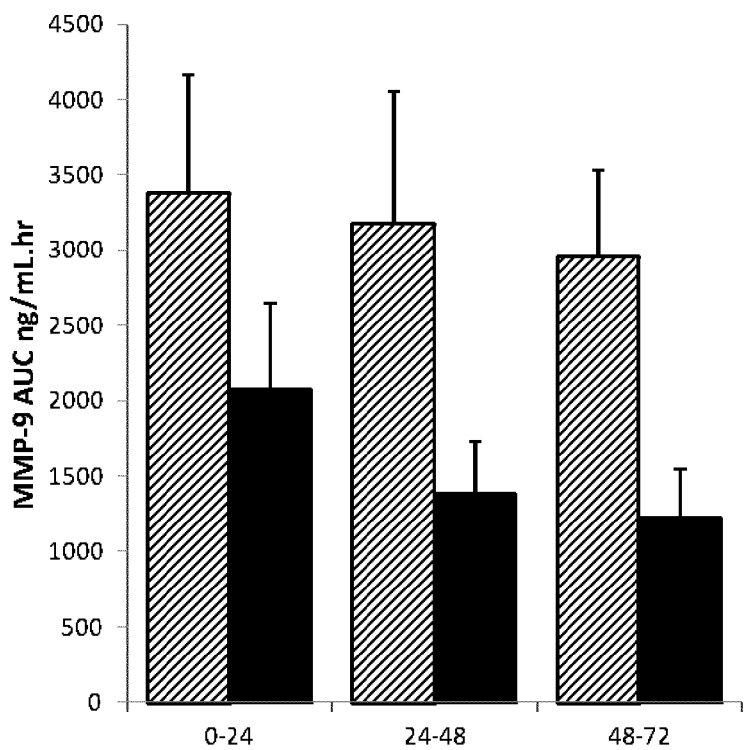
FIG. 12. Impact of doxycycline hyclate (striped bars) and SI1004 (solid bars) on [A] total MMP-9 and [B] total MMP-2 AUC in serum from cynomologus monkeys following daily orogastric gavage dosing for 72 hours (n=6). Doses used were 1.6 mg/kg doxycycline hyclate at time 0 and 4.8 mg/kg doxycycline hyclate at 24 and 48 hours, or the molar equivalents of SI1004.
Figure 12:
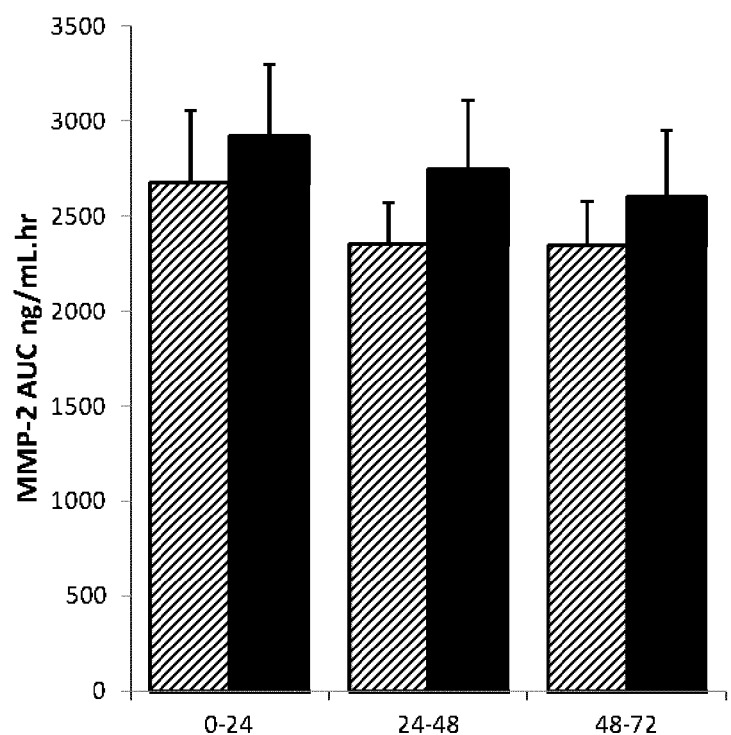

Plasma MMP-2 and MMP-9 Levels Over 72 Hours with Daily Dosing of Doxycycline and SI1004 in Cynomolgus Monkeys Oral administration of SI1004 caused more effective suppression of total serum MMP-9 protein levels than doxycycline (FIG. 12A). Between-group differences were significant by day 2 and remained significant on day 3 in terms of AUC (24-48 and 48-72 hours) and also in terms of MMP-9 change from baseline at 48 and 72 hours (all $p<0.05$). Total MMP-2 levels were similar over the 3-day treatment period (FIG. 12B). Maximum plasma doxycycline concentration (Cmax) was noted on day 3 of dosing where plasma doxycycline concentration achieved 5.1 µM (base equivalents). SI1004 caused an increase in mean plasma nitrite/nitrate (NOx) over the duration of the dosing period, with peaks at 6 hours post-dosing (i.e. at 6, 30 and 54 hours) consistent with activation of the SI1004 nitrate group and NO release. NOx Cmax (µg/mL) for SI1004 was 12.1±2.2, 47.9±2.2, and 50.4±12.5, on days 1, 2 and 3 respectively (all at 6 hours post dose). Although the mean systolic blood pressure was higher in the doxycycline hyclate group (109.7±7.1 mmHg vs 101±6.3, $p<0.01$), there was no difference in diastolic blood pressure (58.6±6.0 mmHg vs 56.4±3.8 mmHg, p=NS) and the pattern of NO release was not associated with significant differences in blood pressure (either systolic or diastolic) or heart rate at any time point.

TABLE 1

Impact of doxycycline hyclate and SI1004 on MMPs, TIMP-1, interleukins and MCP-1 protein levels in supernatants of PBMC treated over 24 hours (n = 3).

| | All values are mean ± SEM (ng/mL) | | | | |
|---|---|---|---|---|---|
| | Control No.(%)/Mean ± SD | Doxycycline (150 µM) | Doxycycline (75 µM) | SI1004 (150 µM) | SI1004 (75 µM) |
| | | | No.(%)/Mean ± SD | | |
| Interleukin-1β | 40.8 ± 6.2 | 30.6 ± 5.0 | 34.6 ± 5.8 | 24.6 ± 1.2 | 27.8 ± 6.6 |
| Interleukin-4 | 12.0 ± 0.6 | 9.8 ± 0.8 | 9.4 ± 1.2 | 9.6 ± 0.6 | 10.8 ± 0.2 |
| Interleukin-5 | 49.8 ± 11.6 | 31.2 ± 5.8 | 40.8 ± 9.0 | 35.6 ± 6.4 | 35.8 ± 8.4 |
| Interleukin-8 | 15322 ± 264 | 6352 ± 1438 | 8852 ± 2568 | 8826 ± 1364 | 10960 ± 484 |

TABLE 1-continued

Impact of doxycycline hyclate and SI1004 on MMPs, TIMP-1, interleukins and MCP-1 protein levels in supernatants of PBMC treated over 24 hours (n = 3).

| | All values are mean ± SEM (ng/mL) | | | | |
|---|---|---|---|---|---|
| | Control | Doxycycline (150 µM) | Doxycycline (75 µM) | SI1004 (150 µM) | SI1004 (75 µM) |
| | No.(%)/Mean ± SD | | No.(%)/Mean ± SD | | |
| Interleukin-10 | 121.2 ± 51.2 | 92.2 ± 33.8 | 136.6 ± 74.2 | 142.0 ± 55.2 | 125.6 ± 32.2 |
| Interleukin-12p70 | 19.8 ± 1.0 | 14.2 ± 2.0⌐ | 16.2 ± 2.4⌐ | 15.2 ± 1.0⌐ | 16.6 ± 1.1⌐ |
| Interleukin-13 | 106.6 ± 0.6 | 80.2 ± 3.2 | 79.6 ± 17.2 | 89.4 ± 13.2 | 80.8 ± 24.8 |
| MCP-1 | 598 ± 338 | 30.0 ± 8.0⌐ | 92.0 ± 54.0⌐ | 40.0 ± 14.0⌐ | 146 ± 54⌐ |
| Interferon γ | 124.4 ± 6.8 | 86.6 ± 8.8⌐ | 99.5 ± 15.0⌐ | 100.2 ± 7.0⌐ | 102.8 ± 4.8 |
| MMP-1 | 262 ± 132 | 134 ± 48 | 144.0 ± 80.0 | 171 ± 66.0 | 208 ± 102 |
| MMP-2 | 126.0 ± 104.6 | 96.8 ± 80.6 | 61.4 ± 54.2 | 95.4 ± 52 | 120.4 ± 86.4 |
| MMP-3 | 11.3 ± 2.8 | 2.9 ± 0.4⌐ | 1.5 ± 1.5⫼ | 9.1 ± 6.1* | 8.7 ± 5.2* |
| MMP-9 | 29.4 ± 7.6 | 1.3 ± 0.6⌐ | 3.4 ± 1.6⫼ | 8.4 ± 2.1** | 18.4 ± 7.3* |
| MMP-10 | 84.4 ± 25.2 | 47.6 ± 15.8 | 36.0 ± 14.0 | 29.0 ± 14.6 | 26.6 ± 18.4 |
| TIMP-1 | 56.0 ± 4.2 | 6.8 ± 2.4⌐ | 12.6 ± 1.6⫼ | 22.0 ± 9.1* | 32.4 ± 9.4* |

All values represent mean and SEM.
⌐ represents $p < 0.05$ vs. TNFα treated controls,
⫼ - $p < 0.01$ vs TNFα treated controls,
*$p < 0.05$ vs. Doxy,
**$p < 0.01$ vs. Doxy.
Abbreviations:
MCP = monocyte chemotactic protein,
MMP = matrix metalloproteinase,
TIMP = tissue inhibitor of matrix metalloproteinase.

SI1004 and doxycycline have low binding capacity to MMP-2 and MMP-9 enzymes at concentrations achieved in-vivo. Both compounds inhibit TNFα induced MMP-9, TIMP-1, IFNγ, IL-8, IL-12p70 and MCP-1 expression in PBMC. Unlike doxycycline, SI1004 inhibits IL-1β and also TNFα induced MMP-9 mRNA in HCF and HCF proliferation. SI1004 has similar effects on MMP-2 in-vivo and more effectively reduces total plasma MMP-9 (median AUC 4.3 µg/mL.hour, IQR 3.1-5.5) than doxycycline (median AUC 8.7 µg/mL.hour, IQR 7.3-11.3, $p<0.05$ vs doxycycline) in NHPs.

Conclusions: This study demonstrates that doxycycline and SI1004 are immunemodulatory MMP inhibitors. SI1004 provides more effective inhibition of inducible MMP-9 than doxycycline.

Discussion

HFpEF accounts for 40-60% of all cases of HF and is set to increase with continued high prevalence of ALVDD driven principally by hypertension and diabetes. Experience to date with renin-angiotensin-aldosterone system (RMS) modifying therapies suggests that novel therapeutic approaches are needed. While RMS modifying therapies have shown anti-fibrotic effects, several lines of in-vitro and in-vivo evidence point to co-existing inflammation and ECM remodeling as key drivers of HFpEF pathophysiology. ECM remodeling is regulated by myocardial MMPs and TIMPs which have been elusive pharmacological targets in the clinic. The present study provides a pharmacological and pathophysiological rationale for further evaluation of immunomodulatory, broad-spectrum MMP inhibitor doxycycline and its novel NO-releasing analogue (SI1004) as components of an anti-remodeling strategy in ALVDD and HFpEF. Furthermore, SI1004 reduces transcription of inducible myocardial MMP-9 and total MMP-9 in-vivo more effectively than doxycycline and this may provide efficacy and safety advantages in chronic therapy. Abnormalities in the cardiac interstitium are central to the pathophysiology of ALVDD and HFpEF. These abnormalities include delayed relaxation, impaired left ventricular filling and/or increased stiffness in the myocardium. Myocardial remodeling is characterized by inflammation, fibrosis (increased collagen production, reduced collagen breakdown, alterations in the relative balance of collagen I/III, changes in the biomechanical properties of myocardial collagen) and alterations in other components of the ECM such as fibronectin, laminin and elastin. Modulation of the cardiac interstitium in pressure/volume overload is partially regulated by MMPs and TIMPs and recent human studies have associated serum and tissue myocardial MMP levels with increased arterial stiffness in patients with hypertension, hypertrophic obstructive cardiomyopathy, diastolic dysfunction and HFpEF. Supporting these observations are animal studies showing MMP-9 and its tissue inhibitor, TIMP-1, are associated with the transition from hypertrophy to HF the development of diastolic dysfunction and HFpEF in models of chronic pressure-overload. MMP-2 and MMP-9 knockout mice develop less marked cardiomyocyte hypertrophy and fibrosis following transverse aortic banding and pharmacological MMP inhibition prevents ventricular remodeling and HF in pressure overload states, including HF induced by inflammatory cytokines. However, direct pharmacological inhibition of MMPs has been unsuccessful as a chronic therapy in the clinic. Over 60 MMP-binding inhibitors have been tested, primarily in cancer and heart disease, with consistently disappointing efficacy or unacceptable side-effect profiles. The 24 human MMPs and their TIMPs also contribute to a large array of important physiological processes. Thus, for example, chronic, direct inhibition of collagenases may actually facilitate myocardial fibrosis in pressure overload states. It is important to note that MMP-2 has collagenase activity and activates other collagenases, unlike MMP-9, suggesting it may have role in the attenuation of excess collagen deposition in the myocardium. Conversely, MMP-9 basal activity is normally low but its gene contains binding sites for AP-1, NF-κB, Sp-1, Ets-1 and Egr-1. Global deletion of MMP-9, endows mice with a benign phenotype in the absence of pathophysiological stress. However, following induction of myocardial infarction, MMP-9 knockout mice demonstrate reduced macrophage infiltration, left ventricular dilation and collagen accumulation as well as increased vascularity and perfusion. Taken together, these data indicate that pharmacological attenuation of inducible myocardial MMP-9 and MMP secretion without chronic direct enzyme inhibition could be an effective and/or safer therapeutic approach in patients with ALVDD and HFpEF. Doxycycline is the only therapy licensed for human use as a MMP inhibitor, in the setting of periodontal disease, and is currently under investigation by our group in ALVDD and HFpEF (EudraCT number: 2010-021664-16). As well as direct inhibitory effects on a range of MMPs, doxycycline also inhibits the acute phase MMP-9 release from tertiary granules in neutrophils. The present study suggests that doxycycline has low binding capacity for myocardial MMP at plasma levels achieved in this study and during chronic human dosing (<10 µM) and this may be an advantage in terms of long term safety at conventional doses. Furthermore, the effect of doxycycline and SI004 on IFNγ and IL-12p70 secretion by TNFα stimulated PBMCs suggests a reduced capacity to promote T cell activation. Both agents also suppress IL-8 and MCP-1 secretion from activated PBMCs indicating an ability to inhibit neutrophil and monocyte chemotaxis. These data are in accordance with previous in-vivo evidence of doxycycline suppression of neutrophil and cytotoxic T cell accumulation in the aortic wall of patients undergoing elective aneurysmal repair. Given the emerging importance of inflammation in the early phases of HFpEF and the potentially causal role of MCP-1 in the recruitment of monocytes and initiation of interstitial fibrosis in animal models of pressure overload our data suggest a beneficial anti-inflammatory role for doxycycline and SI004 in ALVDD and HFpEF. The additional effects of NO release on pro-inflammatory stimuli and gelatinase activity may amplify doxycycline's inhibitory effect in the setting of HFpEF. Doxycycline reduces NO and peroxynitrite levels in multiple cell types stimulated with inflammatory cytokines, partly through inducible nitric oxide synthase (iNOS) inhibition. It is also known that intracellular NO formation can suppress IL-1β by inhibiting caspase-1, the IL-1β converting enzyme which may explain the significant reduction of SI004 on this inflammatory cytokine. NO can also affect the cellular distribution and compartmentalization of MMP-9, decrease MMP-9 mRNA stability and inhibit its transcription via effects on AP-1, NF☐B and PEA3 promoter activity. Furthermore, vascular NO is depleted in hypertension and NO has well-known effects on vascular smooth muscle cells, activating guanylate cyclase and increasing the formation of cyclic guanosine monophosphate (cGMP), causing vasorelaxation, reduced pulse wave reflection and reduced central aortic pressure. NO and cGMP releasing substances are associated with an improvement in diastolic relaxation that suggest a beneficial effect in diastolic HF. A final potential advantage of nitrocycline is that while short and long-term use of doxycycline can cause gastro-eosophageal irritation, NO is gastroprotective and NO donor groups can increase the intestinal tolerability and safety of a number of drugs. The present study identifies a number of key differences between SI1004 and its parent molecule. Of potential importance in myocardial remodeling is that SI1004 has superior efficacy on MMP-9 mRNA in TNF☐ stimulated HCF. SI1004 may have less inhibitory effects on TIMP-1 and MMP-3 which are associated with the attenuation of myocardial remodeling and increased scar volume after myocardial injury. By processing samples to serum with complete clotting, which causes degranulation of PBMCs and platelets, we obtained an index of total MMP-9 protein in-vivo. SI1004 was strikingly more effective than doxycycline hyclate in the inhibition of MMP-9, consistent with inhibitory effects on MMP-9 RNA and a broader anti-inflammatory profile. These effects may make the nitrocycline approach therapeutically relevant in pathologies where there is a strong inflammatory component associated with elevated MMP-9 levels including ALVDD and HFpEF. In conclusion, ALVDD and HFpEF are diseases driven by inflammation, fibrosis and abnormalities of ECM turnover. This study presents in-vitro and in-vivo evidence of efficacy of doxycycline and SI1004, a novel, NO-releasing tetracycline analogue, as immunomodulatory, MMP inhibitors. SI1004 is a more effective inhibitor of MMP-9 transcription and serum MMP-9 in NHPs, than doxycycline. These agents are considered to be useful in treatment of diseases associated with elevated MMP.

Cancer Applications

As discussed in the background section, Matrix Metalloproteinase (MMP) levels in the plasma are known biomarkers of breast, colorectal, renal, pancreas, bladder and lung cancers (see Table 2).

TABLE 2

Candidate MMP and ADAM Biomarkers of Cancer
(Roy, Yang et al. 2009)

| Type of Cancer and MMPs/ADAMs | Detected in Tissue/Body Fluid |
|---|---|
| Breast | |
| MMP-13 | Tissue |
| MMP-9, TIMP-1 | Serum, tissue |
| MMP-9 | Urine, serum, plasma, tissue |
| ADAM12 | Urine |
| ADAM17 | Tissue |
| MMP-1 | Tissue, nipple aspirates |
| Pancreas | |
| MMP-9 | Pancreatic juice, serum |
| MMP-2 | Pancreatic juice, tissue |
| MMP-7 | Tissue, plasma |
| ADAM9 | Tissue |
| Lung | |
| VMMP-9, TIMP-1 | Serum, bronchial lavage |
| MMP-7 | Tissue |
| MMP-1 | Tissue |
| Bladder | |
| MMP-9 | Tissue |
| MMP-9, MMP-2 | Urine |
| MMP-9 | Urine |
| MMP-9, telomerase | Urine |
| Colorectal | |
| MMP-2 | Tissue, plasma |
| MMP-9 | Tissue |
| MMP-2, MMP-9 | Plasma |
| MMP-7 | Serum |
| MMP-1 | Tissue |
| MMP-13 | Tissue |
| Ovarian | |
| MMP-9 | Tissue |
| MMP-9, MMP-14 | Tissue |
| MMP-2 | Tissue |
| MMP-2, MMP-9, MMP-14 | Tissue |
| ADAM17 | Tissue |
| Prostate | |
| MMP-2, MMP-9 | Plasma, tissue |
| MMP-2 | Tissue |
| MMP-9 | Urine |
| ADAM8 | Tissue |
| ADAM9 | Tissue |

TABLE 2-continued

Candidate MMP and ADAM Biomarkers of Cancer
(Roy, Yang et al. 2009)

| Type of Cancer and MMPs/ADAMs | Detected in Tissue/Body Fluid |
|---|---|
| Brain | |
| MMP-2 | Tissue |
| MMP-9 | Tissue |
| MMP-2, MMP-9 | Tissue, cerebrospinal fluid, urine |

MMPs are involved in cancer cell intravasation and extravasation. They effect Extracellular Matrix (ECM) degradation and disrupt cell-cell interactions promoting cell migration. MMP-9 is also involved in endothelial-mesenchymal-transition (EMT) whereby cells acquire migratory characteristics and this is also facilitated by MMP-3 (via interactions with E-cadherin and Rac1b). MMPs modulate growth factors and receptors. MMP-9 modulates vascular endothelial growth factors which promotes tumour growth and angiogenesis. MMP-3 modulates insulin like growth factor binding proteins and basic fibroblast growth factors and is also known to activate MMP-9. MMPs also modulate tumour associated inflammation (e.g. MMP-9 is involved in breast cancer inflammation) via cytokines and their receptors.

Anti Cancer Effect of the Compounds of the Invention

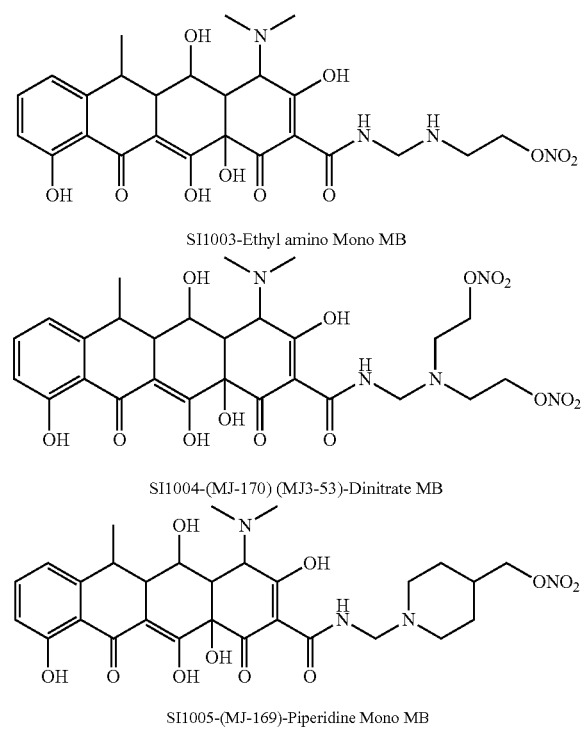

SI1003-Ethyl amino Mono MB

SI1004-(MJ-170) (MJ3-53)-Dinitrate MB

SI1005-(MJ-169)-Piperidine Mono MB

SI1004 (MJ-170, Dinitrate MB) is a more effective MMP-9 inhibitor nitrocycline than SI1005 (MJ-169, Piperidine Mono MB), which has been shown to inhibit MMP-3. Accordingly, it may be able to more selectively reduce MMP-9 protein levels than SI1004. Both SI1004 and SI1005 are more potent MMP-9 inhibitors than conventional doxycycline.

In Vitro Data

Figure 5:
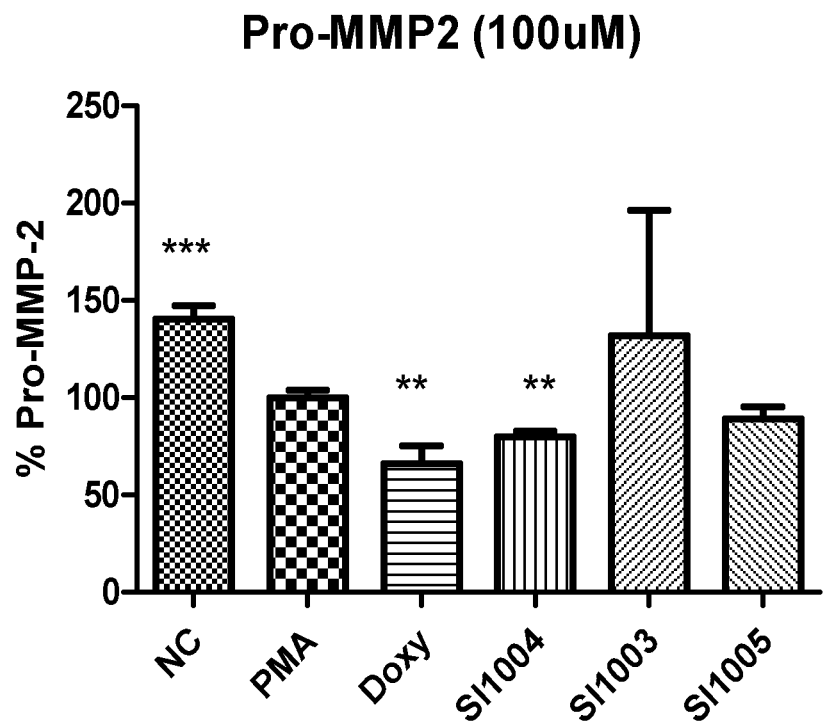
FIG. 5 demonstrates the effect of SI1003, SI1004, SI1005 and doxycycline on pro-MMP-2 activity in PMA stimulated breast cancer cells (NC=negative control).
Figure 6:
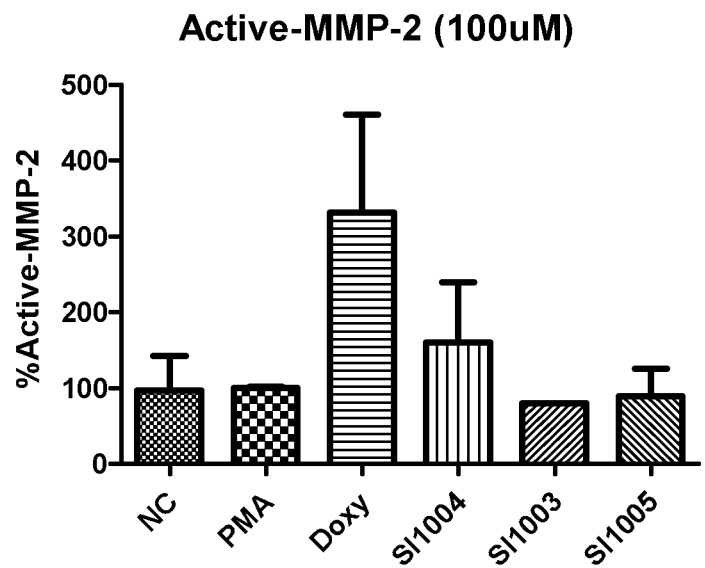
FIG. 6 demonstrates the effect of SI1003, SI1004, SI1005 and doxycycline on MMP-2 activity in PMA stimulated breast cancer cells (NC=negative control).
Figure 7:
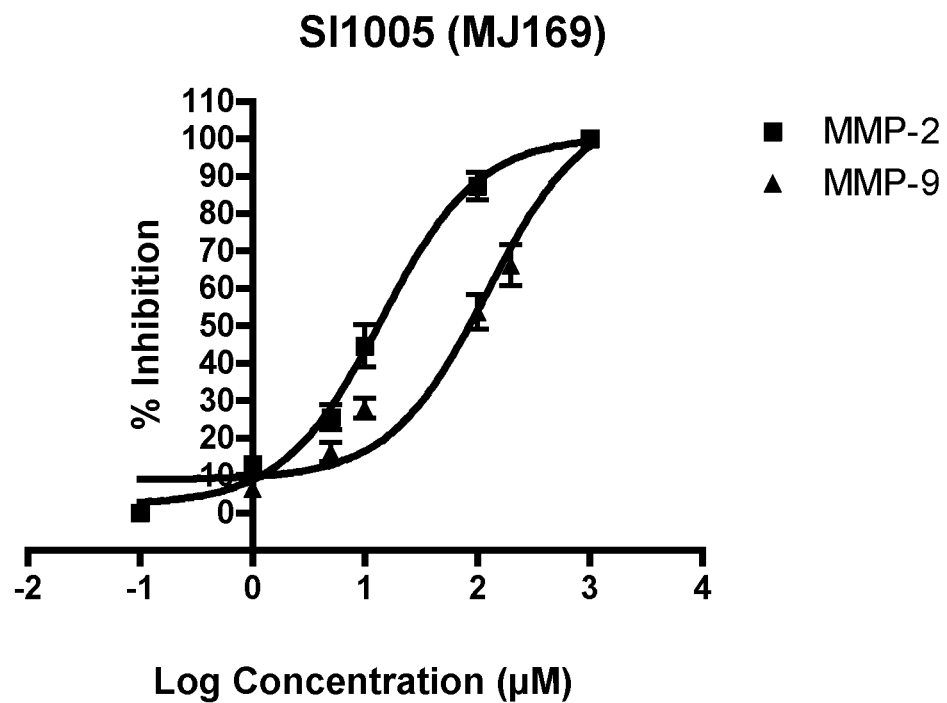
FIG. 7 demonstrates inhibition of MMP-2 and MMP-9 activity in response to SI1005 (MJ-169).
Figure 8:
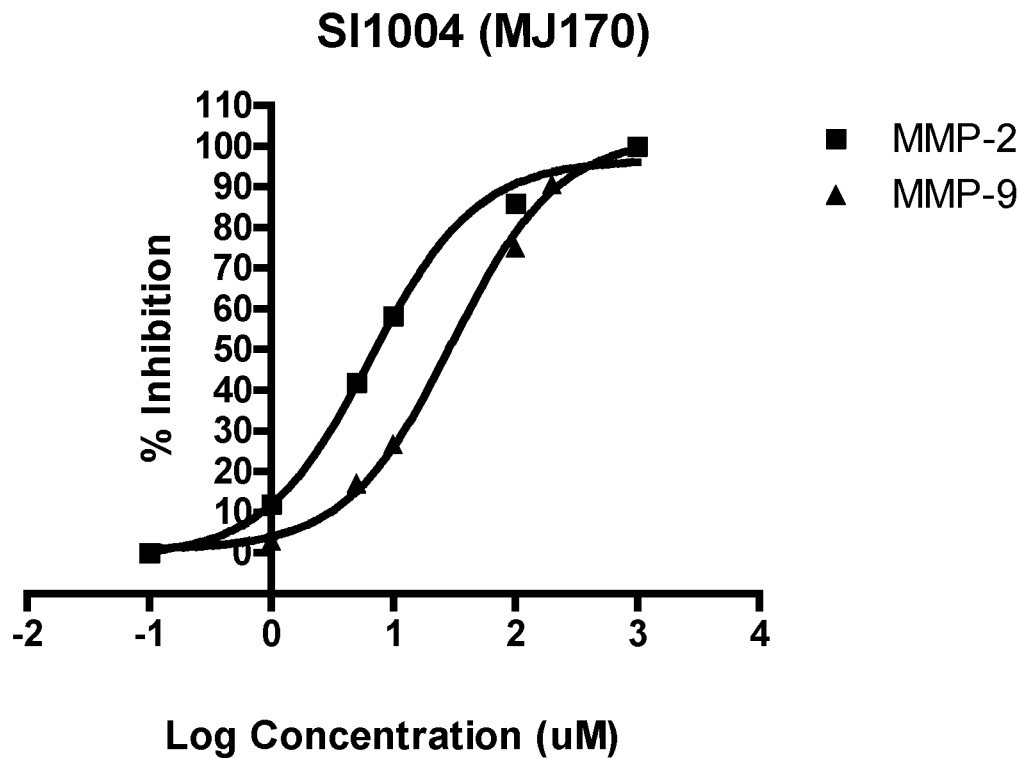
FIG. 8 demonstrates inhibition of MMP-2 and MMP-9 activity in response to SI1004 (MJ170).
Figure 9:
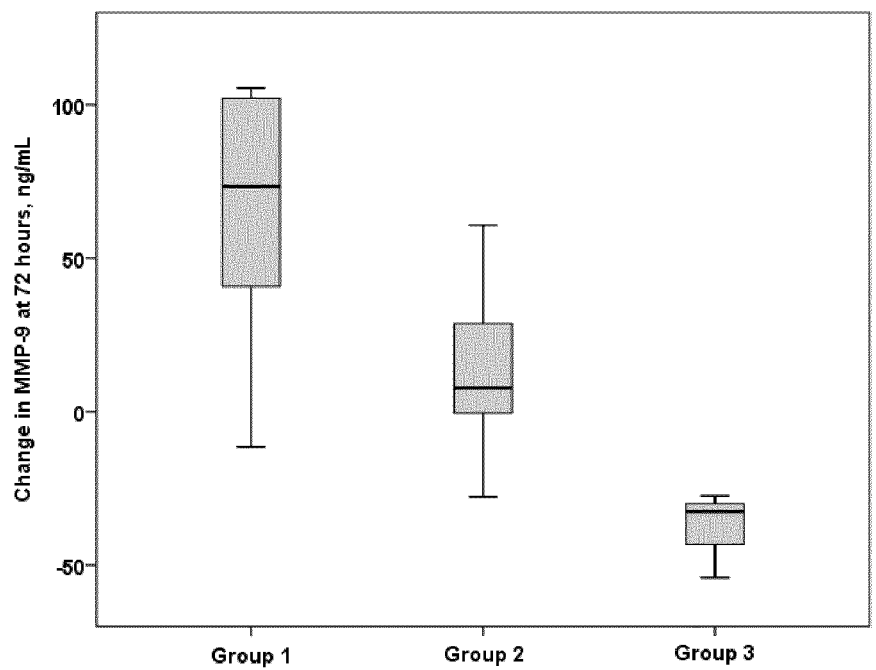
FIG. 9 demonstrates the change in plasma MMP-9 levels from baseline to 72 hours following the administration of doxycycline hyclate (Group 1), SI1004 (Group 2) and SI1005 (Group 3) to groups of 6 cynomolgus monkeys FIG. 10. Effect of Doxycycline, SI1004 and SI1005 on colon cancer cell invasiveness (NC=negative control; PC=positive control).

Using in vitro breast cancer cell models (HT1080 cells), stimulated with a pro-inflammatory insult (PMA) to stimulate the over-production of MMP-9, we see that doxycycline (Doxy), SI1004 (MJ-170, Dinitrate MB) and SI1005 (MJ-169, Piperidine Mono MB) all reduce MMP-9 production at 100 micromolar concentrations. Using the same in vitro breast cancer cell models for examining MMP-2, we see that PMA reduces pro-MMP-2 and doxycycline (Doxy), SI1004 (MJ-170, Dinitrate MB) and to a lesser extent SI1005 (MJ-169, Piperidine Mono MB) all reduce pro-MMP-2 production at 100 micromolar. However, surprisingly, doxycycline (Doxy) also appears to increase the conversion of available pro-MMP-2 to active MMP-2 (FIG. 5). This, potentially, could be a concern for chronic doxycycline therapy in the treatment of cancer. Advantageously, we do not see the same activation of MMP-2 with nitrocyclines.

Using models of direct enzyme inhibition, it is shown below that SI1004 (MJ-170, Dinitrate MB) and SI1005 (MJ-169, Piperidine Mono MB) are more potent inhibitors of MMP-9 than doxycycline. The 1050 value (µM) of SI1005 (MJ-169, Piperidine Mono MB) for MMP-2 and MMP-9 are 63 (46-84) and 139 (86-223) respectively. The $IC_{50}$ value (µM) of SI1004, (MJ-170, Dinitrate MB) for MMP-2 and MMP-9 are 9.4 (8.5-10.4) and 25 (19-32) respectively. These are more potent than doxycycline which has an approximate $IC_{50}$ value (µM) for MMP-2 and MMP-9 of 129 and 164 respectively

TABLE 2

$IC_{50}$ values for the inhibition of MMP-2 and MMP-9 in response to SI1004, SI1005 and doxycycline.

| | SI1004 (MJ-170) | SI1005 (MJ-169) | Doxycycline |
|---|---|---|---|
| MMP-2 | 9.4 µM | 63 µM | 129 µM |
| MMP-9 | 25 µM | 139 µM | 164 µM |

MMP-8: SI1005 (MJ-169, Piperidine Mono MB) has around 53.8% inhibition at 100 µM and 16.9% inhibition at 10 µM. SI1004 (MJ-170, MJ-170, Dinitrate MB) has around 60.7% inhibition at 100 µM and 26.0% inhibition at 10 µM. Doxycyline has around 42.7% inhibition at 100 µM. MMP-13: SI1005 (MJ-169, Piperidine Mono MB) has around 28.4% inhibition at 100 µM and 6.6% inhibition at 10 µM and SI1004 (MJ-170, MJ-170, Dinitrate MB) has around 74.5% inhibition at 1000 and 46.0% inhibition at 10 µM. Doxycyline has around 54% inhibition at 100 µM. MMP-1: SI1005 (MJ-169, Piperidine Mono MB) has around 22% inhibition at 100 µM and 13% inhibition at 10 µM while SI1004 (MJ-170, MJ-170, Dinitrate MB) has around 63% inhibition at 100 µM and 19% inhibition at 10 µM. Doxycyline has around 12% inhibition at 100 µM.

In Vivo Data

Figure 10:
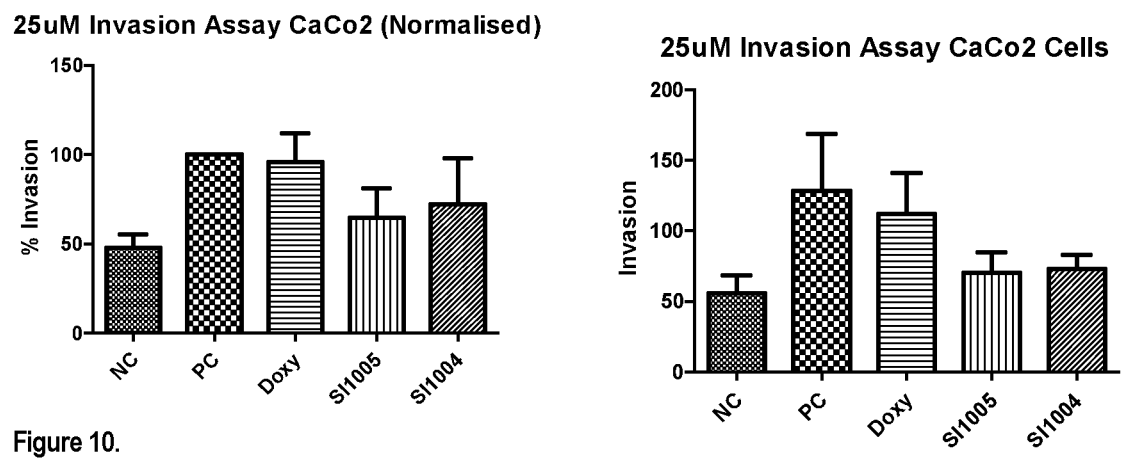
Figure 11:
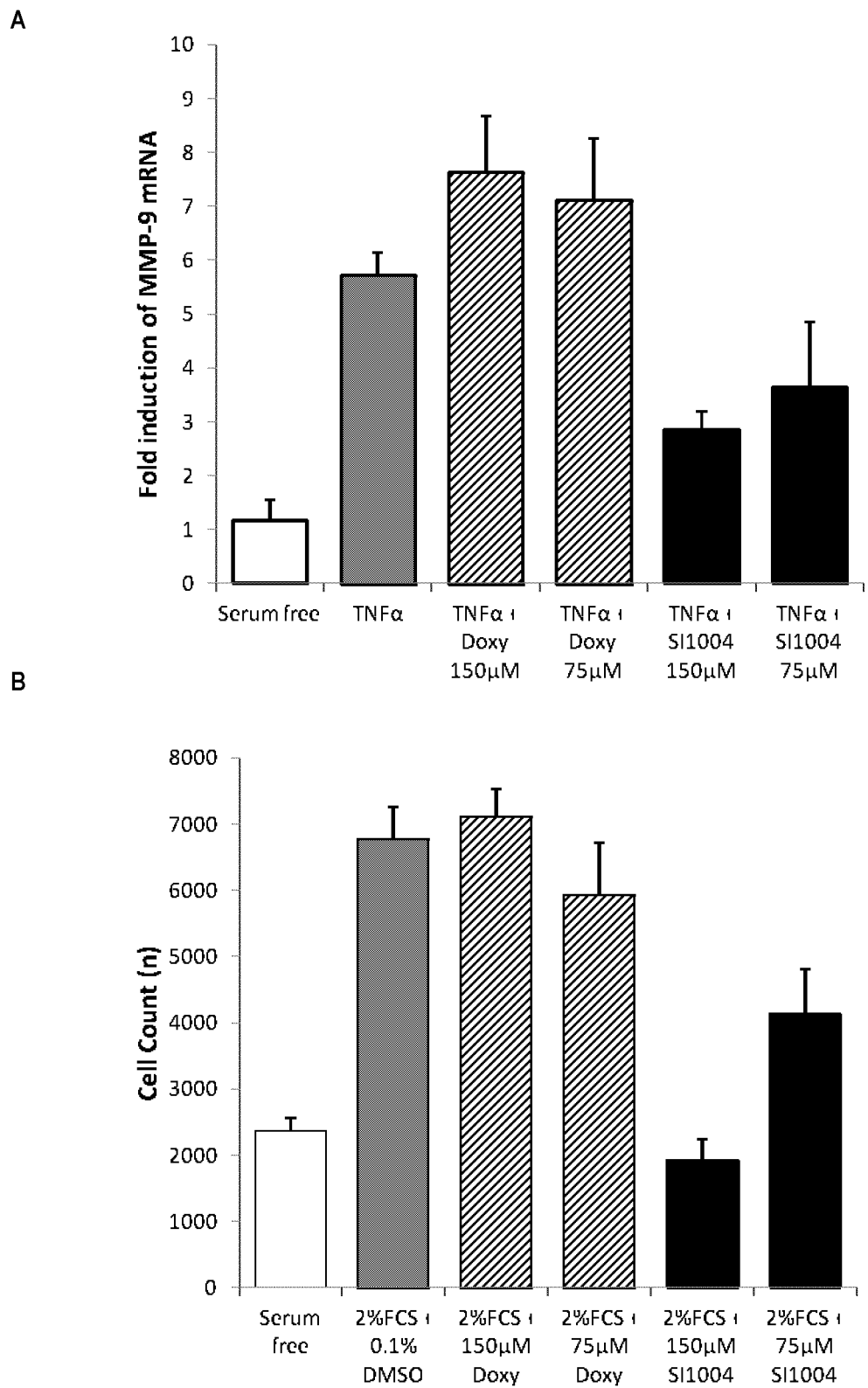
FIG. 11A. Impact of doxycycline hyclate (Doxy) and SI1004 on MMP-9 mRNA in TNFα treated human cardiac fibroblasts (n=3 per group). Shaded bar is 0.1% DMSO+TNFα; striped bars are 0.1% DMSO+Doxycycline hyclate (concentrations shown) and solid black bars represent 0.1% DMSO+SI1004 (concentrations shown). All values represent mean and SEM. I represents $p<0.01$ vs TNFα, **$p<0.01$ vs. Doxy. All bars were significantly elevated vs. serum free controls.
FIG. 11B. Impact of doxycycline hyclate (Doxy) and SI1004 on proliferation of human cardiac fibroblasts (n=3 per group) following 72 hours of serum starvation (clear bars) and subsequent exposure to 72 hours of 2% fetal calf serum (FCS) with 0.1% DMSO (shaded bars), 0.1% DMSO+Doxycycline hyclate (concentrations shown, striped bars) and 0.1% DMSO+SI1004 (concentrations shown, black solid bars). All values represent mean and SEM. □ represents $p<0.05$ vs. 2% FCS, □□$p<0.01$ vs 2% FCS, *$p<0.05$ vs. Doxy, **$p<0.01$ vs. Doxy. All bars except SI1004 150 µM were significantly elevated vs. serum free controls.

Nitrocycline compounds SI1004 (MJ-170, Dinitrate MB, Group 2), SI1005 (MJ-169, Piperidine Mono MB, Group 3) and doxycycline hyclate control (Doxy Group 1) were administered to cynomolgus monkeys (n=6 per group) as described in the method below. The test articles were administered by oral gavage once daily for three days (Doxycycline hyclate 1.6 mg/day and equimolar doses of the nitrocyclines were administered on Day 1. These doses were equivalent to 100 mg/day of doxycycline base. The dose of doxycycline hyclate was increased to 4.6 mg/kg on the second and third 20 day. Equimolar doses of nitrocyclines were administered. This dose was equivalent to a 300 mg/day dose of doxycycline base). The primary endpoint of this study was the changes in MMP-9 from baseline to 72 hours. In the high dose doxycycline group (Group 1), MMP-9 levels increase. In the SI1004 (Group 2) MMP-9 levels are significantly reduced compared to doxycycline. In the SI1005 (Group 3) MMP-9 levels are significantly reduced compared to doxycycline and SI1004. These data provide proof-of-concept in vivo support for the use of SI1004 and SI1005 as more potent inhibitors of MMP-9 compared to doxycycline. Furthermore, SI1004 and SI1005 are more potent inhibitors of inflammatory cytokines such as IL-1b, IL-4 and IL-8 compared to doxycycline (data not shown). Finally, in order to provide a functional model of tumour cell invasion, the following data show that that at low dose, doxycycline (Doxy) does not reduce colon cancer cell invasiveness, whereas SI1004 (MJ-170, Dinitrate MB) and SI1005 (MJ-169, Piperidine Mono MB) do (FIG. 10). Overall nitrocyclines SI1004 and SI1005 appear to be more potent inhibitors of MMP enzymes and this may be an advantage in the management of cardiovascular disease and cancer. SI1004 appears to be more MMP-9 specific and does not reduce MMP-3 in in vitro inflammatory cell models. Both nitrocyclines SI1004 and SI1005 are more effective immunomodulatory compounds. They do not appear to activate MMP-2, unlike high concentration (100 μM) doxycycline. Finally, they are more effective in reducing tumour cell invasiveness in an in vitro model with human colon cancer cells.

In Vivo, Non-Human Primate Study. Methods

Purpose bred, naïve, non-human primates (cynomolgus monkeys, 2.9-4 kg) were sourced and randomly allocated in a parallel group design (n=6 per group) to receive SI1004, SI1005 and equimolar doses of doxycycline daily (1.6 mg/kg doxycycline hyclate equivalents, on day 1 and 4.8 mg/kg doxycycline equivalents on days 2 and 3) by oral gavage in aqueous vehicle over a 3 day period. Studies were carried out consecutively in two contract research organization sites (Charles River, Sparks, Nev., US and Charles River, Shanghai, China). The study protocol was approved by PCS-SHG Institutional Animal Care and Use Committee before conduct. During the study, care and use of animals was conducted in accordance with the guidelines of the USA National Research Council and the Canadian Council on Animal Care. The cynomolgus monkey was chosen for this study in order to maximize the likelihood of identifying responses that are similar to those that may be expected in humans. Each animal was identified by a cage label and body tattoo and was acclimated to orogastric dosing on at least two occasions prior to the initiation of dosing. The vehicle (1% (w/v) tween 80 and 0.5% (w/v) carboxymethylcellulose in deionized water) or 1.6 mg/kg doxycycline hyclate (0 hours) or 4.8 mg/kg doxycycline hyclate (24, 48 hours) or the molar equivalent(s) of SI1004 or SI1005 were administered using an orogastric tube inserted through the mouth and advanced into the stomach. The animals were temporarily restrained (i.e. manually) for dose administration, and were not sedated. Disposable sterile syringes and orogastric tubes were used for each animal/dose. Each dose was followed by a tap water flush of approximately 5 mL. Blood samples and blood pressure measurements were taken at the following timepoints: pre-dose (0 hours) and at 2, 4, 6, 12, 24, 26, 30, 36, 48, 50, 54, 60 and 72 hours after first administration of test article. Blood (300 μL) for serum preparation was collected intoBD Vacutainer®+Serum SST™ tubes to accelerate clotting 20 minutes prior to centrifugation to allow complete clotting to occur and centrifuged at 1500-2200 rpm at 2-8° C. for 10-15 minutes. Under these conditions blood cells containing MMP, principally neutrophils and platelets, undergo full degranulation. Since artifactual elevation of MMP-9 was an unavoidable feature of repeated venipuncture in our model, it was logical to stimulate full MMP-9 release during sample collection. This provided greater inter-animal reproducibility and a more dynamic analytical range for assessing the relative effects of the test articles. Subsequent MMP-9 values provide an index of total MMP-9 including circulating enzyme, amplified by repeated venipuncture, along with the cellular load released from storage granules during clotting. The latter is influenced by earlier inflammatory signaling, transcription and storage. The serum was transferred to a cryovial and immediately stored at −70° C. until analyzed for MMP-2 and MMP-9 via a Luminex ELISA (total MMP-2 and MMP-9) within 48 hours of collection. The analysis of each time point was repeated within 5 days. Values that differed by more than 15% were repeated. The primary study endpoint was the change in plasma MMP-2 and MMP-9 levels at 72 hours. Secondary endpoints were area under the curve (AUC) values of MMP-2 and MMP-9 over the following periods: 0-24, 0-48 and 0-72 hours.

Data on Admixtures (FIGS. 13-17)

Figure 13:
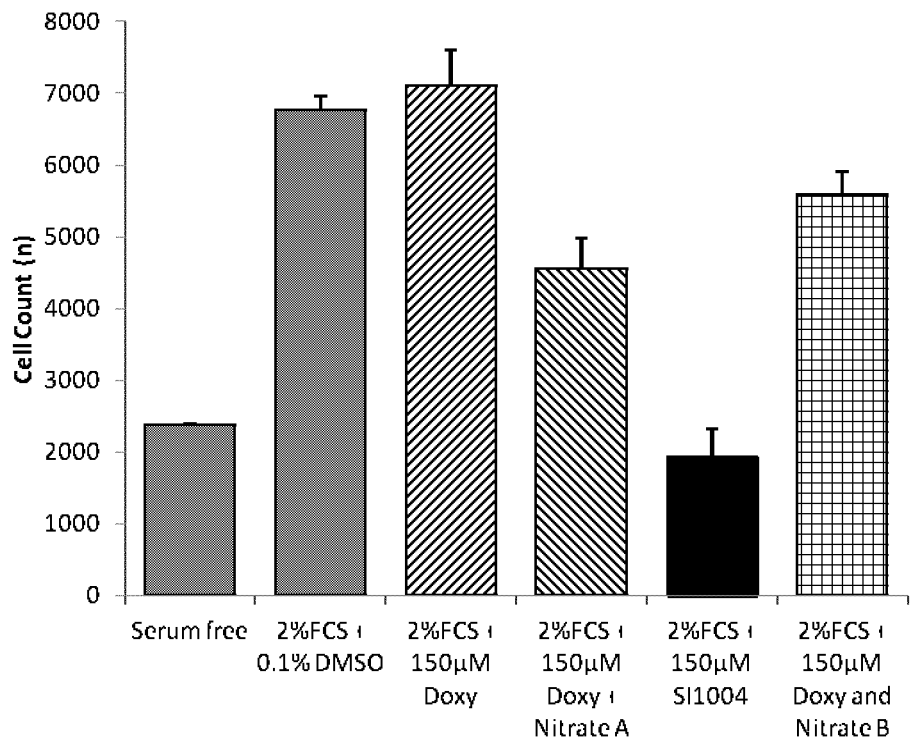
FIG. 13: Admixtures may be more effective than doxycycline in attenuating fibroblast proliferation, but not as effective as SI1004. In the following study Doxy and nitrate A are significantly better than Doxy at inhibiting Cardiac Fibroblast Proliferation ($p=0.011$) at 150 uM However, Doxy and nitrate B are not ($p=NS$) at same concentration. SI1004 is significantly more effective than doxycycline, Doxy and nitrate A, Doxy and nitrate B at 150 uM (all $p<0.01$).
Figure 14:
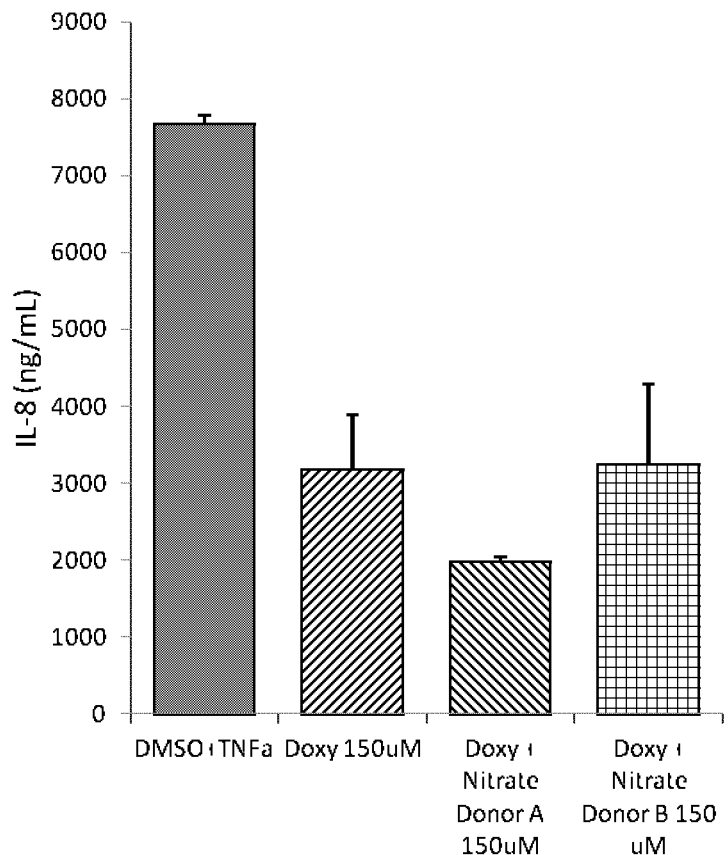
FIG. 14. Admixtures reduce some inflammatory markers similarly to Doxy, e.g. IL-8. In the following study, Doxy and nitrate A can significantly reduce IL-8 levels in TNFalpha stimulated PBMCs at 150 uM ($p<0.01$). Doxy alone and Doxy and nitrate B also reduce IL-8 levels compared to controls ($p<0.05$).
Figure 15:
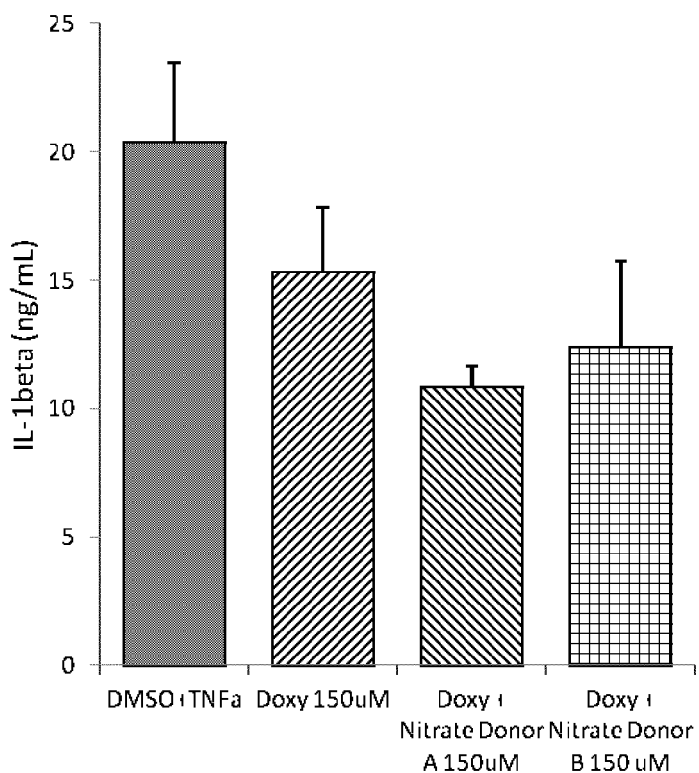
FIG. 15. Admixtures reduce some inflammatory markers more effectively than doxycycline, e.g. IL-1beta. In the following study, Doxy and nitrate A can significantly reduce IL-1 beta levels in TNFalpha stimulated PBMCs ($p<0.05$). Doxy and nitrate B reduce IL-1 beta levels, but not significantly ($p=NS$).
Figure 16:
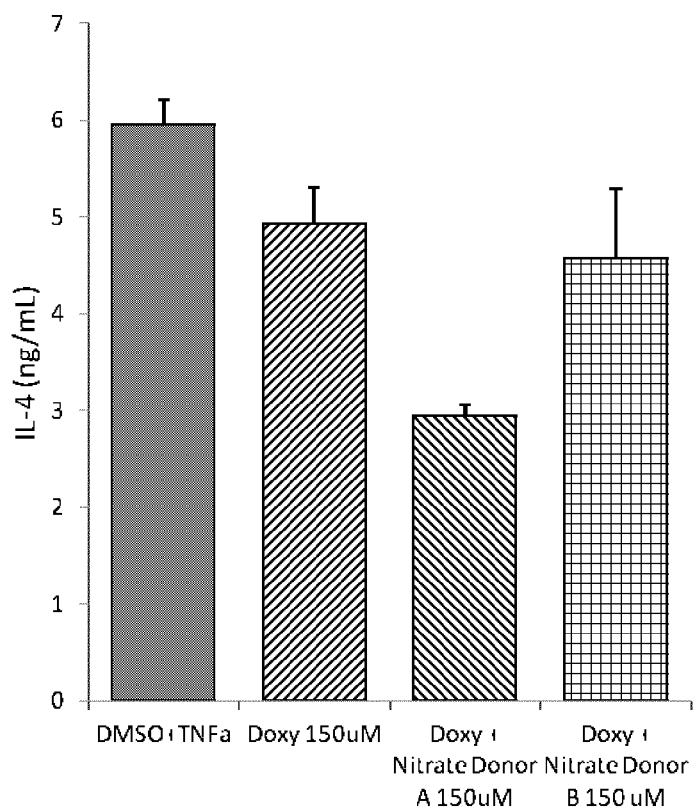
FIG. 16. Admixtures reduce some inflammatory markers more effectively than doxycycline, e.g. IL-4. In the following study, Doxy and nitrate A can significantly reduce IL-4 levels in TNFalpha stimulated PBMCs. Doxy and nitrate B admixtures reduce IL-4 levels, but not significantly ($p=NS$). IL-4 is reduced significantly more ($p<0.01$) by Doxy and nitrate A than either Doxy or Doxy and nitrate B. In this study, we see that not all NO donors provide similar efficacy.

Admixtures of tetracyclines and nitric oxide donors have benefits in inflammatory and cardiovascular diseases. In FIG. 13, Doxy and nitrate A admixture (Diethanolamine dinitrate, the alkyl nitrate component of SI1004) are significantly better than Doxy at inhibiting cardiac fibroblast proliferation (p=0.011) at 150 micromolar. However, Doxy and nitrate B admixture (Nitroxymethyl piperidine) are not (p=NS) at same concentration. The novel nitrocycline, SI1004, is significantly more effective at inhibiting cardiac fibroblast proliferation than doxycycline, Doxy and nitrate A admixture, Doxy and nitrate B admixture at 150 micromolar (all p<0.01). In some cases, inflammatory cytokines are similarly reduced by Doxy and admixtures with NO donors. In FIG. 14, Doxy and nitrate A admixtures are shown to significantly reduce IL-8 levels in TNFalpha stimulated PBMCs at 150 micromolar (p<0.01). Doxy alone and Doxy and nitrate B admixtures also reduce IL-8 levels compared to controls (p<0.05). However, in some instances, the effects Doxy and nitrate A admixture is more effective than Doxy. In FIG. 15, Doxy and nitrate A (Diethanolamine dinitrate) admixture can significantly reduce IL-1 beta levels in TNFalpha stimulated PBMCs (p<0.05). Doxy and nitrate B (Nitroxymethyl piperidine) admixture reduce IL-1 beta levels, but not significantly (p=NS). Furthermore, in some instances, the choice of NO donor dramatically alters the anti-inflammatory effects. In FIG. 16 it is shown that IL-4 is reduced significantly more (p<0.01) by Doxy and nitrate A (Diethanolamine dinitrate) admixture than either Doxy or Doxy and nitrate B (Nitroxymethyl piperidine) admixture. IL-4 is implicated in inflammatory bowel disease. IL-8 is implicated in invasive bladder cancer, chronic prostatitis, acute pyelpnephritis, non-Hodgkins lymphoma, pulmonary infections and osteomyelitis. IL-1β is implicated in fever, anemia, cryopyrinopathies (hereditary periodic fever syndromes), gout and pseudogout, Septic shock.

The invention claimed is:
1. A compound selected from:
   amido-N-[3-methylnitratepiperidinomethy]-α-6-deoxy-5-oxytetracycline
   amido-N-[N,N-diethylnitrate-aminomethyl]-α-6-deoxy-5-oxytetracycline (amido-N-[bis-(β-nitrooxyethyl)aminomethyl]-α-6-deoxy-5-oxytetracycline)
   amido-N-[(β-nitrooxyethyl)aminomethyl]-α-6-deoxy-5-oxytetracycline
   amido-N-[3-(nitrooxymethyl)piperidinomethyl]-α-6-deoxy-5-oxytetracycline
   amido-N-[3-(nitrooxymethyl)piperidinomethyl]-α-6-deoxy-5-oxytetracycline
   amido-N-[4-(nitrooxymethyl)piperidinomethyl]-α-6-deoxy-5-oxytetracycline
   amido-N-[4-nitrooxypiperidinomethyl]-α-6-deoxy-5-oxytetracycline
   amido-N-[4-nitrooxypiperidinomethyl]-tetracycline
   amido-N-[bis-(β-nitrooxyethyl)methylaminomethyl]-β-6-deoxy-5-oxytetracyclin
   amido-N-[bis-(β-nitrooxyethyl)methylaminomethyl]-α-6-deoxy-5-oxytetracyclin
   amido-N-[bis-(β-nitrooxyethyl)ethylaminomethyl]-tetracycline
   amido-N-[(β-nitrooxyethyl)aminomethyl]-tetracycline
   amido-N-[4-(nitrooxymethyl)piperidinomethyl]-tetracycline or
   amido-N-[3-(nitrooxymethyl)piperidinomethyl]-tetracycline.
2. The compound according to claim 1 selected from the group consisting of:

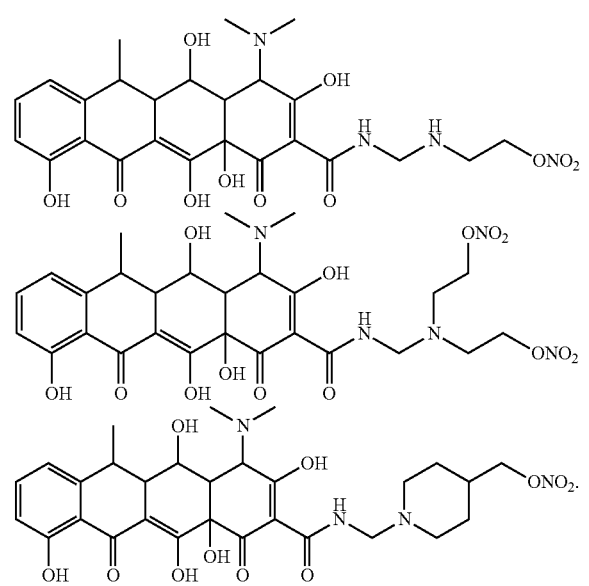

3. A compound selected from the group consisting of:

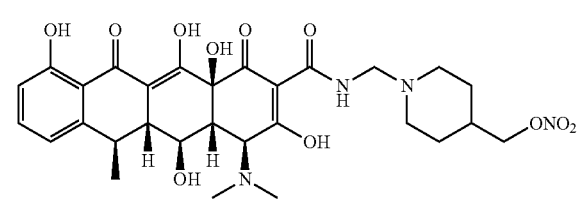

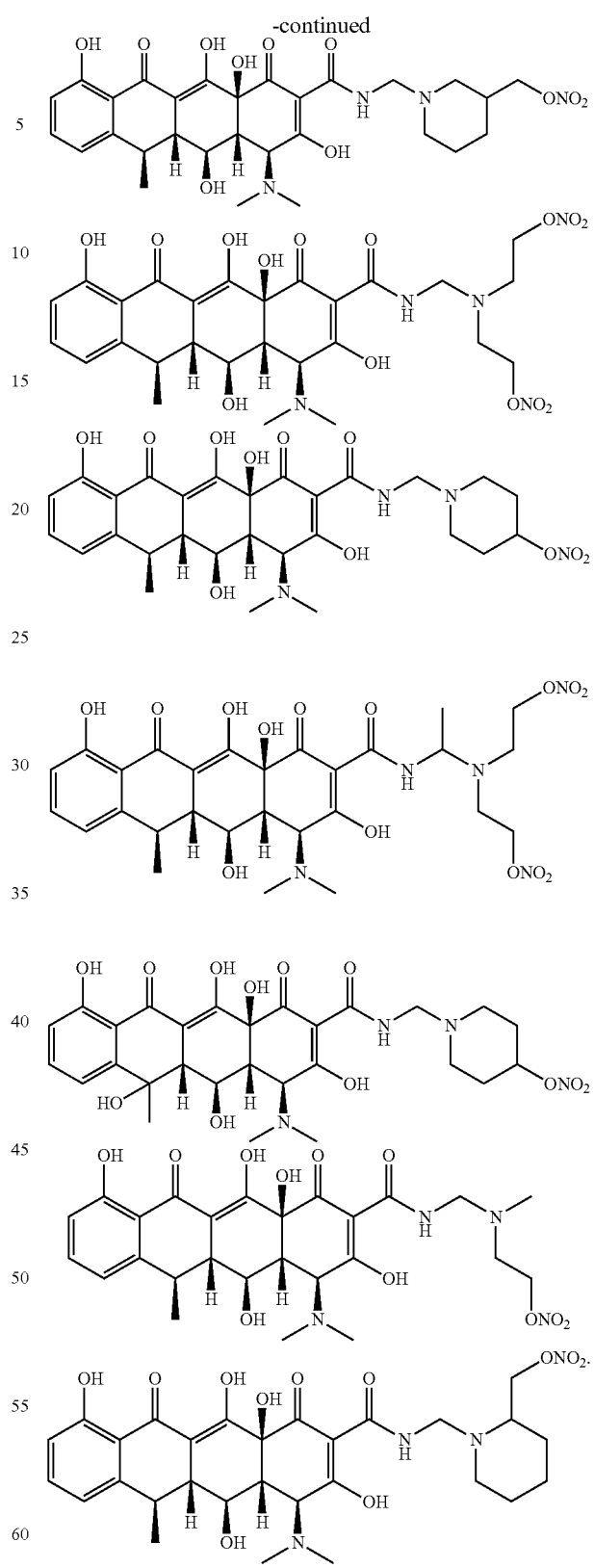

4. A pharmaceutical composition comprising a compound according to any one of claims 1, 2, and 3 and a carrier.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: MMP-2 forward primer

<400> SEQUENCE: 1
cacgtgacaa gcccatgggg cccc                                              24

<210> SEQ ID NO 2
<211> LENGTH: 25
<212> TYPE: DNA
<213> ORGANISM: Artificial Sequence
<220> FEATURE:
<223> OTHER INFORMATION: MMP-2 reverse primer

<400> SEQUENCE: 2
gcagcctagc cagtcggatt tgatg                                             25

<210> SEQ ID NO 3
<211> LENGTH: 22
<212> TYPE: DNA
<213> ORGANISM: Artificial Sequence
<220> FEATURE:
<223> OTHER INFORMATION: MMP-9 forward primer

<400> SEQUENCE: 3
gtgctgggct gctgctttgc tg                                                22

<210> SEQ ID NO 4
<211> LENGTH: 22
<212> TYPE: DNA
<213> ORGANISM: Artificial Sequence
<220> FEATURE:
<223> OTHER INFORMATION: MMP-9 reverse primer

<400> SEQUENCE: 4
gtcgccctca aaggtttgga at                                                22

<210> SEQ ID NO 5
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 5
acagtcagcc gcatcttctt                                                   20

<210> SEQ ID NO 6
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 6
acgaccaaat ccgttgactc                                                   20
```